US010077231B2

(12) United States Patent
Teran et al.

(10) Patent No.: US 10,077,231 B2
(45) Date of Patent: Sep. 18, 2018

(54) FUNCTIONALIZED FLUOROPOLYMERS AND ELECTROLYTE COMPOSITIONS

(71) Applicant: Blue Current, Inc., Berkeley, CA (US)

(72) Inventors: Alexander Teran, Oakland, CA (US); Benjamin Rupert, Berkeley, CA (US); Eduard Nasybulin, Fremont, CA (US); Joanna Burdynska, Berkeley, CA (US)

(73) Assignee: Blue Current, Inc., Berkeley, CA (US)

( * ) Notice: Subject to any disclaimer, the term of this patent is extended or adjusted under 35 U.S.C. 154(b) by 145 days.

(21) Appl. No.: 15/012,483

(22) Filed: Feb. 1, 2016

(65) Prior Publication Data
US 2016/0226102 A1 Aug. 4, 2016

Related U.S. Application Data

(60) Provisional application No. 62/111,213, filed on Feb. 3, 2015, provisional application No. 62/130,238, filed
(Continued)

(51) Int. Cl.
H01M 10/0569 (2010.01)
H01M 10/0568 (2010.01)
(Continued)

(52) U.S. Cl.
CPC ......... C07C 69/96 (2013.01); H01M 10/0567 (2013.01); H01M 10/0568 (2013.01);
(Continued)

(58) Field of Classification Search
CPC .............. C07C 69/96; H01M 10/4235; H01M 10/0568; H01M 10/0567; H01M 10/0569;
(Continued)

(56) References Cited

U.S. PATENT DOCUMENTS 4,178,465 A 12/1979 Caporiccio et al.
4,360,645 A 11/1982 Krespan et al.
(Continued)

FOREIGN PATENT DOCUMENTS

AU 2003265336 2/2009
CN 100376602 C 6/2004
(Continued)

OTHER PUBLICATIONS

English machine translation of JP10149840 to Yokoyama. (Year: 1998).*
(Continued)

Primary Examiner — Lisa S Park
(74) Attorney, Agent, or Firm — Weaver Austin Villeneuve & Sampson LLP

(57) ABSTRACT

Provided herein are functionally substituted fluoropolymers suitable for use in liquid and solid non-flammable electrolyte compositions. The functionally substituted fluoropolymers include perfluoropolyethers (PFPEs) having high ionic conductivity. Also provided are non-flammable electrolyte compositions including functionally substituted PFPEs and alkali-metal ion batteries including the non-flammable electrolyte compositions.

37 Claims, 18 Drawing Sheets

Related U.S. Application Data on Mar. 9, 2015, provisional application No. 62/147,053, filed on Apr. 14, 2015, provisional application No. 62/111,217, filed on Feb. 3, 2015, provisional application No. 62/147,047, filed on Apr. 14, 2015, provisional application No. 62/211,412, filed on Aug. 28, 2015.

(51) Int. Cl.

| | | |
|---|---|---|
| C07C 69/96 | (2006.01) | |
| H01M 10/0567 | (2010.01) | |
| H01M 10/42 | (2006.01) | |
| H01M 10/0525 | (2010.01) | |
| H01M 4/66 | (2006.01) | |
| H01M 4/02 | (2006.01) | |
| H01M 10/0565 | (2010.01) | |

(52) U.S. Cl.
CPC ... *H01M 10/0569* (2013.01); *H01M 10/4235* (2013.01); *H01M 4/661* (2013.01); *H01M 10/0525* (2013.01); *H01M 10/0565* (2013.01); *H01M 2004/028* (2013.01); *H01M 2220/10* (2013.01); *H01M 2220/20* (2013.01); *H01M 2300/0034* (2013.01); *H01M 2300/0037* (2013.01); *H01M 2300/0082* (2013.01); *Y02E 60/122* (2013.01)

(58) Field of Classification Search
CPC ......... H01M 2220/20; H01M 2220/10; H01M 4/661; H01M 10/0565; H01M 2300/0082; H01M 2004/028; H01M 10/0525; H01M 2300/0037; H01M 2300/0034; Y02E 60/122

See application file for complete search history.

(56) References Cited

U.S. PATENT DOCUMENTS

| | | | |
|---|---|---|---|
| 4,686,241 A | | 8/1987 | Fielding et al. |
| 4,745,009 A | | 5/1988 | Piacenti et al. |
| 4,808,651 A | * | 2/1989 | Blickle ............... B01D 65/108 524/366 |
| 5,011,751 A | | 4/1991 | Yoneyama |
| 5,132,446 A | | 7/1992 | Tonhzuka et al. |
| 5,506,279 A | | 4/1996 | Babu et al. |
| 5,612,043 A | | 3/1997 | Deprez et al. |
| 5,618,316 A | | 4/1997 | Hoffman et al. |
| 5,721,070 A | | 2/1998 | Shackle |
| 5,725,802 A | | 3/1998 | Chittofrati et al. |
| 5,777,174 A | | 7/1998 | Marchionni et al. |
| 5,830,600 A | | 11/1998 | Narang et al. |
| 5,874,169 A | | 2/1999 | Falcone et al. |
| 5,900,500 A | | 5/1999 | Turri et al. |
| 6,096,692 A | | 8/2000 | Hagihara et al. |
| 6,190,574 B1 | | 2/2001 | Nakagawa et al. |
| 6,235,689 B1 | | 5/2001 | Falcone |
| 6,413,676 B1 | | 7/2002 | Munshi |
| 6,515,075 B1 | | 2/2003 | Balogh et al. |
| 6,608,138 B2 | | 8/2003 | Carignano et al. |
| 6,734,264 B1 | | 5/2004 | Amin-Sanayei |
| 6,797,437 B2 | | 9/2004 | Tsukamoto et al. |
| 6,844,134 B2 | | 1/2005 | Choi et al. |
| 6,896,996 B2 | | 5/2005 | Marchionni et al. |
| 6,958,256 B2 | | 10/2005 | Rogalli et al. |
| 7,294,731 B1 | | 11/2007 | Flynn et al. |
| 7,370,962 B2 | | 5/2008 | Roffman et al. |
| 7,429,409 B2 | | 9/2008 | Husemann |
| 7,476,468 B1 | | 1/2009 | Lam et al. |
| 7,482,098 B2 | | 1/2009 | Tsukamoto et al. |
| 7,608,600 B2 | | 10/2009 | Storer et al. |
| 7,732,100 B2 | | 6/2010 | Wakihara et al. |
| 7,790,312 B2 | | 9/2010 | Costello et al. |
| 7,897,080 B2 | | 3/2011 | Yang et al. |
| 7,989,566 B2 | | 8/2011 | Coughlin et al. |
| 8,034,490 B2 | | 10/2011 | Araki et al. |
| 8,080,615 B2 | | 12/2011 | Millward |
| 8,084,405 B2 | | 12/2011 | Howell et al. |
| 8,133,580 B2 | | 3/2012 | Dias et al. |
| 8,158,728 B2 | | 4/2012 | DeSimone et al. |
| 8,197,943 B2 | | 6/2012 | Pinto et al. |
| 8,337,986 B2 | | 12/2012 | Moorlag et al. |
| 8,361,620 B2 | | 1/2013 | Zang et al. |
| 8,409,177 B1 | | 4/2013 | Lai |
| 8,475,688 B2 | | 7/2013 | Chen et al. |
| 8,802,301 B2 | | 8/2014 | Halalay et al. |
| 9,540,312 B2 | | 1/2017 | Teran et al. |
| 9,543,619 B2 | | 1/2017 | Teran et al. |
| 9,748,604 B2 | | 8/2017 | DeSimone et al. |
| 9,755,273 B2 | | 9/2017 | DeSimone et al. |
| 2002/0127475 A1 | | 9/2002 | Marchionni et al. |
| 2003/0027732 A1 | | 2/2003 | Howell et al. |
| 2003/0215719 A1 | | 11/2003 | Navarrini et al. |
| 2004/0141150 A1 | | 7/2004 | Roffman et al. |
| 2009/0004568 A1 | * | 1/2009 | Hirose ............... H01M 2/0285 429/221 |
| 2009/0023038 A1 | | 1/2009 | DeSimone et al. |
| 2009/0086408 A1 | | 4/2009 | Koh et al. |
| 2009/0111019 A1 | | 4/2009 | Hirose et al. |
| 2009/0134353 A1 | | 5/2009 | Koh et al. |
| 2009/0197090 A1 | | 8/2009 | Hahn et al. |
| 2009/0291364 A1 | | 11/2009 | Koh et al. |
| 2010/0047695 A1 | | 2/2010 | Smart et al. |
| 2010/0183889 A1 | | 7/2010 | Dams et al. |
| 2010/0216035 A1 | | 8/2010 | Iwanaga et al. |
| 2010/0240912 A1 | | 9/2010 | Okamoto et al. |
| 2011/0111308 A1 | | 5/2011 | Halalay et al. |
| 2011/0189395 A1 | | 8/2011 | Padigala et al. |
| 2011/0250503 A1 | | 10/2011 | Wilson et al. |
| 2011/0281173 A1 | | 11/2011 | Singh et al. |
| 2011/0311881 A1 | | 12/2011 | Benicewicz |
| 2012/0082903 A1 | | 4/2012 | Zhang et al. |
| 2012/0141878 A1 | | 6/2012 | Ohashi et al. |
| 2012/0214043 A1 | | 8/2012 | Olschimke et al. |
| 2013/0068408 A1 | | 3/2013 | Tonelli et al. |
| 2013/0248257 A1 | | 9/2013 | Naegel et al. |
| 2013/0337341 A1 | | 12/2013 | Tikhonov et al. |
| 2014/0060859 A1 | | 3/2014 | Kountz et al. |
| 2014/0065461 A1 | | 3/2014 | Kountz et al. |
| 2014/0137766 A1 | | 5/2014 | Chaffins et al. |
| 2014/0245760 A1 | | 9/2014 | Leck et al. |
| 2015/0093654 A1 | | 4/2015 | Galiano |
| 2015/0288028 A1 | | 10/2015 | DeSimone et al. |
| 2016/0028114 A1 | | 1/2016 | Pratt et al. |
| 2016/0043435 A1 | | 2/2016 | DeSimone et al. |
| 2016/0221926 A1 | | 8/2016 | Teran et al. |
| 2016/0226103 A1 | | 8/2016 | Teran et al. |

FOREIGN PATENT DOCUMENTS

| | | |
|---|---|---|
| CN | 101302612 | 11/2008 |
| CN | 102091505 | 6/2011 |
| EP | 0906641 A1 | 4/1999 |
| EP | 1221733 B1 | 12/2006 |
| EP | 2297220 A1 | 3/2011 |
| EP | 2322586 | 5/2011 |
| EP | 2576656 A1 | 4/2013 |
| EP | 2596074 A1 | 5/2013 |
| FR | 2989683 | 10/2013 |
| JP | H3057106 A2 | 3/1991 |
| JP | 2000-327634 A | 11/2000 |
| JP | 2004-272161 | 9/2004 |
| JP | 2010-044958 | 2/2010 |
| JP | 2011-162572 | 8/2011 |
| JP | 2013-069531 | 4/2013 |
| JP | 2013-258076 | 12/2013 |
| JP | 2014-002956 | 1/2014 |
| WO | 9826024 | 6/1992 |
| WO | 95/15588 | 6/1995 |
| WO | 9744842 | 11/1997 |
| WO | 2004-042453 | 5/2004 |
| WO | 2004-068196 | 8/2004 |

(56) References Cited

FOREIGN PATENT DOCUMENTS

| WO | 2005/081646 | 9/2005 |
|----|-------------|--------|
| WO | 2005-081646 | 9/2005 |
| WO | 2006/081646 | 8/2006 |
| WO | 2006-081646 | 8/2006 |
| WO | 2007-044967 | 4/2007 |
| WO | 2009-096570 | 8/2009 |
| WO | 2001-046746 | 6/2010 |
| WO | 2010-096404 | 8/2010 |
| WO | 2010-151639 | 12/2010 |
| WO | 2011-051275 | 5/2011 |
| WO | 2011/051275 | 5/2011 |
| WO | 2011-066830 | 6/2011 |
| WO | 2011/151230 | 12/2011 |
| WO | 2014-025317 | 2/2014 |
| WO | 2014-036360 | 3/2014 |
| WO | 2014-062898 | 4/2014 |
| WO | 2014-204547 | 12/2014 |

OTHER PUBLICATIONS

International Search Report and Written Opinion dated Apr. 11, 2016 issued in PCT Application No. PCT/US2016/016221.
Office Action issued in U.S. Appl. No. 15/012,444, dated Jun. 22, 2016.
Di Lorenzo, Robert, "Perfluoropolyethers: Analytical Method Development for a New Class of Compounds with the Potential to be Long-Lived Environmental Contaminants," Thesis, Master of Science, Graduate Department of Chemistry, University of Toronto, 2012, p. 64.
International Search Report and Written Opinion dated Apr. 11, 2016 in PCT/US2016/016188.
Office Action issued in U.S. Appl. No. 15/012,548, dated Jul. 25, 2016.
Armand et al. "Building Better Batteries," *Nature*, 451:7, 2008, pp. 652-657.
Bongiovanni et al. "Acrylic Polyester Resins Containing Perfluoropolyethers Structures: Synthesis, Characterization, and Photopolymerization" Journal of Applied Polymer Science 2000; 75: 651-659.
Bongiovanni et al. "Perfluoropolyether polymers by UV curing: design, synthesis and Characterization," Polym. lnt., 2012; 61: 65-73.
Bradley, et al., "Evaluation of Boundary-Enhancement Additives for Perfluoropolyethers," *NASA Technical Memorandum 107393*, 1997 Tribology Conference, Sep. 8-12, 1997, p. 24.
Devaux, et al., "Characterizations of nonflammable perfluoropolyether based electrolytes and lithium battery application," (Abstract Only), Conference; Meeting Abstract, 248th ACS National Meeting & Exposition, Aug. 10-14, 2014 (2014), PMSE-541.
Eweka et al. Electrolytes and additives for high efficiency lithium cycling, *Journal of Power Sources*, vol. 65, Issues 1-2, pp. 247-251 (1997) (Abstract Only).
Howell et al. "The preparation of primary poly-hexafluoropropylene oxide halides (poly-HFPO-CF$_2$ X where X=I, Br, CI and F)," *Journal of Fluorine Chemistry*, vol. 125, Issue 10, 2004, pp. 1513-1518.
Hu et al. "Photochemically Cross-Linked Perfluoropolyether-Based Elastomer: Synthesis, Physical Characterization, and Biofouling Evaluation" *Macromolecules*, 2009, vol. 42, pp. 6999-7007.
International Preliminary Report on Patentability Corresponding to International Application No. PCT/US2014/032363 dated Oct. 15, 2015.
International Search Report and Written Opinion, PCT/US2013/065396, dated Jan. 6, 2014.
International Search Report and Written Opinion, PCT/US2014/032363, dated Jan. 12, 2015.
Kasai et al. "Degradation perfluoropolyethers catalyzed by aluminum oxide," *Applied Surface Science*, vol. 51, Issues 3-4,201-211 (1991).
Kim et al. "Electrode Materials for Rechargeable Sodium-Jon Batteries: Potential Alternatives to Current Lithium-Jon Batteries," Adv. Energy Mater., vol. 2, 710-721 (2012).
Kweon et al. "Perfluoropolyether addition Effect on the Properties of Poly(Ethylene Oxide)-Based Solid Polymer Electrolytes," *Korean Chem. Eng. Res.*, vol. 42, No. 6, Dec. 2004, pp. 741-747.
Nair et al. "Methacrylic-based solid polymer electrolyte membranes for lithium-based batteries by a rapid UV-curing process," Reactive and Functional Polymers, vol. 71, Issue 4, pp. 409-416 (2011) (Abstract Only).
Pacansky et al. "Electron Beam Irradiation of Polyperfluoroethers: Experimental Analysis of Main-Chain Degradation," *Chem Mater.*, 5, 486-494 (1993).
Paciorek et al. "Stability of perfluoroalkylethers," *Journal of Fluorine Chemistry*, vol. 67, Issue 2, 1994, 169-175.
Pilati et al. "Poly (E-caprolactone)-Poly (fluoroalkylene oxide)-Poly (E-caprolactone) Block Copolymers. 1. Synthesis and Molecular Characterization" Macromolecules 1999; 32: 6969-6976.
Proudmore et al. "Preparation and Properties of Polyurethane Networks Based on a,w-Difunctional Poly(hexafluoropropylene oxide)," *Journal of Polymer Science: Part A: Polymer Chemistry*, 33, 1615-1625 ( 1995).
Rolland et al. "Solvent-Resistant Photocurable "Liquid Teflon" for Microfluidic Device Fabrication," *J. Am. Chem. Soc.*, 126:2322-2323 (2004).
Russo, et al., "New developments in the synthesis and characterization of phosphate esters of linear (per) fluoropolyether monofunctional and difunctional macromonomers," *Journal of Polymer Science: Part A: Polymer Chemistry*, vol. 43, 2005, 4790-4804.
Smart et al. "Improved performance of lithium-ion cells with the use of fluorinated carbonate-based electrolytes," Journal of Power Sources, 119-121, pp. 359-367, 2003.
Tonelli, Claudio, et al., "Linear perfluoropolyether difunctional oligomers: chemistry, properties and applications," Journal of Fluorine Chemistry, Jun. 1999, 95(1), pp. 51-70.
Wong, Dominica H.C., "Nonflammable perfluoropolyether-based electrolytes for lithium batteries," PNAS, Mar. 4, 2014, vol. 111, No. 9, pp. 3327-3331.
Final Office Action issued in U.S. Appl. No. 15/012,444 , dated Oct. 12, 2016.
Notice of Allowance issued in U.S. Appl. No. 15/012,444 , dated Nov. 2, 2016.
Notice of Allowance issued in U.S. Appl. No. 15/012,548, dated Nov. 21, 2016.
Office Action issued in U.S. Appl. No. 14/436,603, dated Feb. 9, 2017.
Notice of Allowance issued in U.S. Appl. No. 14/436,603, dated May 19, 2017.
Office Action issued in U.S. Appl. No. 14/779,460 , dated Nov. 7, 2016.
Final Office Action issued in U.S. Appl. No. 14/779,460 , dated Apr. 11, 2017.
Notice of Allowance issued in U.S. Appl. No. 14/779,460 , dated Jun. 20, 2017.
European Search Report Corresponding to European Patent Application No. 13847827.6, dated May 19, 2016.
CN Office Action issued in Application No. 201480009932.0, dated Apr. 1, 2017.
Chi-Chang Chen et al., Solid Polymer Electrolytes III: Preparation Characterization, and Ionic Conductivity of New Gelled Polymer Electrolytes Based on Segmented, Perfluoropolyether-Modified Polyurethane, J. Polymer Science: Part A Polymer Chemistry. vol. 40, 2002, pp. 486-495.
Arai et al., Machine Translation of JP 2000-327634 A, Nov. 2000.
Office Action issued in U.S. Appl. No. 15/012,470, dated Apr. 4, 2018.
Office Action issued in U.S. Appl. No. 15/012,497, dated May 31, 2018.
International Preliminary Report on Patentability dated Aug. 17, 2017 issued in PCT Application No. PCT/US16/16221.
International Preliminary Report on Patentability dated Aug. 17, 2017 in PCT/US2016/16188.

\* cited by examiner

FUNCTIONALIZED FLUOROPOLYMERS AND ELECTROLYTE COMPOSITIONS

CROSS-REFERENCE TO RELATED APPLICATIONS

This application claims priority to the following U.S. Provisional patent applications: U.S. Provisional Patent Application No. 62/111,213, filed Feb. 3, 2015, titled "FUNCTIONALIZED FLUOROPOLYMERS AND ELECTROLYTE COMPOSITIONS," U.S. Provisional Patent Application No. 62/130,238, filed Mar. 9, 2015, also titled "FUNCTIONALIZED FLUOROPOLYMERS AND ELECTROLYTE COMPOSITIONS," U.S. Provisional Patent Application No. 62/147,053, filed Apr. 14, 2015 and also titled "FUNCTIONALIZED FLUOROPOLYMERS AND ELECTROLYTE COMPOSITIONS," U.S. Provisional Patent Application No. 62/111,217, filed Feb. 3, 2015, titled "FUNCTIONALIZED FLUOROPOLYMERS," U.S. Provisional Patent Application No. 62/147,047, filed Apr. 14, 2015, also titled "FUNCTIONALIZED FLUOROPOLYMERS," and U.S. Provisional Patent Application No. 62/211,412, filed Aug. 28, 2015, titled "FUNCTIONALIZED PHOSPHORUS CONTAINING FLUOROPOLYMERS." Each of these applications is incorporated by reference herein in its entirety.

BACKGROUND

Lithium-ion (Li-ion) and other alkali metal salt batteries are of great interest as a renewable energy source. Li-ion batteries are the dominant secondary battery for consumer electronics, and have potential for other applications such as energy storage. However, commercially available Li-ion batteries typically include electrolytes having high volatility and flammability. In faulty batteries or batteries exposed to extreme conditions, these electrolytes can cause serious fires. These safety concerns limit the use of Li-ion battery technology in fields that use large-scale batteries including home and grid storage and transportation applications.

SUMMARY

Aspects of the disclosure relate to functionally substituted fluoropolymers. In some embodiments, the functionally substituted fluoropolymers described herein comprise compounds of Formula I or Formula II:

wherein:

$R_f$ is a fluoropolymer (e.g., a perfluoropolyether) backbone;

X is an alkyl, fluoroalkyl, ether, or fluoroether group, wherein 'm' and 'o' may each be independently zero or an integer≥1; and R' and R" are each independently functionally substituted aliphatic, alkyl, aromatic, heterocyclic, amide, carbamate, carbonate, sulfone, phosphate, phosphonate, or nitrile containing groups. In some aspects, the fluoropolymer backbone ('$R_f$') according to Formula I and Formula II is a perfluoropolyether (PFPE). In some aspects, the fluoropolymer backbone ('$R_f$') according to Formula I and Formula II may have a molar mass or number average molecular weight ($M_n$) from about 100 g/mol to 5,000 g/mol, including each integer within the specified range. In some aspects, the functionally substituted perfluoropolyether (i.e., $R_f$—$X_o$—R' or R"—$X_m$—$R_f$—$X_o$—R') according to Formula I and Formula II may have a molar mass or $M_n$ from about 150 g/mol to 5,000 g/mol, including each integer within the specified range.

In some embodiments, the functionally substituted fluoropolymers described herein comprise compounds of Formula III and Formula IV:

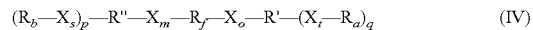

wherein:

$R_f$ is a fluoropolymer (e.g., a perfluoropolyether) backbone;

X is an alkyl, fluoroalkyl, ether, or fluoroether group, wherein 's,' 'm', 'o', and 't' may each be independently zero or an integer≥1; and R' and R", and $R_a$ and $R_b$ are each independently functionally substituted aliphatic, alkyl, aromatic, heterocyclic, amide, carbamate, carbonate, sulfone, phosphate, phosphonate, or nitrile containing groups, wherein 'p' and 'q' may each be an integer≥1. In some aspects, the fluoropolymer backbone ('$R_f$') according to Formula III and Formula IV is a perfluoropolyether. In some aspects, the fluoropolymer backbone ('$R_f$') according to Formula III and Formula IV may have a molar mass or number average molecular weight ($M_n$) from about 100 g/mol to 5,000 g/mol, or 200 g/mol to 5000 kg/mol, including each integer within the specified range. In some aspects, the functionally substituted perfluoropolyether (i.e., $R_f$—$X_o$—R'—$(X_t$—$R_a)_q$ or $(R_b$—$X_s)_p$—R"—$X_m$—$R_f$—$X_o$—R'—$(X_t$—$R_a)_q$ according to Formula III and Formula IV may have a molar mass $M_n$ from about 200 g/mol to 5,000 g/mol, including each integer within the specified range.

One aspect of the disclosure relates to functionally substituted perfluoropolyethers according to Formula VIII:

wherein

R' is an unsubstituted lower alkyl linear carbonate group, X is an alkyl, alkoxy, or ether group, and $R_f$ is a branched or unbranched linear perfluoropolyether having a molar mass of between 200 g/mol and 550 g/mol.

In some embodiments of a functionally substituted perfluoropolyether according to Formula VIII, R' is ethyl carbonate or methyl carbonate. In some embodiments of a functionally substituted perfluoropolyethers according to Formula VIII, $R_f$ has no more than two ether units. In some embodiments, $R_f$ has two at least two ether subunits independently selected from —(CF$_2$CF(CF$_3$)O)—, —(CF(CF$_3$)CF$_2$O)—, —CF(CF$_3$)O—, —(CF$_2$O)—, or —(CF$_2$CF$_2$O)—. In some embodiments, $R_f$ has one or more ether subunits of —(CF$_2$CF$_2$O)—. In some embodiments, $R_f$ has one or more ether subunits of —(CF$_2$CF(CF$_3$)O)—. In some embodiments, $R_f$ has one or more ether subunits of —(CF(CF$_3$)CF$_2$O)—. In some embodiments, $R_f$ has one or more ether subunits of CF(CF$_3$)O. In some embodiments, $R_f$ has one or more ether subunits of —(CF$_2$O)—. In some embodiments, $R_f$ is —CF$_2$OCF$_2$CF$_2$OCF$_3$. In some embodiments, $R_f$ is —CF$_2$OCF$_2$CF$_2$OCF$_2$CF$_2$CF$_3$. In some embodiments, $R_f$ is —CF$_2$OCF$_2$CF$_2$OCF$_2$CF$_2$CF$_2$CF$_3$. In some embodiments, $R_f$ is —CF$_2$OCF$_2$CF$_2$OCF$_2$CF$_2$O$_2$CF$_3$. In some embodiments of a functionally substituted perfluoropolyether according to Formula VIII, $R_f$ is unbranched or if branched, the branch point is at least two chain units away from R'. In the same or other embodiments, X may be $CH_2$, $CH_2CH_2$, $CH_2O$, or $CH_2CH_2O$.

In some embodiments of a functionally substituted perfluoropolyether according to Formula VIII, $R_f$ has a molar mass of between 200 g/mol and 500 g/mol, between 200 g/mol and 450 g/mol, between 200 g/mol and 400 g/mol, between 200 g/mol and 350 g/mol, or between 200 g/mol and 300 g/mol.

In some embodiments of a functionally substituted perfluoropolyether according to Formula VIII, R' is a methyl or ethyl carbonate group, $R_f$ is unbranched or if branched, the branch point is at least two chain units away from R', and X is $CH_2$, $CH_2CH_2$, $CH_2O$, or $CH_2CH_2O$. In some embodiments of a functionally substituted perfluoropolyether according to Formula VIII, R' is a methyl carbonate group, $R_f$ is unbranched or if branched, the branch point is at least two chain units away from R', and X is $CH_2$.

In some embodiments of a functionally substituted perfluoropolyether according to Formula VIII, the functionally substituted perfluoropolyether is according one of structures S5, S6, S7, or S7A depicted below.

Another aspect of the disclosure relates to a functionally substituted perfluoropolyether according to Formula I, above, wherein the functionalized perfluoropolyether exhibits a viscosity of less than 10 cP at 20° C. and 1 atm. In some embodiments, the functionally substituted perfluoropolyether exhibits a viscosity of less than 5 cP at 20° C. and 1 atm. In some embodiments, the functionally substituted perfluoropolyether exhibits a viscosity of less than 3 cP at 20° C. and 1 atm.

Another aspect of the disclosure relates to a non-flammable electrolyte composition comprising: an electrolyte liquid comprising a functionally substituted perfluoropolyether according to Formula VIII and an alkali metal salt. In some embodiments, the functionalized perfluoropolyether comprises about 30% to about 85% of the electrolyte composition. In some embodiments, the functionalized perfluoropolyether comprises about 40% to about 85% of the electrolyte composition. In some embodiments, the functionalized perfluoropolyether comprises is the largest component by weight of the electrolyte solvent.

In some embodiments of the non-flammable electrolyte composition, R' is ethyl carbonate or methyl carbonate. In some embodiments, $R_f$ has no more than two ether units. In some embodiments, $R_f$ has two at least two ether subunits independently selected from —$(CF_2CF(CF_3)O)$—, —$(CF(CF_3)CF_2O)$—, —$CF(CF_3)O$—, —$(CF_2O)$—, or —$(CF_2CF_2O)$—. In some embodiments, $R_f$ has one or more ether subunits of —$(CF_2CF_2O)$—. In some embodiments, $R_f$ has one or more ether subunits of —$(CF_2CF(CF_3)O)$—. In some embodiments, $R_f$ has one or more ether subunits of —$(CF(CF_3)CF_2O)$—. In some embodiments, $R_f$ has one or more ether subunits of —$CF(CF_3)O$. In some embodiments, $R_f$ has one or more ether subunits of —$(CF_2O)$—. In some embodiments, $R_f$ is —$CF_2OCF_2CF_2OCF_3$. In some embodiments, $R_f$ is —$CF_2OCF_2CF_2OCF_2CF_2CF_3$. In some embodiments, $R_f$ is —$CF_2OCF_2CF_2OCF_2CF_2OCF_2CF_2CF_3$. In some embodiments, $R_f$ is —$CF_2OCF_2CF_2OCF_2CF_2O_2CF_3$. In some embodiments, $R_f$ is unbranched or if branched, the branch point is at least two chain units away from R'. In the same or other embodiments, X may be $CH_2$, $CH_2CH_2$, $CH_2O$, or $CH_2CH_2O$.

In some embodiments of the non-flammable electrolyte composition, $R_f$ has a molar mass of between 200 g/mol and 500 g/mol, between 200 g/mol and 450 g/mol, between 200 g/mol and 400 g/mol, between 200 g/mol and 350 g/mol, or between 200 g/mol and 300 g/mol.

In some embodiments of the non-flammable electrolyte composition, R' is a methyl or ethyl carbonate group, $R_f$ is unbranched or if branched, the branch point is at least two chain units away from R', and X is $CH_2$, $CH_2CH_2$, $CH_2O$, or $CH_2CH_2O$. In some embodiments, R' is a methyl carbonate group, $R_f$ is unbranched or if branched, the branch point is at least two chain units away from R', and X is $CH_2$.

In some embodiments of the non-flammable electrolyte composition, the functionally substituted perfluoropolyether is according one of structures S5, S6, S7, or S7A depicted below.

In some embodiments of the non-flammable electrolyte composition, the functionally substituted perfluoropolyether exhibits a viscosity of less than 10 cP at 20° C. and 1 atm. In some embodiments, the functionally substituted perfluoropolyether exhibits a viscosity of less than 5 cP at 20° C. and 1 atm. In some embodiments, the functionally substituted perfluoropolyether exhibits a viscosity of less than 3 cP at 20° C. and 1 atm.

In some embodiments of the non-flammable electrolyte composition, the alkali metal salt comprises a lithium salt or a sodium salt. In some embodiments, the alkali metal salt is a lithium salt comprising $LiPF_6$ or LiTFSI or a mixture thereof. In some embodiments, the electrolyte liquid further comprises further comprising one or more of a conductivity enhancing additive viscosity reducer, a high voltage stabilizer, a wettability additive, or a flame retardant, or a mixture or combination thereof. In some embodiments, the electrolyte liquid further comprises a conductivity enhancing additive selected from ethylene carbonate (EC), propylene carbonate (PC), butylene carbonate (BC), fluoroethylene carbonate, γ-butyrolactone, or a mixture or combination thereof. In some embodiments, the conductivity enhancing additive comprises about 1% to about 40% of the non-flammable electrolyte composition. In some embodiments, the conductivity enhancing additive comprises about 5% to about 40% of the non-flammable electrolyte composition. In some embodiments, the electrolyte liquid comprises a high voltage stabilizer selected from 3-hexylthiophene, adiponitrile, sulfolane, lithium bis(oxalato)borate, γ-butyrolactone, 1,1,2,2-Tetrafluoro-3-(1,1,2,2-tetrafluoroethoxy)-propane, ethyl methyl sulfone, or trimethylboroxine or a mixture or combination thereof. In some embodiments, the electrolyte liquid comprises a wettability additive selected from triphenyl phosphite, dodecyl methyl carbonate, methyl 1-methylpropyl carbonate, methyl 2,2-dimethylpropanoate, or phenyl methyl carbonate or a mixture or combination thereof. In some embodiments, electrolyte liquid comprises a flame retardant additive selected from trimethylphosphate, triethylphosphate, triphenyl phosphate, trifluoroethyl dimethylphosphate, tris(trifluoroethyl)phosphate, or mixture or combination thereof. In some embodiments, the viscosity reducer, high voltage stabilizer, and wettability additive each independently comprise about 0.5-6% of the non-flammable liquid or solid electrolyte composition and the flame retardant comprises about 0.5-20% of the non-flammable liquid or solid electrolyte composition. In some embodiments, the electrolyte liquid further comprises a phosphate or phosphonate-terminated perfluoropolymer.

In some embodiments, the non-flammable electrolyte composition has a flash point greater than 100° C. In some embodiments, the non-flammable electrolyte composition has a flash point greater than 110° C. In some embodiments, the non-flammable electrolyte composition has a flash point greater than 120° C. In some embodiments, the non-flammable electrolyte composition has self-extinguishing time of zero. In some embodiments, the non-flammable electrolyte composition does not ignite when heated to a temperature of about 150° C. and subjected to an ignition source for at least 15 seconds. In some embodiments, the non-flammable electrolyte composition has an ionic conductivity of from 0.01 mS/cm to about 10 mS/cm at 25° C.

Another aspect of the disclosure relates to a non-flammable electrolyte composition comprising: an alkali metal salt; and an electrolyte solvent comprising a functionally substituted perfluoropolyether and one or more C1-C10 cycloalkyl carbonates, wherein the functionally substituted perfluoropolyether comprises between 30 wt % and 95 wt % of the solvent, the one or more C1-C10 cycloalkyl carbonates comprises at least 5 wt % by weight of the solvent, and the functionally substituted perfluoropolyether is the largest component by weight of the solvent, wherein the functionally substituted perfluoropolyether is according to Formula (I) or (II) below:

wherein $R_f$ is a perfluoropolyether backbone;

X is an alkyl, fluoroalkyl, ether, or fluoroether linking group, wherein 'm' and 'o' are each zero or an integer≥1; and R" and R' are each carbonate containing groups, wherein R' is an unsubstituted lower alkyl carbonate group.

In some embodiments, the one or more C1-C10 cycloalkyl carbonates comprises at least 15 wt % by weight of the solvent. In some embodiments, the one or more C1-C10 cycloalkyl carbonates comprises at least 20 wt % by weight of the solvent. In some embodiments, the one or more C1-C10 cycloalkyl carbonates comprises at least 30 wt % by weight of the solvent. In some embodiments, the one or more C1-C10 cycloalkyl carbonates comprises ethylene carbonate (EC), fluoroethylene carbonate (FEC), propylene carbonate (PC), or butylene carbonate (BC).

In some embodiments, the one or more C1-C10 cycloalkyl carbonates comprises ethylene carbonate (EC), with the ethylene carbonate comprises between 5 wt % and 30 wt % of the solvent. In some embodiments, the ethylene carbonate comprises between 10 wt % and 30 wt % of the solvent. In some embodiments, the ethylene carbonate comprises between 15 wt % and 30 wt % of the solvent.

In some embodiments, the electrolyte solvent further comprises further comprising one or more of a conductivity enhancing additive, viscosity reducer, a high voltage stabilizer, a wettability additive, or a flame retardant, or a mixture or combination thereof. In some embodiments, the electrolyte solvent further comprises γ-butyrolactone (GBL). In some embodiment, the electrolyte solvent further comprises a high voltage stabilizer selected from 3-hexylthiophene, adiponitrile, sulfolane, lithium bis(oxalato)borate, γ-butyrolactone, 1,1,2,2-Tetrafluoro-3-(1,1,2,2-tetrafluoroethoxy)-propane, ethyl methyl sulfone, or trimethylboroxine or a mixture or combination thereof. In some embodiments, the electrolyte solvent comprises a wettability additive selected from triphenyl phosphite, dodecyl methyl carbonate, methyl 1-methylpropyl carbonate, methyl 2,2-dimethylpropanoate, or phenyl methyl carbonate or a mixture or combination thereof. In some embodiments, the electrolyte solvent further comprises a wettability additive selected from the group consisting of triphenyl phosphite, dodecyl methyl carbonate, methyl 1-methylpropyl carbonate, methyl 2,2-dimethylpropanoate, or phenyl methyl carbonate or a mixture or combination thereof. In some embodiments, the electrolyte solvent comprises a flame retardant additive selected from trimethylphosphate, triethylphosphate, triphenyl phosphate, trifluoroethyl dimethylphosphate, tris(trifluoroethyl)phosphate, or mixture or combination thereof. In some embodiments, the solvent further comprises a viscosity reducer selected from the group consisting of perfluorotetraglyme, γ-butyrolactone, trimethylphosphate, dimethyl methylphosphonate, difluoromethylacetate, fluoroethylene carbonate (FEC), and vinylene carbonate (VC).

In some embodiments, the electrolyte solvent further comprises a non-carbonate-containing functionally substituted perfluoropolymer ether having one or more aliphatic, alkyl, aromatic, heterocyclo, amide, carbamate, sulfone, phosphate, phosphonate, or nitrile terminal end groups. In some embodiments, the non-carbonate-containing functionally substituted perfluoropolymer ether comprises between 5 wt % and 25 wt % of the solvent.

In some embodiments, the non-flammable electrolyte composition has a flash point greater than 100° C. In some embodiments, the non-flammable electrolyte composition has a flash point greater than 110° C. In some embodiments, the non-flammable electrolyte composition has a flash point greater than 120° C. In some embodiments, the non-flammable electrolyte composition has self-extinguishing time of zero. In some embodiments, the non-flammable electrolyte composition does not ignite when heated to a temperature of about 150° C. and subjected to an ignition source for at least 15 seconds. In some embodiments, the non-flammable electrolyte composition has an ionic conductivity of from 0.01 mS/cm to about 10 mS/cm at 25° C.

In some embodiments of the non-flammable electrolyte composition, the alkali metal salt comprises a lithium salt or a sodium salt. In some embodiments, the alkali metal salt is a lithium salt comprising $LiPF_6$ or LiTFSI or a mixture thereof.

Another aspect of the disclosure is a non-flammable electrolyte composition including an electrolyte liquid having a carbonate-terminated perfluoropolymer and a phosphate-terminated or phosphonate-terminated perfluoropolymer is provided. The electrolyte liquid may further include one or more additives. In some embodiments, the electrolyte composition includes an alkali metal salt. In some embodiments, the liquid is homogenous in the absence of an alkali metal salt at 25° C.

In the same or other embodiments, the weight ratio of the carbonate-terminated perfluoropolymer to the phosphate-terminated or phosphonate-terminated perfluoropolymer is at least 1.2:1. In the same or other embodiments, the weight ratio of the carbonate-terminated perfluoropolymer to the phosphate-terminated or phosphonate-terminated perfluoropolymer is at least 1.4:1. In the same or other embodiments, the weight ratio of the carbonate-terminated perfluoropolymer to the phosphate-terminated or phosphonate-terminated perfluoropolymer is at least 1.6:1.

In the same or other embodiments, together the carbonate-terminated perfluoropolymer and phosphate-terminated or phosphonate-terminated perfluoropolymer constitute at least 50% by weight of the electrolyte liquid. In the same or other embodiments, together the carbonate-terminated perfluoropolymer and phosphate-terminated or phosphonate-terminated perfluoropolymer constitute at least 60% by weight of the electrolyte liquid. In the same or other embodiments, together the carbonate-terminated perfluoropolymer and phosphate-terminated or phosphonate-terminated perfluoropolymer constitute at least 60% by weight of the electrolyte liquid.

In the same or other embodiments, the electrolyte liquid is between 40% and 70% carbonate-terminated perfluoropolymer by weight, between 5% and 25% phosphate-terminated fluoropolymer by weight, the balance of the liquid is the one or more additives, and the balance is between 5% and 25% by weight.

In the some embodiments, the electrolyte liquid includes one or more additives selected from a conductivity enhancing additive, a viscosity reducer, a high voltage stabilizer, a wettability additive, a flame retardant, or a mixture or combination thereof. In some embodiments, the one or more additives includes a conductivity enhancing additive selected from ethylene carbonate (EC), propylene carbonate (PC), butylene carbonate (BC), fluoroethylene carbonate, fluoroethylene carbonate, vinylene carbonate (VC), dimethylvinylene carbonate (DMVC), vinyl ethylene carbonate (VEC), divinylethylene carbonate, phenyl ethylene carbonate, or diphenyethylene carbonate, γ-butyrolactone, or a mixture or combination thereof. In some embodiments, the conductivity enhancing additive constitutes between about 1% to about 30% by weight of the liquid.

In some embodiments, the electrolyte liquid includes one or more cyclo alkyl carbonate additives. The cyclo alkyl carbonate may constitute at least 5% by weight of the liquid, at least 10% by weight of the liquid, at least 15% by weight of the liquid, at least 20% by weight of the liquid, at least 25% by weight of the liquid, or at least 30% by weight of the liquid. Examples of cyclo alkyl carbonates include ethylene carbonate (EC), fluoroethylene carbonate (FEC), propylene carbonate (PC), and butylene carbonate (BC).

In some embodiments, the carbonate-terminated perfluoropolymer is a carbonate-terminated perfluoropolyether. In some embodiments, the carbonate-terminated perfluoropolyether corresponds to one of Formula I and Formula II:

$$R_f - X_o - R' \quad (I)$$

$$R'' - X_m - R_f - X_o - R' \quad (II)$$

wherein $R_f$ is a perfluoropolyether backbone;
X is an alkyl, fluoroalkyl, ether, or fluoroether group, wherein 'm' and 'o' are each zero or an integer≥1;
R' is a carbonate containing group; and
R'' is an aliphatic, alkyl, aromatic, heterocyclic, or carbonate containing group.

In some embodiments, X includes an ether linkage. In some embodiments, X is $CH_2$.

In the same or other embodiments, the carbonate-terminated perfluoropolyether has two terminal carbonate groups. In some embodiments, the carbonate-terminated perfluoropolyether corresponds to a structure S1 to S4 as depicted further below. In some embodiments, the carbonate-terminated perfluoropolyether corresponds to Formula I. In some embodiments, the carbonate-terminated perfluoropolyether corresponds to a structure S5 to S12 as depicted further below.

In some embodiments, the phosphate-terminated or phosphonate-terminated perfluoropolymer is a phosphate-terminated or phosphonate-terminated perfluoropolyether. In some embodiments, the phosphate-terminated or phosphonate-terminated perfluoropolyether comprises Formula I or Formula II:

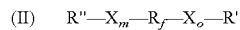

$$R_f - X_o - R' \quad (I)$$

$$(II) \quad R'' - X_m - R_f - X_o - R'$$

wherein $R_f$ is a perfluoropolyether backbone;
X is an alkyl, fluoroalkyl, ether, or fluoroether group, wherein 'm' and 'o' are each independently zero or an integer≥1;
R' is a phosphate or phosphonate containing group; and
R'' is an aliphatic, alkyl, aromatic, heterocyclic, phosphate or phosphonate containing group.

In some embodiments, X includes an ether linkage. In some embodiments, X is $CH_2$. In some embodiments, the phosphate or phosphonate containing group comprises structure S16 or S17 depicted below. In some embodiments, the phosphate-terminated or phosphonate-terminated perfluoropolymer corresponds to one of structures P3-P10 depicted below.

Another aspect of the disclosure relates to a battery comprising an anode; a separator; a cathode; a cathode current collector; and any of the non-flammable electrolyte compositions disclosed herein. In some embodiments, the cathode current collector comprises aluminum. In some embodiments, the non-flammable electrolyte composition comprises LiTFSI. In some embodiments, the non-flammable electrolyte composition prevents or reduces corrosion of the cathode aluminum current collector as compared to a reference battery comprising one or more organic carbonate solvents and LiTFSI, wherein the reference battery does not have a functionally substituted perfluoropolymer. In some embodiments, the battery has an operating temperature of about −30° C. to about 150° C. In some embodiments, the non-flammable electrolyte composition prevents or reduces the flammability of the battery as compared to a reference battery comprising one or more organic carbonate solvents and LiTFSI, wherein the reference battery does not have the functionalized perfluoropolyether does not have a functionally substituted perfluoropolymer.

These and other aspects of the disclosure are discussed further below.

DETAILED DESCRIPTION

Figure 1:
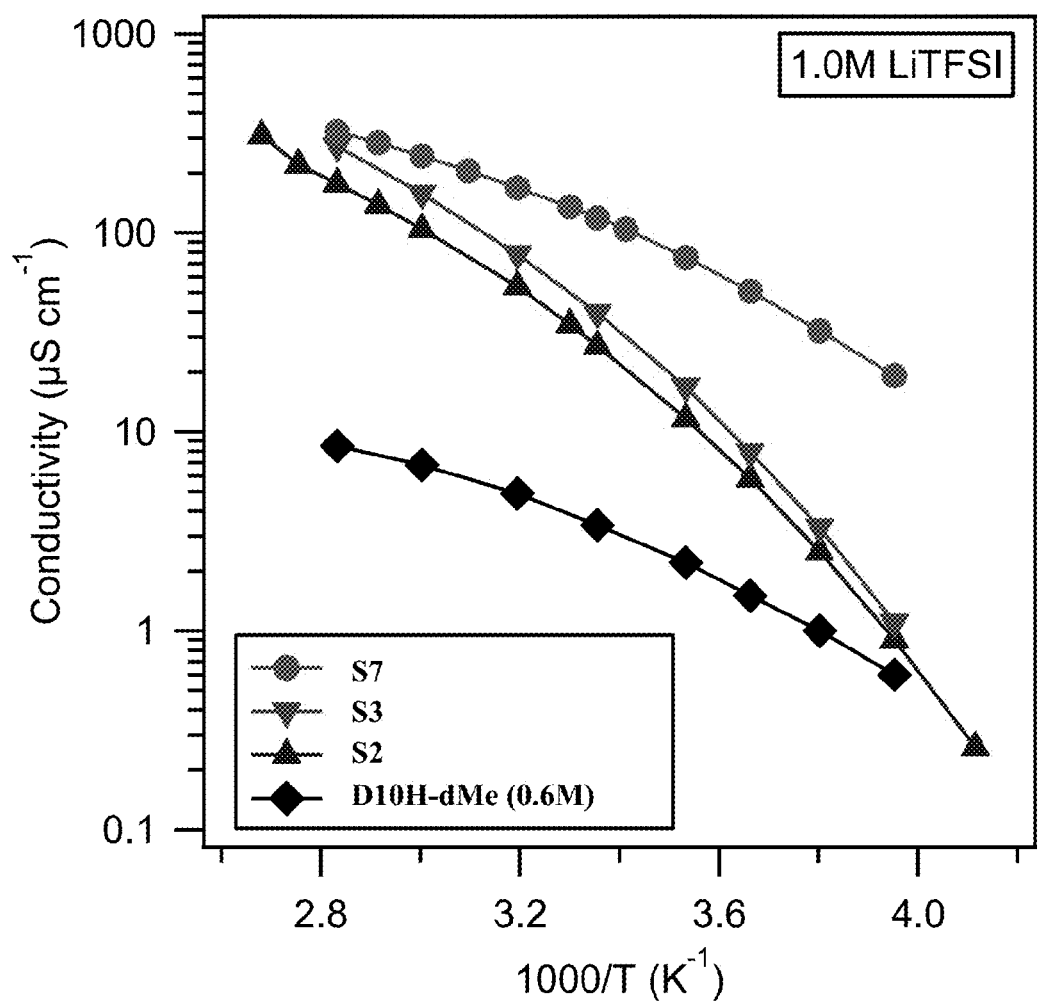
FIG. 1 shows ionic conductivity of PFPE-based electrolyte compositions across a range of temperatures.

The following paragraphs define in more detail the embodiments of the invention described herein. The following embodiments are not meant to limit the invention or narrow the scope thereof, as it will be readily apparent to one of ordinary skill in the art that suitable modifications and adaptations may be made without departing from the scope of the invention, embodiments, or specific aspects described herein.

Described herein are novel functionally substituted fluoropolymers, non-flammable electrolyte compositions, and alkali metal batteries. Also described herein are methods for manufacturing the fluoropolymers and compositions described herein.

For purposes of interpreting this specification, the following terms and definitions will apply and whenever appropriate, terms used in the singular will also include the plural and vice versa. In the event that any definition set forth below conflicts with any document incorporated herein by reference, the definition set forth below shall control.

The term "alkyl" as used herein alone or as part of another group, refers to a straight or branched chain hydrocarbon group, containing any number of carbon atoms, including from 1 to 10 carbon atoms, 1 to 20 carbon atoms, or 1 to 30 or more carbon atoms and that include no double or triple bonds in the main chain. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "lower alkyl" is intended to include both substituted and unsubstituted alkyl or lower alkyl unless otherwise indicated.

The term "cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include cyclopropyl, cyclobutyl, cyclopentyl, cyclohexyl, cycloheptyl, and cyclooctyl. These rings may be optionally substituted with additional substituents as described herein such as halo or lower alkyl. The term "cycloalkyl" is generic and intended to include heterocyclic groups unless specified otherwise, with examples of heteroatoms including oxygen, nitrogen and sulfur The term "alkoxy" as used herein alone or as part of another group, refers to an alkyl or lower alkyl group, as defined herein, appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like. In some aspects, alkoxy groups, when part of a more complex molecule, comprise an alkoxy substituent attached to an alkyl or lower alkyl via an ether linkage.

The term "halo" as used herein refers to any suitable halogen, including —F, —Cl, —Br, and —I.

The term "cyano" as used herein refers to a CN group.

The term "hydroxyl" as used herein refers to an —OH group.

The term "sulfoxyl" as used herein refers to a compound of the formula —S(O)R, where R is any suitable substituent such as alkyl, cycloalkyl, alkenyl, alkynyl or aryl.

The term "carbonate" as used herein alone or as part of another group refers to a —OC(O)OR radical, where R is any suitable substituent such as aryl, alkyl, alkenyl, alkynyl, cycloalkyl or other suitable substituent as described herein.

The term "cyclic carbonate" as used herein refers to a heterocyclic group containing a carbonate.

The term "ester" as used herein alone or as part of another group refers to a —C(O)OR radical, where R is any suitable substituent such as alkyl, cycloalkyl, alkenyl, alkynyl or aryl.

The term "ether" as used herein alone or as part of another group refers to a —COR radical where R is any suitable substituent such as alkyl, cycloalkyl, alkenyl, alkynyl, or aryl.

The term "fluoroalkyl" as used herein alone or as part of another group refers to any alkyl substituted with one or more fluorine atoms.

The term "fluoroether" as used herein alone or as part of another group refers to a —$CF_nOCF_n$R radical, where R is any suitable substituent such as alkyl, cycloalkyl, alkenyl, alkynyl or aryl and n is ≥1.

The term "phosphate" as used herein refers to a —OP(O)$OR_aOR_b$ radical, where $R_a$ and $R_b$ are independently any suitable substituent such as alkyl, cycloalkyl, alkenyl, alkynyl or aryl or a hydrogen atom.

The term "phosphone" as used herein refers to a —P(O)$OR_aOR_b$ radical, where $R_a$ and $R_b$ are independently any suitable substituent such as alkyl, cycloalkyl, alkenyl, alkynyl or aryl or a hydrogen atom.

The term "nitrile" as used herein refers to a —C≡N group.

The term "sulfonate" as used herein refers to a —S(O)(O)OR radical, where R is any suitable substituent such as alkyl, cycloalkyl, alkenyl, alkynyl or aryl.

The term "sulfone" as used herein refers to a —S(O)(O)R radical, where R is any suitable substituent such as alkyl, cycloalkyl, alkenyl, alkynyl or aryl.

The term "fluoropolymer" as used herein alone or as part of another group refers to a branched or unbranched fluorinated chain including two or more C—F bonds. The term "perfluorinated" as used herein refers to a compound or part thereof that includes C—F bonds and no C—H bonds. The term perfluoropolymer as used herein alone or as part of another group refers to a fluorinated chain that includes multiple C—F bonds and no C—H bonds with the exception of C—H bonds that may be present at terminal groups of the chain as described with reference to Formulas V and VI below.

Examples of fluoropolymers include but are not limited to fluoropolyethers, and perfluoropolyethers (i.e., PFPE(s)), poly(perfluoroalkyl acrylate), poly(perfluoroalkyl methacrylate), polytetrafluoroethylene, polychlorotrifluoroethylene, polyvinylidene fluoride, and copolymers of any of the forgoing. See, e.g., U.S. Pat. Nos. 8,361,620; 8,158,728 (DeSimone et al.); and U.S. Pat. No. 7,989,566, each of which is incorporated by reference herein.

It should be noted that in some embodiments the fluoropolymers described herein are significantly smaller than conventional polymers, which contain many repeated subunits.

The term "perfluoropolyether" or PFPE as used herein alone or as part of another group refers to a chain including two or more ether groups and no C—H bonds with the exception of C—H bonds that may be present at terminal groups of the chain as described with reference to Formulas V and VI below. Examples include but are not limited to polymers that include a segment such as difluoromethylene oxide, tetrafluoroethylene oxide, hexafluoropropylene oxide, tetrafluoroethylene oxide-co-difluoromethylene oxide, hexafluoropropylene oxide-co-difluoromethylene oxide, or tetrafluoroethylene oxide-co-hexafluoropropylene oxide-co-difluoromethylene oxide and combinations thereof. See, e.g., U.S. Pat. No. 8,337,986, which is incorporated by reference herein for its teachings thereof. Additional examples include but are not limited to those described in P. Kasai et al., Applied Surface Science 51, 201-211 (1991); J. Pacansky and R. Waltman, Chem. Mater. 5, 486-494 (1993); K. Paciorek and R. Kratzer, Journal of Fluorine Chemistry 67, 169-175 (1994); M. Proudmore et al., Journal of Polymer Science: Part A: Polymer Chemistry, 33, 1615-1625 (1995); J. Howell et al., Journal of Fluorine Chemistry 125, 1513-1518 (2004); and in U.S. Pat. Nos. 8,084,405; 7,294,731; 6,608,138; 5,612,043; 4,745,009; and 4,178,465, each of which are incorporated by reference herein for their teachings thereof.

The term "functionally substituted" as used herein refers to a substituent covalently attached to a parent molecule. In some aspects described herein, the parent molecule is a fluorinated ether or perfluoropolyether as further described herein (e.g., with or without an additional linking group). In some aspects, the substituent comprises one or more polar moieties. In some aspects, the presence of the substituent (e.g., one or more polar moieties) functions to disassociate and coordinate alkali metal salts under certain conditions as further described herein. The term "functionally substituted perfluoropolyether" refers to a compound including a PFPE as described above and one or more functional groups covalently attached to the PFPE. The functional groups may be directly attached to the PFPE or attached to the PFPE by a linking group. The functional groups and the linking groups, if present, may be non-fluorinated, partially fluorinated, or perfluorinated.

The term "number average molecular weight" or "$M_n$" refers to the statistical average molecular weight of all molecules (e.g., perfluoropolyethers) in the sample expressed in units of g/mol. The number average molecular weight may be determined by techniques known in the art, such as gel permeation chromatography (wherein $M_n$ can be calculated based on known standards based on an online detection system such as a refractive index, ultraviolet, or other detector), viscometry, mass spectrometry, or colligative methods (e.g., vapor pressure osmometry, end-group determination, or proton NMR). The number average molecular weight is defined by the equation below, $$M_n = \frac{\sum N_i M_i}{\sum N_i}$$

wherein $M_i$ is the molecular weight of a molecule and $N_i$ is the number of molecules of that molecular weight.

The term "weight average molecular weight" or "$M_w$" refers to the statistical average molecular weight of all molecules (e.g., perfluoropolyethers), taking into account the weight of each molecule in determining its contribution to the molecular weight average, expressed in units of g/mol. The higher the molecular weight of a given molecule, the more that molecule will contribute to the $M_w$ value. The weight average molecular weight may be calculated by techniques known in the art which are sensitive to molecular size, such as static light scattering, small angle neutron scattering, X-ray scattering, and sedimentation velocity. The weight average molecular weight is defined by the equation below, $$M_w = \frac{\sum N_i M_i^2}{\sum N_i M_i}$$

wherein '$M_i$' is the molecular weight of a molecule and '$N_i$' is the number of molecules of that molecular weight.

The term "polydispersity index" or "PDI" refers to the breadth of the molecular weight distribution of a population of molecules (e.g., a population of perfluoropolyether molecules). The polydispersity index is defined by the equation below, $$PDI = \frac{M_w}{M_n}$$

wherein 'PDI' is the ratio of the weight average molecular weight '$M_w$' as described herein to the number average molecular weight '$M_n$' as described herein. All molecules in a population of molecules (e.g., perfluoropolyethers) that is monodisperse have the same molecular weight and that population of molecules has a PDI or $M_w/M_n$ ratio equal to 1.

The term "molar mass" refers to the mass of a chemical compound or group thereof divided by its amount of substance. In the below description, references to weight average molecular weight or number average molecular weight may be alternatively taken to be the molar mass of a single molecule or a population of molecules having a PDI of 1.

The term "non-flammable" as used herein means a compound or solution (e.g., an electrolyte solution) that does not easily ignite, combust, or catch fire.

The term "flame retardant" as used herein refers to a compound that is used to inhibit, suppress, or delay the spread of a flame, fire, or a combustion of one or more materials.

The term "substantially" as used herein means to a great or significant extent, but not completely. In some aspects, substantially means about 90% to 99% or more in the various embodiments described herein, including each integer within the specified range.

The term "about" as used herein refers to any value that is within a variation of up to ±10% of the value modified by the term "about."

The term "at least about" as used herein refers to a minimum numerical range of values (both below and above a given value) that has a variation of up to ±10% of the value modified by the term "about."

As used herein, "a" or "an" means one or more unless otherwise specified.

Terms such as "include," "including," "contain," "containing," "has," or "having" and the like mean "comprising."

The term "or" can be conjunctive or disjunctive.

Functionally Substituted Fluoropolymers

In some embodiments, the functionally substituted fluoropolymers described herein comprise compounds of Formula I and Formula II:

wherein:

$R_f$ is a fluoropolymer (e.g., a perfluoropolyether) backbone;

X is an alkyl, fluoroalkyl, ether, or fluoroether group, wherein 'm' and 'o' may each be independently zero or an integer≥1; and R' and R" are each independently functionally substituted aliphatic, alkyl, aromatic, heterocyclic, amide, carbamate, carbonate, sulfone, phosphate, phosphonate, or nitrile containing groups. In some aspects, the fluoropolymer backbone ('$R_f$') according to Formula I and Formula II is a perfluoropolyether (PFPE). In some aspects, the fluoropolymer backbone ('$R_f$') according to Formula I and Formula II may have a molar mass or number average molecular weight ($M_n$) from about 100 g/mol to 5,000 g/mol, including each integer within the specified range. In some aspects, the functionally substituted perfluoropolyether (i.e., $R_f$—$X_o$—R' or R"—$X_o$—$R_f$—$X_o$—R') according to Formula I and Formula II may have a molar mass or $M_n$ from about 150 g/mol to 5,000 g/mol, including each integer within the specified range.

In some embodiments, the functionally substituted fluoropolymers described herein comprise compounds of Formula III and Formula IV:

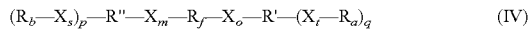

wherein:

$R_f$ is a fluoropolymer (e.g., a perfluoropolyether) backbone;

X is an alkyl, fluoroalkyl, ether, or fluoroether group, wherein 's,' 'm', 'o', and 't' may each be independently zero or an integer≥1; and R' and R", and $R_a$ and $R_b$ are each independently functionally substituted aliphatic, alkyl, aromatic, heterocyclic, amide, carbamate, carbonate, sulfone, phosphate, phosphonate, or nitrile containing groups, wherein 'p' and 'q' may each be an integer≥1. In some aspects, the fluoropolymer backbone ('$R_f$') according to Formula III and Formula IV is a perfluoropolyether. In some aspects, the fluoropolymer backbone ('$R_f$') according to Formula III and Formula IV may have a number average molecular weight ($M_n$) from about 100 g/mol to 5,000 g/mol, or 200 g/mol to 5000 kg/mol, including each integer within the specified range. In some aspects, the functionally substituted perfluoropolyether (i.e., $R_f$—$X_o$—R'—($X_t$—$R_a$)$_q$ or ($R_b$—$X_s$)$_p$—R"—$X_m$—$R_f$—$X_o$—R'—($X_t$—$R_a$)$_q$ according to Formula III and Formula IV may have a $M_n$ from about 200 g/mol to 5,000 g/mol, including each integer within the specified range.

The perfluoropolyether backbone '$R_f$' comprises at least one or more repeating perfluorinated ether units distributed in any order along a polymer chain comprising: —($CF_2$CF($CF_3$)O)—, —(CF($CF_3$)$CF_2$O)—, —CF($CF_3$)O—, —($CF_2$O)—, or —($CF_2CF_2$O)—, wherein the sum of the molecular weights of the perfluorinated ether units has a number average molecular weight from about 100 g/mol to 5,000 g/mol. The repeating perfluorinated ether units may be the same or different units. For example, a repeating unit may be the same (e.g., —CF($CF_3$)O—, —($CF_2$O)—) or different (e.g., —CF($CF_3$)O—, —($CF_2$O)—).

In some embodiments, perfluoropolyether backbone ($R_f$ of formulas I-IV) described herein comprise an exemplary and non-limiting perfluoropolyether backbone of Formulas V and VI:

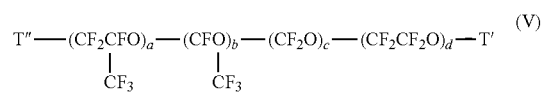

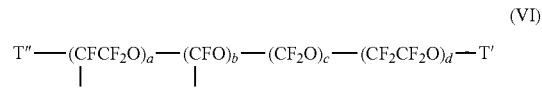

wherein:

'a', 'b', 'c', or 'd' can each independently be zero or an integer≥1 with the proviso that at least one of 'a', 'b', 'c', or 'd' is an integer≥1; wherein the number average molecular weight is from about 150 g/mol to about 5,000 g/mol;

T' is selected from the group consisting of $CF_2$, CF($CF_3$), $CF_2$X, wherein X is selected from the group consisting of: $(CF_2)_n CF_3$, $CH_2$, $(CH_2)_n O$, and O, wherein 'n' is zero or an integer≥1; and T" is selected from the group consisting of: F, $CH_2CF_2$O, $CF_3(CF_2)_n$, $CF_3(CF_2)_n$O, CF($CF_3$), $(CH_2)_n$, $(CH_2)_n$O, and O, wherein is 'n' is zero or an integer≥1.

As described above, for any of a, b, cord that is >1, the multiple —($CF_2$CF($CF_3$)O)—, —(CF($CF_3$)$CF_2$O)—, —CF($CF_3$)O—, —($CF_2$O)—, or —($CF_2CF_2$O)— ether subunits may be distributed in any order along the chain, including sequentially or interspersed with other ether subunits.

Further examples of functionally substituted fluoropolymers and components thereof according to Formulas I-VI are given below with respect to structures S1-S41.

A linear fluoropolymer backbone (e.g., '$R_f$' a perfluoropolyether backbone of Formulas I-IV or Formulas V and VI) as described herein comprises at least two carbon atoms. In one aspect, the linear fluoropolymer backbone may comprise between 2 and 100 carbon atoms, including each integer within the specified range. In another aspect, the linear fluoropolymer backbone may comprise between 2 and 50 carbon atoms, including each integer within the specified range. In another aspect, the linear fluoropolymer backbone comprises between 2 and 20 carbon atoms, including each integer within the specified range. In another aspect, the linear fluoropolymer backbone comprises between 2 and 10 carbon atoms, including each integer within the specified range. In another aspect, the linear fluoropolymer backbone comprises between 2 and 5 carbon atoms, including each integer within the specified range. In another aspect, the linear fluoropolymer backbone comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 or more carbon atoms.

In some embodiments, one or more repeating units of the main linear fluoropolymer backbone (e.g., '$R_f$' a perfluoropolyether backbone of Formulas I-IV or Formulas V and VI) may be further substituted with one or more branching fluorocarbon or fluoroether moieties to form a fluorinated branched chain stemming from one or more carbons of the main fluoropolymer backbone. In one aspect, the one or more branched fluorinated chains stemming independently from one or more carbon atoms of the linear fluoropolymer backbone may comprise between 1 and 5 carbon atoms, including each integer within the specified range. In another aspect, the one or more branched fluorinated chains stemming independently from one or more carbon atoms of the linear fluoropolymer backbone may comprise between 1 and 3 carbon atoms, including each integer within the specified range. In another aspect, the one or more branched fluorinated chains stemming independently from one or more carbon atoms of the linear fluoropolymer backbone may comprise 1 carbon atom.

One embodiment, described herein is functionalized PFPE comprising two linear methyl carbonate groups according to Formula VII:

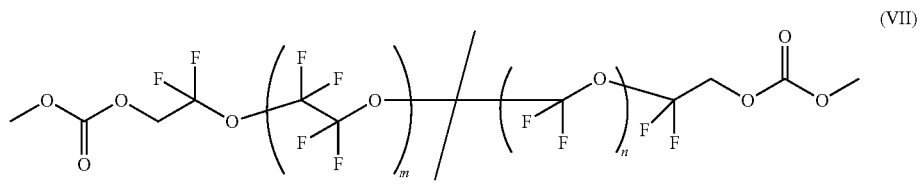

(VII)

wherein m and n are each independently an integer≥1 and the PFPE may have a number average molecular weight ($M_n$) from about 400 g/mol to 5,000 g/mol, including each integer within the specified range. In one aspect, a PFPE according to Formula VII has a number average molecular weight of about 2,000 g/mol.

In some embodiments described herein, the functionalized fluoropolymer (e.g., the perfluoropolyether backbone '$R_f$' covalently attached to one or more groups as described in Formulas I-IV) may have a number average molecular weight ($M_n$) of about 150 g/mol to about 5,000 g/mol, including each integer within the specified range. In some aspects, the functionalized fluoropolymer may have a number average molecular weight of about 150 g/mol to about 2,000 g/mol, including each integer within the specified range. In some aspects, the functionalized fluoropolymer may have a number average molecular weight of about 150 g/mol to about 1,500 g/mol, including each integer within the specified range. In some aspects, the functionalized fluoropolymer may have a number average molecular weight of about 150 g/mol to about 1,000 g/mol, including each integer within the specified range. In some aspects, the functionalized fluoropolymer may have a number average molecular weight of about 150 g/mol to about 500 g/mol, including each integer within the specified range. In some aspects, the functionalized fluoropolymer may have a number average molecular weight of about 150 g/mol to about 300 g/mol, including each integer within the specified range.

In some aspects, the functionalized fluoropolymer may have a number average molecular weight of at least about 150 g/mol, at least about 200 g/mol, at least about 250 g/mol, at least about 300 g/mol, at least about 350 g/mol, at least about 400 g/mol, at least about 450 g/mol, at least about 500 g/mol, at least about 550 g/mol, at least about 600 g/mol, at least about 650 g/mol, at least about 700 g/mol, at least about 750 g/mol, at least about 800 g/mol, at least about 850 g/mol, at least about 900 g/mol, at least about 950 g/mol, at least about 1,000 g/mol, at least about 1,100 g/mol, at least about 1,200 g/mol, at least about 1,300 g/mol, at least about 1,400 g/mol, at least about 1,500 g/mol, at least about 1,600 g/mol, at least about 1,700 g/mol, at least about 1,800 g/mol, at least about 1,900 g/mol, at least about 2,000 g/mol, at least about 2,250 g/mol, at least about 2,500 g/mol, at least about 2,750 g/mol, at least about 3,000 g/mol, at least about 3,250 g/mol, at least about 3,500 g/mol, at least about 3,750 g/mol, at least about 4,000 g/mol, at least about 4,250 g/mol, at least about 4,500 g/mol, at least about 4,750 g/mol, or at least about 5,000 g/mol.

In some embodiments described herein, the functionalized fluoropolymer (i.e., the perfluoropolyether backbone '$R_f$' covalently attached to one or more groups as defined in Formulas I-IV) may have a weight average molecular weight ($M_w$) of about 150 g/mol to about 5,000 g/mol, including each integer within the specified range. In some aspects, the functionalized fluoropolymer may have a weight average molecular weight of about 150 g/mol to about 2,000 g/mol, including each integer within the specified range. In some aspects, the functionalized fluoropolymer may have a weight average molecular weight of about 150 g/mol to about 1,500 g/mol, including each integer within the specified range. In some aspects, the functionalized fluoropolymer may have a weight average molecular weight of about 150 g/mol to about 1,000 g/mol, including each integer within the specified range. In some aspects, the functionalized fluoropolymer may have a weight average molecular weight of about 150 g/mol to about 500 g/mol, including each integer within the specified range. In some aspects, the functionalized fluoropolymer may have a weight average molecular weight of about 150 g/mol to about 300 g/mol, including each integer within the specified range. In some aspects, the functionalized fluoropolymer may have a weight average molecular weight of at least about 150 g/mol, at least about 200 g/mol, at least about 250 g/mol, at least about 300 g/mol, at least about 350 g/mol, at least about 400 g/mol, at least about 450 g/mol, at least about 500 g/mol, at least about 550 g/mol, at least about 600 g/mol, at least about 650 g/mol, at least about 700 g/mol, at least about 750 g/mol, at least about 800 g/mol, at least about 850 g/mol, at least about 900 g/mol, at least about 950 g/mol, at least about 1,000 g/mol, at least about 1,100 g/mol, at least about 1,200 g/mol, at least about 1,300 g/mol, at least about 1,400 g/mol, at least about 1,500 g/mol, at least about 1,600 g/mol, at least about 1,700 g/mol, at least about 1,800 g/mol, at least about 1,900 g/mol, at least about 2,000 g/mol, at least about 2,250 g/mol, at least about 2,500 g/mol, at least about 2,750 g/mol, at least about 3,000 g/mol, at least about 3,250 g/mol, at least about 3,500 g/mol, at least about 3,750 g/mol, at least about 4,000 g/mol, at least about 4,250 g/mol, at least about 4,500 g/mol, at least about 4,750 g/mol, at least about 5,000 g/mol, at least about 5,500 g/mol, at least about 6,000 g/mol, at least about 6,500 g/mol, at least about 7,000 g/mol, at least about 7,500 g/mol, at least about 8,000 g/mol, at least about 8,500 g/mol, at least about 9,000 g/mol, at least about 9,500 g/mol, or at least about 10,000 g/mol.

In some embodiments described herein, the functionalized fluoropolymer (e.g., the perfluoropolyether backbone '$R_f$' covalently attached to one or more groups as defined in Formulas I-II) may have a polydispersity index (PDI) of about 1 to about 20. In some aspects, the functionalized fluoropolymer may have a polydispersity index of about 1 to about 10. In some aspects, the functionalized fluoropolymer may have a polydispersity index of about 1 to about 5. In some aspects, the functionalized fluoropolymer may have a polydispersity index of about 1 to about 2. In some aspects, the functionalized fluoropolymer may have a polydispersity index of about 1 to about 1.5. In some aspects, the functionalized fluoropolymer may have a polydispersity index of about 1 to about 1.25. In some aspects, the functionalized fluoropolymer may have a polydispersity index of about 1 to about 1.1. In some aspects, the functionalized fluoropolymer may have a polydispersity index of about 1, less than about 1.05, less than about 1.1, less than about 1.15, less than about 1.2, less than about 1.25, less than about 1.5, less than about 1.75, less than about 2, less than about 2.25, less than about 2.5, less than about 2.75, less than about 3, less than about 3.5, less than about 4, less than about 4.5, less than about 5, less than about 6, less than about 7, less than about 8, less than about 9, less than about 10, less than about 11, less than about 12, less than about 13, less than about 14, less than about 15, less than about 16, less than about 17, less than about 18, less than about 19, or less than about 20.

In some embodiments described herein, the fluoropolymers described herein (e.g., a functionalized perfluoropolyether) comprises a linear carbonate terminated PFPE as shown in structure S13 discussed further below. For example, the linear carbonate terminated PFPE includes a methyl carbonate structure as shown in structure SA1. SA1 is an example of R' or R" according to some embodiments of Formulas I-II above.

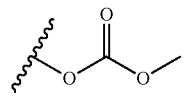

SA1

In further examples, in some embodiments, described herein is a functionalized PFPE comprising two linear methyl carbonate groups according to any of structures S1-S4.

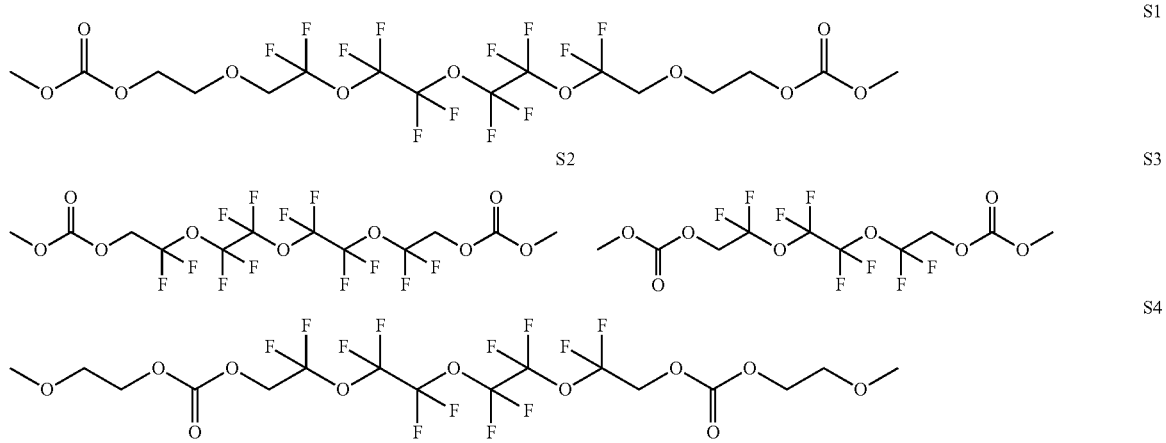

Another embodiment described herein is a functionalized PFPE comprising one linear methyl carbonate group according to structures S5-S7.

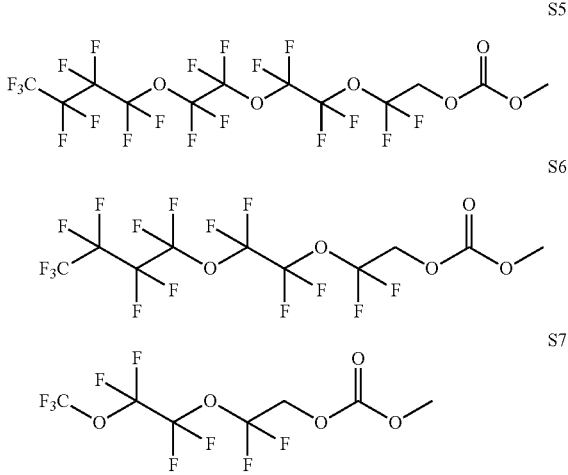

Another embodiment described herein the functionalized PFPE's may include lower alkyl carbonate groups. For example, the methyl carbonate group of any of structures S5-S7 may be replaced by any of an ethyl carbonate, a propyl carbonate, or a butyl carbonate group. In one example, a functionalized PFPE comprising one linear ethyl carbonate group according to structure S7A is provided:

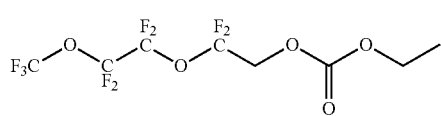 [SMILES: CCOC(=O)OCC(F)(F)OC(F)(F)C(F)(F)OC(F)(F)F]
S7A

Another embodiment, described herein is a functionalized PFPE comprising one cyclic carbonate group according to structures S8-S9.

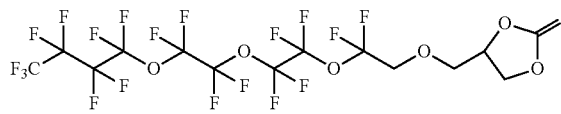
S8

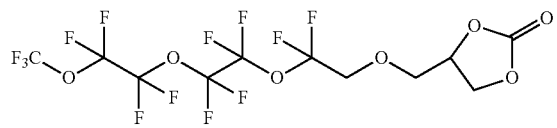
S9

Another embodiment, described herein is a functionalized PFPE comprising a linear carbonate group linked to a cyclic carbonate group according to structure S10.

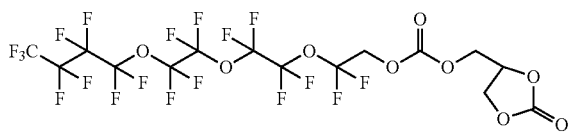
S10

In another embodiment described herein, the functionalized PFPE may comprise a linear carbonate structure or cyclic carbonate structure as shown in structures S11A, S11B, S12, wherein one or more carbon atoms of the main linear PFPE backbone comprise a branched —$CF_3$ moiety.

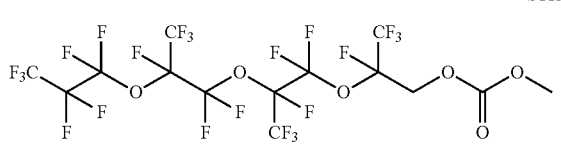
S11A

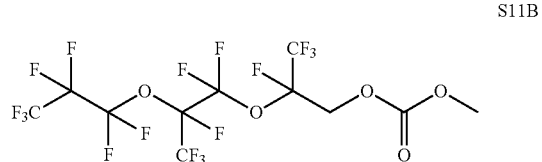
S11B

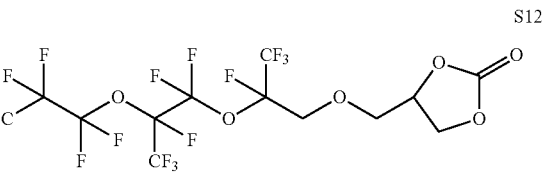
S12

In some embodiments, the fluoropolymers described herein (e.g., a functionalized perfluoropolyether) may comprise one or more carbamate, carbonate, sulfone, phosphate, phosphonate, or nitrile containing groups. In some embodiments, these groups may comprise any one of or a combination of any one of the moieties represented by structures S13-S23. In some embodiments, these groups maybe selected from the group consisting of the moieties represented by structures S13-S23. In some aspects, Y', Y", and Y'" represent an additional aliphatic, alkyl, aromatic, heterocyclic, amide, carbamate, carbonate, sulfone, phosphate, phosphonate or nitrile containing groups as given in Formulas I-IV above. In some embodiments, S13-S23 are examples of R' or R" according to some embodiments of Formulas I-IV above. In some aspects, the moieties represented by these structures are covalently attached to the fluoropolymer backbone as indicated by Formulas I-IV above.

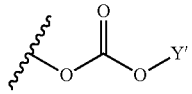
S13

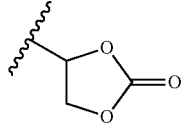
S14

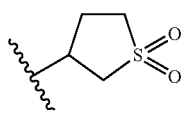
S15

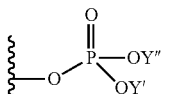
S16

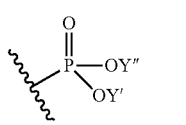
S17

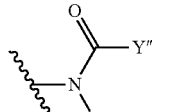
S18

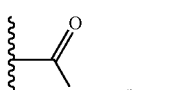
S19

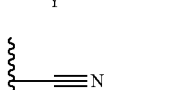
S20

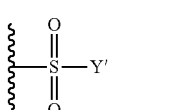
S21

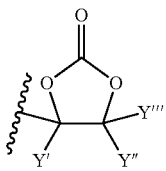

S22

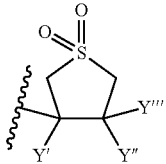

S23

In some embodiments described herein, the fluoropolymers described herein (e.g., a functionalized perfluoropolyether) may comprise between 1 and 10 of any one of or a combination of any one of the moieties represented by structures S13-S23, including each integer within the specified range. In some aspects, these structures are covalently attached to the perfluoropolyether backbone as indicated by Formulas I-IV above. In some other aspects, the fluoropolymers described herein (e.g., a functionalized perfluoropolyether) may comprise at least 1, at least 2, at least 3, or at least 4 or more of any one of or a combination of any one of structures S13-S23 covalently attached to the fluoropolymer backbone as indicated by Formulas I-IV above.

In some embodiments described herein, the fluoropolymers described herein (e.g., a functionalized perfluoropolyether) may comprise any one of the structures selected from the group consisting of structures S24-S37 shown below, wherein X is an alkyl, fluoroalkyl, ether, or fluoroether group as defined in Formulas I-IV.

In one embodiment, the functionalized PFPE may comprise an ether linked cyclic carbonate structure as shown in structures S24-S27,

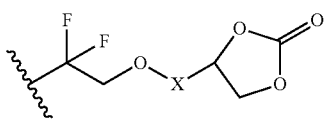

S24

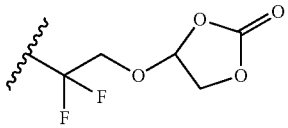

S25

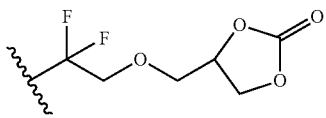

S26

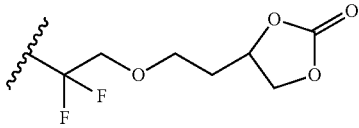

S27 wherein X is an alkyl, fluoroalkyl, ether, or fluoroether group. For example, in S25, the cyclic carbonate is directly attached to the PFPE without an X group, and in S26, X is an alkyl group consisting of $CH_2$, and in S27, X is an alkyl group consisting of $CH_2CH_2$.

In another embodiment, the functionalized PFPE may comprise a linear carbonate structure as shown in structures S28 and S29, wherein X is an alkyl, fluoroalkyl, ether, or fluoroether group as defined in Formulas I-IV and Y' is an aliphatic, alkyl, aromatic, heterocyclic, amide, carbamate, carbonate, sulfone, phosphate, phosphonate or nitrile containing group. For example, in S29, X is an alkyl ethyl group and Y' is a methyl group, resulting in a linear methyl carbonate structure.

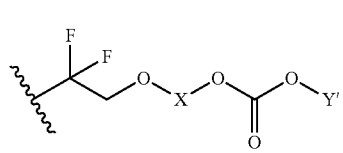

S28

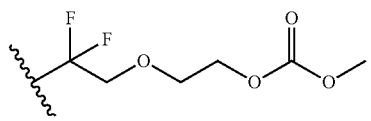

S29

In another embodiment, the functionalized PFPE may comprise a cyclic sulfone structure as show in structure S30. In some aspects, the cyclic sulfone may be multiply substituted as shown in structure S30, wherein X is an alkyl, fluoroalkyl, ether, or fluoroether group as defined in Formulas I-IV and Y', Y'', and Y''' are each independently aliphatic, alkyl, aromatic, heterocyclic, amide, carbamate, carbonate, sulfone, phosphate, phosphonate or nitrile containing groups.

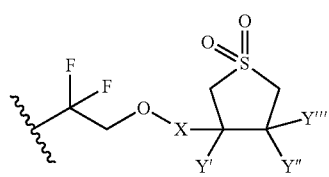

S30

In another embodiment, the functionalized PFPE may comprise a linear sulfone structure as shown in structures S31 and S32, wherein X is an alkyl, fluoroalkyl, ether, or fluoroether group as defined in Formulas I-IV and wherein Y' is an aliphatic, alkyl, aromatic, heterocyclic, amide, carbamate, carbonate, sulfone, phosphate, phosphonate or nitrile containing group. For example, in S32, X is an ethyl group and Y' is an ethyl group.

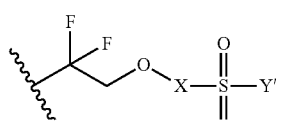

S31

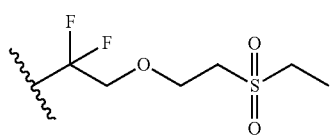

S32

In another embodiment, the functionalized PFPE may comprise a phosphonate structure or phosphate structure as show in structures S33 and S34. In some aspects, the phosphonate or phosphate structure may be multiply substituted, wherein X is an alkyl, fluoroalkyl, ether, or fluoroether group as defined in Formulas I-IV and Y' and Y" are each independently an aliphatic, alkyl, aromatic, heterocyclic, amide, carbamate, carbonate, sulfone, phosphate, phosphonate or nitrile containing group.

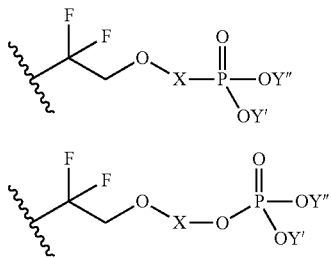

Further discussion and examples of functionalized PFPE's including phosphate or phosphate groups is provided below.

In another embodiment, the functionalized PFPE may comprise an amide group as shown in structures S35 and S36, wherein X is an alkyl, fluoroalkyl, ether, or fluoroether group as defined in Formulas I-IV and Y' and Y" are each independently an aliphatic, alkyl, aromatic, heterocyclic, amide, carbamate, carbonate, sulfone, phosphate, phosphonate or nitrile containing group. In one aspect, X of structure 35 connects to the amide group through a carbon (e.g., (R—C)—N). In one aspect, X of structure 31 may connect through a carbon atom (e.g., (R—C)—C(O)) or through an oxygen atom (e.g., forming a carbamate structure (R—O)—C(O)).

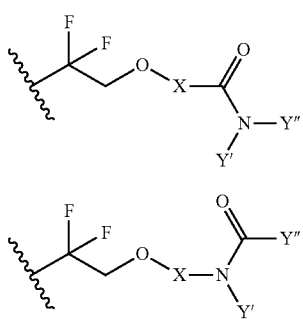

In another embodiment, the functionalized PFPE may comprise a nitrile group as shown in structure S37, wherein X is an alkyl, fluoroalkyl, ether, or fluoroether group as defined in Formulas I-IV.

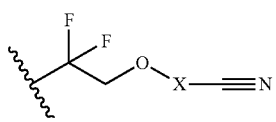

According to various embodiments, the functionally substituted PFPEs described herein do not include carbon-carbon double or triple bonds, with carbon-carbon single bonds having greater stability as may be desirable for an electrolyte solvent.

In some embodiments described herein, the functionally substituted PFPEs described herein serve to coordinate alkali metal ions and exhibit chemical and thermal stability. The relative high fluorine content reduces or prevents combustion. Further, in some embodiments, the functionally substituted PFPEs coordinate alkali metal ions, allowing for the dissolution of salts, and the conduction of ions in electrolyte mixtures as further described herein. In some aspects, the use of an ether linkage between the PFPE backbone and any one or more of an aliphatic, alkyl, aromatic, heterocyclic, amide, carbamate, carbonate, sulfone, phosphate, phosphonate, or nitrile containing groups as shown by Formulas I-IV or any one or more of structures S13-S23 allows for increased flexibility and conformational freedom of these groups. In some aspects, this increased flexibility may enhance the functionalized perfluoropolyether mediated coordination of alkali metal ions as further described herein.

Flammability of an electrolyte compound or mixture thereof may be characterized by flash points (FPs) or self-extinguishing times (SETs). The flash point of a liquid is the lowest temperature at which vapors of the fluid ignite and is measured by subjecting the liquid to an ignition source as temperature is raised. The flash point may be tested by using an instrument, such as the Koehler rapid flash tester, or an equivalent, wherein a composition is subjected to an ignition source for at least about 1 second to about 30 seconds at a temperature range of from about −30° C. to about 300° C. A liquid that does not ignite at any temperature does not have a flash point. It is understood that references to a liquid having a flash point above a certain temperature include liquids that do not have a flash point. The SET of a sample is the time that an ignited sample keeps burning. In some cases, a liquid may have a flash point but a SET of zero, indicating that the material flashes but does not sustain a flame once the ignition source is removed.

Flammability may also be characterized by a wick test in which a wick soaked in the electrolyte compound or mixture and ignited with a Bunsen burner for at least 5 seconds. If there is no ignition, the flame is reapplied for at least 10 seconds. The speed at which the flame propagates is measured. The test may be performed with the wick in a horizontal or vertical position.

Heavily fluorinated compounds are inherently non-flammable. This is distinct from conventional electrolyte flame retardant additives such as phosphates, which retard combustion by scavenging free radicals, thereby terminating radical chain reactions of gas-phase combustion.

In some aspects, the functionally substituted fluoropolymer or fluoropolymer backbone $R_f$ that is covalently attached to one or more groups as described in Formulas I-IV is relatively small, with the size characterized by one or more of molar mass, $M_n$, $M_w$, or main chain length. In some aspects, a functionalized PFPE as described in Formulas I-VI has $R_f$ such that the functionalized PFPE is conductive and inherently non-flammable or has low flammability, as measured by a high or non-existent flash point and a SET of zero. Conductivity of some functionally substituted PFPE's drops sharply as the $R_f$ size increases, however, if $R_f$ (and the F:H ratio) is too small, the compound may be flammable.

PFPEs having $R_f$ in the ranges as described below were found to have low or no flammability, and good conductivity.

In some aspects, a perfluoropolyether backbone $R_f$ covalently attached to one or more groups as described in Formulas I-IV has a molar mass or number average molecular weight of between about 150 g/mol to 500 g/mol. In some aspects, a perfluoropolyether backbone $R_f$ covalently attached to one or more groups as described in Formulas I-IV has a molar mass or number average molecular weight of between about 200 g/mol to 500 g/mol. In some aspects, a perfluoropolyether backbone $R_f$ covalently attached to one or more groups as described in Formulas I-IV has a molar mass or number average molecular weight of between about 200 g/mol to about 400 g/mol, including each integer within the specified range.

In some aspects, a perfluoropolyether backbone $R_f$ covalently attached to one or more groups as described in Formulas I-IV comprises one or more perfluorinated ether units distributed in any order along a polymer chain comprising: —(CF$_2$CF(CF$_3$)O)—, —(CF(CF$_3$)CF$_2$O)—, —CF(CF$_3$)O—, —(CF$_2$O)—, or —(CF$_2$CF$_2$O)—, wherein the sum of the molar masses or molecular weights of the perfluorinated ether units has a molar mass or number average molecular weight from about 100 g/mol to 450 g/mol, including each integer within the specified range. In some aspects, the sum of the molar masses or molecular weights of the perfluorinated ether units has a molar mass or number average molecular weight from about 100 g/mol to 400 g/mol, including each integer within the specified range. In some aspects, the sum of the molar masses or molecular weights of the perfluorinated ether units has a molar mass or number average molecular weight from about 100 g/mol to 350 g/mol including each integer within the specified range. In some aspects, the sum of the molar masses or molecular weights of the perfluorinated ether units has a molar mass or number average molecular weight from about 100 g/mol to 300 g/mol, including each integer within the specified range.

In some embodiments, $R_f$ includes a linear fluoropolymer backbone (e.g., a PFPE backbone) having between 3 and 9 carbon atoms including each integer in the specified range. For example, the linear fluoropolymer backbone may have between 3 and 8 carbon atoms, or between 3 and 7 carbon atoms, or between 3 and 6 carbon atoms, or between 3 and 5 atoms. In another aspect the linear fluoropolymer backbone comprises 3, 4, 5, 6, 7, 8, or 9 carbon atoms. If branched, the linear fluoropolymer may additionally incorporate one or more branched fluorinated chains stemming independently from one or more carbon atoms of the linear fluoropolymer backbone as described above, each of which branched chains may have between 1 and 5 carbon atoms, including each integer within the specified range.

In some embodiments, a PFPE backbone $R_f$ covalently attached to one or more groups as described in Formulas I-IV is unbranched, or if branched, has no branch points within two molecules (along the $R_f$—X—R' or R"—$X_m$—$R_f$—X—R' chain) of the functional group on R' or R" of Formulas I and II. In some embodiments, a branched PFPE backbone $R_f$ has no branch points within three molecules, four molecules, five molecules, or six molecules of the functional group on R' or R" of Formulas I and II. As an example, the branch point C—CF$_3$ in the structure S38 below is five molecules away from the carbonate functional group.

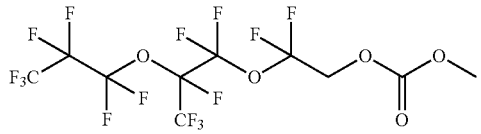

In some embodiments, a branched PFPE backbone has no more than two branches or no more than one branch.

In some embodiments, R' and R" as disclosed in Formulas I and II have a lower alkyl end group, e.g., R' or R" may be methyl carbonate, ethyl carbonate, propyl carbonate, methyl phosphate, ethyl phosphate, etc. In some embodiments, R' and R" as disclosed in Formulas I and II are non-fluorinated. Fluorine is electron withdrawing such that the presence of fluorine on R' or R" can reduce conductivity. Further, fluorine close to the carbonate may be unstable. If R' or R" is partially fluorinated, any F may be at least two or three molecules away from the carbonate or other functional group of R' or R".

In some embodiments, the functionally substituted fluoropolymers disclosed herein are mono-functional. It has been found that for some embodiments of relatively small molecular weight functionally substituted fluoropolymers, mono-functional functionally substituted fluoropolymers may have significantly higher conductivities than their di-functional counterparts, despite having fewer ion coordinating groups. Without being bound by a particular theory, it is believed that the increase in conductivity is due to the sharp decrease in viscosity observed for the mono-functional fluoropolymers. For relatively large functionally substituted fluoropolymers (e.g., MW of 1000 g/mol and above), the difference between mono-functional and di-functional functionally substituted fluoropolymers is not expected to be as significant.

In some embodiments, the functionally substituted fluoropolymers according to Formula (I) comprise compounds of Formula (VIII):

R'—X—$R_f$ wherein (VIII)

R' is a lower alkyl linear carbonate group, X is alkyl, fluoroalkyl, alkoxy, fluoroalkoxy, ether, or fluoroether group, and $R_f$ is a branched or unbranched linear perfluoropolyether having a $M_n$ of between 200 g/mol and 550 g/mol.

In some embodiments, R' of Formula VIII is a non-fluorinated lower alkyl linear carbonate group. In some embodiments, R' is an unsubstituted lower alkyl linear carbonate group. In some embodiments, R' is an unbranched lower alkyl linear carbonate group. In some embodiments, R' is ethyl carbonate or methyl carbonate. In some embodiments, R' is methyl carbonate according to structure SA1, above.

In some embodiments, X is a non-fluorinated alkyl, alkoxy, or ether group. In some embodiments, X is an unsubstituted alkyl, alkoxy, or ether group. In some embodiments, X is an unsubstituted alkyl, alkoxy, or ether group having between 1 and 3 carbon atoms. In some embodiments, X is an unsubstituted alkyl, group having between 1 and 3 carbon atoms. In some embodiments X is CH$_2$, CH$_2$CH$_2$, CH$_2$O, or CH$_2$CH$_2$O. In some embodiments, X is CH$_2$.

In some embodiments, $R_f$ has between 3 and 9 carbon atoms. In some embodiments, $R_f$ has between 3 and 9 carbon atoms, or between 3 and 8 carbon atoms, or between 3 and 7 carbon atoms, or between 3 and 6 carbon atoms, or between 3 and 5 carbon atoms.

In some embodiments, $R_f$ has a $M_n$ of between 200 g/mol and 500 g/mol. In some embodiments, $R_f$ has a $M_n$ of between 200 g/mol and 450 g/mol. In some embodiments, $R_f$ has a $M_n$ of between 200 g/mol and 400 g/mol. In some embodiments, $R_f$ has a $M_n$ of between 200 g/mol and 350 g/mol. In some embodiments, $R_f$ has a $M_n$ of between 200 g/mol and 300 g/mol.

In some embodiments, a compound of Formula VIII has a $M_n$ of between 250 g/mol and 650 g/mol. In some embodiments, a compound of Formula VIII has a $M_n$ of between 250 g/mol and 600 g/mol. In some embodiments, a compound of Formula VIII has a $M_n$ of between 250 g/mol and 550 g/mol. In some embodiments, a compound of Formula VIII has a $M_n$ of between 250 g/mol and 500 g/mol. In some embodiments, a compound of Formula VIII has a $M_n$ of between 250 g/mol and 450 g/mol. In some embodiments, a compound of Formula VIII has a $M_n$ of between 250 g/mol and 400 g/mol. In some embodiments, a compound of Formula VIII has a $M_n$ of between 250 g/mol and 350 g/mol.

In some embodiments, $R_f$ comprises one or more perfluorinated ether units distributed in any order along a chain comprising: —(CF$_2$CF(CF$_3$)O)—, —(CF(CF$_3$)CF$_2$O)—, —CF(CF$_3$)O—, —(CF$_2$O)—, or —(CF$_2$CF$_2$O)—.

In some embodiments, $R_f$ is terminated with a CF$_2$CF$_2$CF$_2$CF$_3$ group or a CF$_3$ group.

Example $R_f$ groups of Formula VIII include those of structures S39-S41:

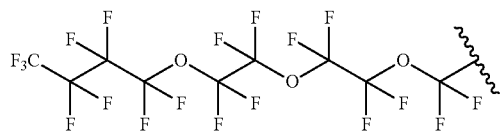

S39

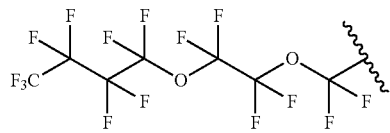

S40

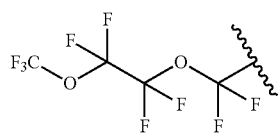

S41

Examples of substituted PFPE's according to Formula VIII are structures S5-S7 above.

The functionally substituted fluoropolymers according to Formula VIII may have the following characteristics: low viscosity, non-flammability, accessible functional groups to dissociate and coordinate alkali metal salts, relatively high ionic conductivity, and stability. In some embodiments, the viscosity is less than about 10 cP at 20° C. and 1 atm, or less than about 6 cP at 20° C. and 1 atm, or less than about 5 cP at 20° C. and 1 atm, or less than about 4 cP at 20° C. and 1 atm, or less than about 3 cP at 20° C. and 1 atm. Low viscosity is due to mono-functionality and relatively low molecular weights of the functionally substituted PFPE's of Formula VIII.

In some embodiments, the conductivity of a functionally substituted fluoropolymer according to Formula VIII in 1.0M LiTFSI is at least 0.02 mS/cm at 25° C., at least 0.03 mS/cm at 25° C., at least 0.04 mS/cm at 25° C., at least 0.05 mS/cm at 25° C., at least 0.06 mS/cm at 25° C., at least 0.07 mS/cm at 25° C., at least 0.08 mS/cm at 25° C., at least 0.09 mS/cm at 25° C., at least 0.10 mS/cm at 25° C., at least 0.11 mS/cm at 25° C., at least 0.12 mS/cm at 25° C.

In some embodiments, R' is an unsubstituted linear carbonate group, which may contribute to high conductivity, with the relatively low molecular weights of the PFPE's of Formula VIII also contributing to relatively high conductivity. In some embodiments, a lack of large groups on either side of the carbonate group of R' of Formula VIII may contribute to relatively high conductivity. In some embodiments, relatively small $R_f$ groups may contribute to relatively high conductivity.

In some embodiments, the substituted fluoropolymers according to Formula VIII have a flash point and SET of zero in addition to having the viscosities and/or conductivities described above.

Any of the perfluoropolymers disclosed above with respect to Formulas I-VIII may be modified to form partially fluorinated fluoropolymers. For example, one or more CF$_3$ or CF$_2$ groups of the PFPE's disclosed herein may be modified to form CHF$_2$, CH$_2$F, CHF, or CH$_2$, with the distribution of hydrogen along the $R_f$ chain managed to avoid flammability. Such partially fluorinated fluoropolymers may be formed from the PFPE or by any other known synthetic route.

Electrolyte Compositions

Some embodiments described herein are electrolyte compositions comprising a functionally substituted fluoropolymer as described herein. In some aspects, the electrolyte composition comprises a mixture or combination of functionally substituted fluoropolymers described herein. In some aspects, the electrolyte composition is useful in an alkali-metal ion battery. In some aspects, the addition of electrolyte additives may improve battery performance, facilitate the generation of a solid electrolyte interface (i.e., an SEI) on electrode surfaces (e.g., on a graphite based anode), enhance thermal stability, protect cathodes from dissolution and overcharging, and enhance ionic conductivity.

In some embodiments, the electrolyte compositions described herein comprise an alkali metal salt and a functional end group substituted PFPE as described herein. In some aspects, the electrolyte composition may optionally further comprise one or more conductivity enhancing additives, one or more SEI additives, one or more viscosity reducers, one or more high voltage stabilizers, and one or more wettability additives. In some aspects, the electrolyte compositions described herein comprise the composition shown in Table 1.

TABLE 1

Example Fluoropolymer Electrolyte System

| Component | Exemplary Components | Composition Range (%) |
|---|---|---|
| Alkali-metal salt | Lithium salt (e.g., LiPF$_6$ or LiTFSI), Sodium salt, Potassium salt, etc. | 8-35 |
| Func. Subst. PFPE or mixture of Func. Subst. PFPE's | PFPE-carbonate (e.g., PFPE-methyl carbonate) or PFPE-carbonate and PFPE-phosphate | 30-85 |
| Conductivity enhancing additive(s) | Ethylene carbonate, fluoroethylene carbonate, trispentafluorophenyl borane, lithium bis(oxalato)borate, γ-butyrolactone, etc. | 1-40 |
| Opt. SEI additive(s) | Ethylene carbonate, vinyl carbonate, vinyl ethylene carbonate, lithium bis(oxalato)borate, lithium difluoro(oxalate)borate, fluoroethylene carbonate, etc. | 0.5-6 |
| Opt. Viscosity reducer(s) | perfluorotetraglyme, γ-butyrolactone, trimethylphosphate, dimethyl methylphosphonate, difluoromethylacetate, fluoroethylene carbonate (FEC), vinylene carbonate (VC), etc. | 0.5-6 |
| Opt. High voltage stabilizer(s) | 3-hexylthiophene, adiponitrile, sulfolane, lithium bis(oxalato)borate, γ-butyrolactone, 1,1,2,2-tetrafluoro-3-(1,1,2,2-tetrafluoroethoxy)-propane, ethyl methyl sulfone, trimethylboroxine, etc. | 0.5-6 |
| Wettability additive | Non-ionic or ionic surfactant, fluorosurfactant, etc. | 0.5-6 |
| Opt. Flame retardant | trimethylphosphate, triethylphosphate, triphenylphosphate, trifluoroethyl dimethylphosphate, tris(trifluoroethyl)phosphate, etc. | 0.5-20 |

Electrolyte compositions described herein can be prepared by any suitable technique, such as mixing a functionally substituted fluoropolymer (e.g., a functionalized perfluoropolyether) as described above after polymerization thereof with an alkali metal ion salt, and optionally other ingredients, as described below, in accordance with known techniques. In the alternative, electrolyte compositions can be prepared by including some or all of the composition ingredients in combination with the reactants for the preparation of the fluoropolymer prior to reacting the same.

When other ingredients are included in the homogeneous solvent system, in general, the functionally substituted fluoropolymer (e.g., a functionalized perfluoropolyether) is included in the solvent system in a weight ratio to all other ingredients (e.g., polyether, polyether carbonates) of from 40:60, 50:50, 60:40, or 70:30, up to 90:10, 95:5, or 99:1, or more.

In some embodiments, the electrolyte compositions comprise an SEI additive. In some aspects, the addition of SEI additives prevents the reduction of the PFPE electrolytes described herein and increases the full cycling of batteries. In some aspects, films of SEI additives maybe be coated onto graphite surfaces prior to any cycling to form an insoluble preliminary film. In some aspects, SEI additives form films on graphite surfaces during the first initial charging when the electrolyte compositions described herein are used in a battery. Suitable SEI additives comprise polymerizable monomers, and reduction-type additives.

Non-limiting examples include allyl ethyl carbonate, vinyl acetate, divinyl adipate, acrylic acid nitrile, 2-vinyl pyridine, maleic anhydride, methyl cinnamate, phosphonate, 2-cyanofuran, or additional vinyl-silane-based compounds or a mixture or combination thereof. In addition, sulfur-based reductive type additives may be used including sulfur dioxide, poly sulfide containing compounds, or cyclic alkyl sulfites (e.g., ethylene sulfite, propylene sulfite, and aryl sulfites). Other reductive additives including nitrates and nitrite containing saturated or unsaturated hydrocarbon compounds, halogenated ethylene carbonate (e.g., fluoroethylene carbonate), halogenated lactones (e.g., α-bromo-γ-butyrolactone), and methyl chloroformate. Additional examples may include a cyclic carbonate having a C═C unsaturated bond, such as vinylene carbonate (VC), dimethylvinylene carbonate (DMVC), vinylethylene carbonate (VEC), divinylethylene carbonate, phenyl ethylene carbonate, diphenyl ethylene carbonate, or any combination thereof. In addition, SEI formation maybe be initiated by use of carbon dioxide as a reactant with ethylene carbonate and propylene carbonate electrolytes. Additional SEI forming additives may include carboxyl phenols, aromatic esters, aromatic anhydrides (e.g., catechol carbonate), succinimides (e.g., benzyloxy carbonyloxy succinimide), aromatic isocyanate compounds, boron based compounds, such as trimethoxyboroxine, trimethylboroxin, bis(oxalato)borate (e.g., lithium bis(oxalato) borate (LiBOB)), difluoro(oxalate)borate (e.g., lithium difluoro(oxalate)borate (LiDFOB)), or tris(pentafluorophenyl) borane, or mixture or combination thereof. Further examples of SEI additives are taught by U.S. Patent App. Pub No. 2012/0082903, which is incorporated by reference herein.

In some embodiments, the electrolyte compositions comprise one or more flame retardants. Non-limiting examples of flame retardants may include trimethylphosphate (TMP), triethylphosphate (TEP), Triphenyl phosphate (TPP), trifluoroethyl dimethylphosphate, tris(trifluoroethyl)phosphate (TFP) or mixture or combination thereof. While the electrolyte solutions described herein are non-flammable, in some embodiments described herein, one or more flame retardants may be used to prevent, suppress, or delay the combustion of adjacent non-electrolyte materials (e.g., surrounding battery materials).

In some embodiments, the electrolyte compositions comprise a wetting agent. In some aspects, the wetting agent comprises an ionic or non-ionic surfactant or low-molecular weight cyclic alkyl compound (e.g., cyclohexane) or an aromatic compound. Other fluoro containing surfactants may be used. See, U.S. Pat. No. 6,960,410, which is incorporated by reference herein for its teachings thereof.

In some embodiments, the electrolyte compositions comprise a non-aqueous conductivity enhancing additive. It is thought that the presence of even small amounts of a polar conductivity enhancer aids in the disassociation of alkali metal salts and increases the total conductivity of electrolyte mixtures. This may reduce ohmic drop from a decreased bulk resistance in the electrochemical cells of batteries and enable cycling at higher densities. The conductivity enhancing additive may include, for example, one or more cyclic carbonates, acyclic carbonates, fluorocarbonates, cyclic esters, linear esters, cyclic ethers, alkyl ethers, nitriles, sulfones, sulfolanes, siloxanes, and/or sultones.

Cyclic carbonates that are suitable include ethylene carbonate (EC), propylene carbonate (PC), butylene carbonate (BC), fluoroethylene carbonate and the like. Suitable cyclic esters include, for example γ-butyrolactone (GBL), α-methyl-γ-butyrolactone, γ-valerolactone; or any combination thereof. Examples of a cyclic ester having a C=C unsaturated bond include furanone, 3-methyl-2(5H)-furanone, α-angelicalactone, or any combinations thereof. Cyclic ethers include tetrahydrofuran, 2-methyltetrahydrofuran, tetrahydropyran and the like. Alkyl ethers include dimethoxyethane, diethoxyethane and the like. Nitriles include mononitriles, such as acetonitrile and propionitrile, dinitriles such as glutaronitrile, and their derivatives. Sulfones include symmetric sulfones such as dimethyl sulfone, diethyl sulfone and the like, asymmetric sulfones such as ethyl methyl sulfone, propyl methyl sulfone and the like, and derivatives of such sulfones, especially fluorinated derivatives thereof. Sulfolanes include tetramethylene sulfolane and the like.

Other conductivity enhancing carbonates, which may be used, include fluorine containing carbonates, including difluoroethylene carbonate (DFEC), bis(trifluoroethyl) carbonate, bis(pentafluoropropyl) carbonate, trifluoroethyl methyl carbonate, pentafluoroethyl methyl carbonate, heptafluoropropyl methyl carbonate, perfluorobutyl methyl carbonate, trifluoroethyl ethyl carbonate, pentafluoroethyl ethyl carbonate, heptafluoropropyl ethyl carbonate, perfluorobutyl ethyl carbonate, or any combination thereof.

Other conductivity enhancing additives, which may be used, include fluorinated oligomers, dimethoxyethane, triethylene glycol dimethyl ether (i.e., triglyme), tetraethyleneglycol, dimethyl ether (DME), polyethylene glycols, bromo γ-butyrolactone, fluoro γ-butyrolactone, chloroethylene carbonate, ethylene sulfite, propylene sulfite, phenylvinylene carbonate, catechol carbonate, vinyl acetate, dimethyl sulfite, tetraglyme, a crown ether, or any combination thereof.

In some embodiments, the electrolyte composition comprises one or more alkali metal ion salts. Alkali metal ion salts that can be used in the embodiments described herein are also known or will be apparent to those skilled in the art. Any suitable salt can be used, including lithium salts and sodium salts, and potassium salts, that is, salts containing lithium or sodium or potassium as a cation with a suitable anion. Any suitable salt may be used, examples of which include, but are not limited to, boron tetrafluoride, (oxalate) borate, difluoro(oxalate)borate, phosphorus hexafluoride, alkyl sulfonate, fluoroalkyl sulfonate, aryl sulfonate, bis (alkylsulfonyl)amide, perchlorate, bis(fluoroalkylsulfonyl) amide, bis(arylsulfonyl)amide, alkyl, fluorophosphate, hexafluorophosphate, hexafluoroarsenate, (fluoroalkylsulfonyl)(fluoroalkylcarbonyl)amide, halide, nitrate, nitrite, sulfate, hydrogen sulfate, alkyl sulfate, aryl sulfate, carbonate, triflate, bicarbonate, carboxylate, phosphate, hydrogen phosphate, dihydrogen phosphate, hypochlorite, an anionic site of a cation-exchange resin, and a mixture of any two or more thereof. For further examples, see, Zhang et al., U.S. Patent Application Publication No. 2012/0082903, which is incorporated by reference herein for its teachings thereof. In some aspects, the alkali metal ion salt is a lithium salt.

In some embodiments, the electrolyte compositions described herein comprise lithium hexafluorophosphate (i.e., $LiPF_6$). The use of $LiPF_6$ in lithium ion batteries has demonstrated a balance of important properties as an electrolyte salt, particularly in alkali metal batteries. $LiPF_6$ can demonstrate high conductivity and forms stable interfaces and can function to passivate the aluminum surface of aluminum-based current collectors.

Although common and useful in many applications, the use of $LiPF_6$ may be limited in certain applications, e.g., under high temperature conditions. For example, at high temperatures (e.g., >60° C.), the hydrolysis of the $PF_6$ salt anion can occur leading to the formation of HF, which is toxic and has deleterious effects on the electrolyte solvent and the electrodes active materials. Hydrolysis of the $PF_6$ salt anion can further lead to the evolution of gaseous $PF_5$ and side reactions with ethylene carbonate to form toxic fluoroethanol derivatives. Therefore, the development of electrolyte compositions that enable the use of salts having high thermal and electrochemical stability, while retaining high levels of conductivity is needed. Accordingly, in certain embodiments, it may be useful to employ alternative salts in addition to or in replacement of $LiPF_6$.

Alkali metal sulfonimide salts are exemplary materials that can be employed for such purposes. Such materials can, in some embodiments, demonstrate sufficient safety at high temperatures, high ionic conductivity, and sufficient thermal and electrochemical stability. Such properties can, in some embodiments, render these materials suitable electrolyte salts for use in lithium ion batteries. Although not intended to be limiting, it is believed that, for example, the enhanced high temperature safety, high ionic conductivity, and enhanced thermal and electrochemical stability exhibited by one particular such salt, e.g., bis(trifluoromethanesulfonyl) imide $LiN(SO_2CF_3)_2$ (LiTFSI), is attributable to the TFSI anion, which demonstrates high thermal stability and decreased hydrolysis from stable C—F bonds.

As further described herein, stable lithium salts include any lithium salt, which exhibits low levels of hydrolysis, thermostability, high ionic conductivity, and electrochemical stability in electrolyte compositions and in the alkali metal batteries described herein.

Suitable non-limiting sulfonimide salts comprise lithium, sodium, potassium, magnesium, or calcium metal sulfonimide salts, e.g., comprising lithium bis(trifluoromethanesulfonyl)imide $LiN(SO_2CF_3)_2$ (LiTFSI), lithium bis(fluorosulfonyl)imide (LiFSI), $LiN(FSO_2)_2$, lithium trifluoromethanesulfonate $Li(CF_3)SO_3$ (LiTF), lithium (trifluoromethylsulfonyl)(nonafluorobutanesulfonyl)imide $LiN(SO_2CF_3)(SO_2C_4F_9)$, lithium (fluorosulfonyl)(nonafluorobutanesulfonyl)imide $LiN(SO_2F)(SO_2C_4F_9)$, lithium (nonafluoro butan-2-one sulfonyl)(trifluoromethylsulfonyl) imide $LiN(SO_2C_2F_4OC_2F_5)(SO_2CF_3)$, and lithium (nonafluoro butan-2-one sulfonyl)(fluorosulfonyl)imide $LiN(SO_2C_2F_4OC_2F_5)(SO_2F)$.

In some embodiments, the electrolyte compositions described herein enable the use of lithium sulfonimide salts (e.g., LiTFSI) by minimizing aluminum current collector corrosion. In some aspects, the electrolyte compositions described herein comprise LiTFSI. In some aspects, the electrolyte compositions described herein comprise a mixture of $LiPF_6$ and LiTFSI.

In some embodiments lithium sulfonamide salts (e.g., LiTFSI) may help facilitate the dissolution of highly polar conductivity enhancing additives, such as ethylene carbonate when used in combination with the perfluoropolyethers described herein. Without being bound by any theory, it is thought that lithium sulfonamide salts (e.g., LiTFSI) substantially disassociate, which increases the ionic strength of the electrolyte composition allowing for a substantial dissolution of polar compounds, such as ethylene carbonate.

In some further aspects, the use of a lithium sulfonimide salt (e.g., LiTFSI) may suppress side reactions on the electrode/electrolyte interfaces and enable the use of electrolytes at elevated temperatures greater than 60° C. leading to increased energy/power characteristics and use in high temperature applications of the alkali metal batteries described herein.

In some embodiments, the electrolyte compositions described herein comprise a viscosity reducer. Suitable, non-limiting examples of viscosity reducers include perfluorotetraglyme, γ-butyrolactone, trimethylphosphate, dimethyl methylphosphonate, difluoromethylacetate, fluoroethylene carbonate (FEC), vinylene carbonate (VC), etc.

In some embodiments, the electrolyte compositions described herein comprise a high voltage stabilizer. Suitable non-limiting examples of high voltage stabilizers include 3-hexylthiophene, adiponitrile, sulfolane, lithium bis(oxalato)borate, γ-butyrolactone, 1,1,2,2-Tetrafluoro-3-(1,1,2,2-tetrafluoroethoxy)-propane, ethyl methyl sulfone, and trimethylboroxine.

In some embodiments, additional ingredients comprising PFPEs and poly(ethylene oxide) (PEO) may be included in the electrolyte compositions described herein in any suitable amount, such in a weight ratio (PFPE:PEO) range of between (on one end of the range) 40:60, 50:50, or 60:40, up to (on the other end of the range) 80:20, 90:10 or 95:5. In some aspects, the PFPE and PEO may be cross-linked. See, PCT International Application Publication No. WO2014062898, which is incorporated by reference in its entirety herein.

In some embodiments, the functionally substituted PFPEs described herein comprise about 30% to about 85% of the electrolyte compositions described herein. In some aspects, the functionally substituted PFPEs described herein comprise about 40% to about 50% of the electrolyte compositions described herein. In some aspects, the functionally substituted PFPEs described herein comprise about 50% to about 60% of the electrolyte compositions described herein. In some aspects, the functionally substituted PFPEs described herein comprise about 60% to about 70% of the electrolyte compositions described herein. In some aspects, the functionally substituted PFPEs described herein comprise about 70% to about 85% or more of the electrolyte compositions described herein. In some aspects, the functionally substituted PFPEs described herein comprise about 35%, about 40%, about 45%, about 50%, about 55%, about 60%, about 65%, about 70%, about 75%, about 80%, about 85%, or about 90% of the electrolyte compositions described herein.

In some embodiments, the alkali-metal salts described herein comprise about 8% to about 35% of the electrolyte compositions described herein. In some aspects, the functionally substituted PFPEs described herein comprise about 20% to about 30% of the electrolyte compositions described herein. In some aspects the alkali-metal salts described herein comprise about 10%, about 15%, about 20%, about 25%, about 30%, about 35%, or about 40% of the electrolyte compositions described herein.

In some embodiments, the optional one or more conductivity enhancing additives described herein comprise about 1% to about 40% of the electrolyte compositions described herein. In some aspects, the optional one or more conductivity enhancing additives described herein comprise about 10% to about 20% of the electrolyte compositions described herein. In some aspects, the optional one or more conductivity enhancing additives described herein comprise about 20% to about 30% of the electrolyte compositions described herein. In some aspects, the optional one or more conductivity enhancing additives described herein comprise about 30% to about 40% of the electrolyte compositions described herein. In some aspects, the optional one or more conductivity enhancing additives described herein comprise about 1%, about 2%, about 3%, about 4%, about 5%, about 10%, about 15%, about 20%, about 25%, about 30%, about 35%, about 40%, or about 45% of the electrolyte compositions described herein.

In some embodiments, the optional one or more SEI additives described herein comprise about 0.5% to about 6% of the electrolyte compositions described herein. In some aspects, the optional one or more SEI additives described herein comprise about 0.5%, about 1%, about 2%, about 3%, about 4%, about 5%, or about 6% of the electrolyte compositions described herein.

In some embodiments, the optional one or more viscosity reducers described herein comprise about 0.5% to about 6% of the electrolyte compositions described herein. In some aspects, the optional one or more viscosity reducers described herein comprise about 0.5%, about 1%, about 2%, about 3%, about 4%, about 5%, or about 6% of the electrolyte compositions described herein.

In some embodiments, the optional one or more high voltage stabilizers described herein comprise about 0.5% to about 6% of the electrolyte compositions described herein. In some aspects, the optional one or more high voltage stabilizers described herein comprise about 0.5%, about 1%, about 2%, about 3%, about 4%, about 5%, or about 6% of the electrolyte compositions described herein.

In some embodiments, the optional one or more wettability additives described herein comprise about 0.5% to about 6% of the electrolyte compositions described herein. In some aspects, the optional one or more wettability additives described herein comprise about 0.5%, about 1%, about 2%, about 3%, about 4%, about 5%, or about 6% of the electrolyte compositions described herein.

Flammability of an electrolytic compound or mixture thereof may be characterized by flash points (FPs) or self-extinguishing times (SETs). The flash point of a liquid is the lowest temperature at which vapors of the fluid ignite and is measured by subjecting the liquid to an ignition source as temperature is raised. The flash point may be tested by using an instrument, such as the Koehler rapid flash tester, or an equivalent, wherein a composition is subjected to an ignition source for at least about 1 second to about 30 seconds at a temperature range of from about −30° C. to about 300° C. The SET of a sample is the time that an ignited sample keeps burning. In some cases, a liquid may have a flash point but a SET of zero, indicating that the material flashes but does not burn once the ignition source is removed.

Heavily fluorinated compounds are inherently non-flammable. This is distinct from conventional electrolyte flame retardant additives such as phosphates, which retard combustion by scavenging free radicals, thereby terminating radical chain reactions of gas-phase combustion.

As described above, in some embodiments, the electrolytes disclosed herein have a fluoropolymer or mixture of fluoropolymers as the largest component by weight. This is distinct from fluorinated additives present in small amounts with non-fluorinated hydrocarbon or other conventional solvent as the largest component of the solvent.

In some aspects, the electrolyte compositions described herein comprise the solvent system shown in Table 2. It should be noted that the solvent systems in Table 2 do not include salts or optional SEI additives, which may be added to the solvent to form an electrolyte.

In some embodiments, the solvent system includes between 0.5% and 25% by weight of γ-butyrolactone. In some embodiments, the solvent system includes between 0.5% and 20% by weight of γ-butyrolactone. In some embodiments, the solvent system includes between 0.5% and 15% of γ-butyrolactone. In some embodiments, the solvent system includes between 0.5% and 10% by weight of γ-butyrolactone. In some embodiments, the solvent system includes between 5% and 15% of γ-butyrolactone.

In some embodiments, the solvent system includes between 0.5% and 25% of trimethylphosphate. In some embodiments, the solvent system includes between 0.5% and 20% of trimethylphosphate. In some embodiments, the solvent system includes between 0.5% and 15% of trimethylphosphate. In some embodiments, the solvent system includes between 0.5% and 10% of trimethylphosphate. In

TABLE 2

Example Fluoropolymer Electrolyte Solvent System

| Component | Example Components | Composition Ranges (wt %) |
|---|---|---|
| Func. Subst. PFPE or mixture of Func. Subst. PFPE's | PFPE-carbonate (e.g., PFPE-methyl carbonate) or PFPE-carbonate and PFPE phosphate | 40-100<br>50-90<br>55-85<br>60-70 |
| C1-C10 cycloalkyl carbonate or mixture thereof | Ethylene carbonate, propylene carbonate | 0-40<br>5-30<br>10-30<br>15-30 |
| Opt. Conductivity Additive(s), Opt. Viscosity reducer(s), Opt. High voltage stabilizer(s), Opt. Wettability additive(s), Opt. Flame retardants | Trispentafluorophenyl borane, lithium bis(oxalato)borate, γ-butyrolactone, perfluorotetraglyme, dimethyl methylphosphonate, difluoromethylacetate, fluoroethylene carbonate (FEC), vinylene carbonate (VC), 3-hexylthiophene, adiponitrile, sulfolane, lithium bis(oxalato)borate, γ-butyrolactone, 1,1,2,2-tetrafluoro-3-(1,1,2,2-tetrafluoroethoxy)-propane, ethyl methyl sulfone, trimethylboroxine, non-ionic or ionic surfactant, fluorosurfactant, trimethylphosphate, triethylphosphate, triphenyl phosphate, etc. | 0.5-35<br>0.5-25<br>0.5-6 |

In some embodiments, the electrolyte solvent includes a functionally substituted PFPE as the largest component by weight and also includes a significant amount of a C1-C10 cyclo alkyl carbonate. For example, the electrolyte solvent may include at least 5% by weight, or greater than 5% by weight, of C1-C10 cyclo alkyl carbonate such as ethylene carbonate (EC), propylene carbonate (PC), fluoroethylene carbonate (FEC), and the like. In some embodiments, the electrolyte includes at least 5% of a C1-C10 or C1-C5 cycloalkyl carbonate. In some embodiments, the electrolyte includes at least 10% of a C1-C10 or C1-C5 cycloalkyl carbonate. In some embodiments, the electrolyte includes at least 15% of a C1-C10 or C1-C5 cycloalkyl carbonate. In some embodiments, the electrolyte includes at least 20% of a C1-C10 or C1-C5 cycloalkyl carbonate. In addition to being a conductivity enhancer, the cyclo alkyl carbonate may aid formation of a stable SEI layer.

While EC and other cyclo alkyl carbonates have relatively high FPs, the SETs are also high; once ignited, EC will burn until it is consumed. It was unexpectedly found a mixture including a functionally substituted perfluoropolyether or mixture thereof as the largest component is is inflammable even with a significant amount of a C1-C10 cycloalkyl carbonate. For example, for a 8:2 mixture of a linear PFPE:EC, no FP was measured and the SET was zero.

some embodiments, the solvent system includes between 5% and 15% of trimethylphosphate.

In some embodiments, the electrolyte composition is in accordance with the examples shown in Table 3.

TABLE 3

Example Fluoropolymer Electrolyte Solvent System

| Component | Example Components | Composition Range (wt %) |
|---|---|---|
| Lithium salt | LiPF$_6$, LiTSI | 10-35<br>10-20 |
| SEI additive | Fluoroethylene carbonate, etc. | 0-5<br>5-30<br>10-30 |
| Solvent | Mixture of func. subst. PFPE, C1-cycloalkyl carbonate, and optional additives (see Table 2) | remainder |

As noted above, the PFPE's disclosed herein may have no or very high flash points. The electrolyte solvent including additives will generally have a flash point due to the presence of the additives. In some embodiments, the electrolyte compositions described herein are non-flammable with a flash point greater than about 50° C. to about 275° C. In some aspects, the electrolyte compositions described herein are non-flammable with a flashpoint greater than about 50° C., greater than about 60° C., greater than about 70° C., greater than about 80° C., greater than about 90° C., greater than about 100° C., greater than about 110° C., greater than about 120° C., greater than about 130° C., greater than about 140° C., greater than about 150° C., greater than about 160° C., greater than about 170° C., greater than about 180° C., greater than about 190° C., greater than about 200° C., greater than about 200° C., greater than about 210° C., greater than about 220° C., greater than about 230° C., greater than about 240° C., greater than about 250° C., greater than about 260° C., greater than about 270° C., or greater than about 280° C. or greater. It is understood that an electrolyte composition having a flash point greater than a certain temperature includes compositions that do not ignite and have no flash point.

In addition to the flash points described above, the electrolyte compositions may have SETs of less than one second, or zero. It is understood that an electrolyte composition having a SET of less than one second include electrolyte compositions that have an SET of zero.

The electrolyte compositions may additionally or alternatively be characterized as having "no sustained flame" on wick test performed as described in the Examples.

In some embodiments, each component of the electrolyte mixture that is present at greater than 5% of the solvent has a flash point of at least 80° C., or at least 90° C., or at least 100° C. The corresponding electrolyte mixture may have a flash point of greater than 100° C., or greater than 110° C., or greater than 120° C., along with an SET of zero.

In some embodiments, the non-flammable liquid or solid electrolyte compositions described herein have an ionic conductivity of from 0.01 mS/cm to about 10 mS/cm at 25° C. In some embodiments, the non-flammable liquid or solid electrolyte compositions described herein have an ionic conductivity of from 0.01 mS/cm to about 5 mS/cm at 25° C. In some embodiments, the non-flammable liquid or solid electrolyte compositions described herein have an ionic conductivity of from 0.01 mS/cm to about 2 mS/cm at 25° C. In some embodiments, the non-flammable liquid or solid electrolyte compositions described herein have an ionic conductivity of from 0.1 mS/cm to about 5 mS/cm at 25° C. In some embodiments, the non-flammable liquid or solid electrolyte compositions described herein have an ionic conductivity of from 0.1 mS/cm to about 3 mS/cm at 25° C. In some embodiments, the non-flammable liquid or solid electrolyte compositions described herein have an ionic conductivity of from 0.1 mS/cm to about 2 mS/cm at 25° C.

Electrolyte Compositions Including Carbonate Terminated Fluoropolymer and a Phosphate or Phosphonate Terminated Fluoropolymer In some embodiments, the electrolyte compositions disclosed herein include a 1) carbonate terminated fluoropolymer as given by any of Formulas I-VIII with R' and, optionally, R" including a carbonate group and 2) a phosphate or phosphonate terminated fluoropolymer as given by any of Formulas I-VI with R' and, optionally, R" including a phosphate or phosphonate group.

Examples of carbonate terminated fluoropolymers include PFPE's (referred to as PFPE-carbonates) and other perfluoropolymers having linear carbonate terminated groups as shown in SA1, as well as structures S1-S13, S24-S29, and S38-S41. Further examples of carbonate terminated perfluoropolymers include carbonate terminated perfluoropolymers according to Formulas I-VI having one or few ether units such as shown in structure S11C:

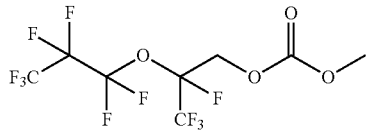

S11C

In some embodiments, the carbonate-terminated fluoropolymer is a perfluoropolyether corresponding to Formula I or Formula II:

(I)

(II)

wherein $R_f$ is a perfluoropolyether backbone;
X is an alkyl, fluoroalkyl, ether, or fluoroether group, wherein 'm' and 'o' are each zero or an integer≥1;
R' is a carbonate containing group; and
R" is an aliphatic, alkyl, aromatic, heterocyclic, or carbonate containing group.

$R_f$, X and R" may be as described above with respect to Formulas I-VI. In some embodiments, the carbonate-terminated fluoropolymer is a perfluoropolyether corresponding to Formula VIII described above.

Examples of phosphate and phosphonate terminated fluoropolymers include PFPE's (referred to as PFPE-phosphates/phosphonates) and other perfluoropolymers having phosphate or phosphonate end groups as shown in S16, S17, S33 and S34. In one example, the phosphate or phosphonate group may be according to P1 or P2:

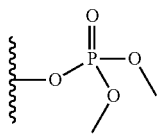

P1

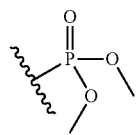

P2

Further examples of functionalized PFPEs comprising a phosphate group are shown below according to structures P3-P10.

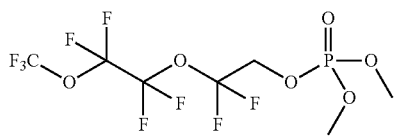

P3

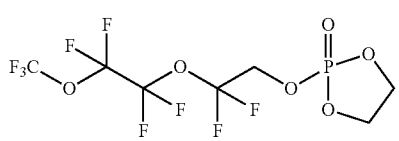

P4

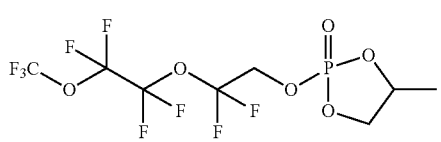

P5

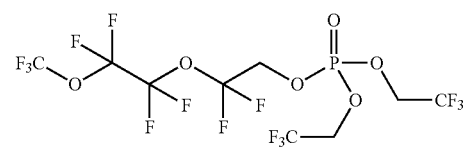

P6

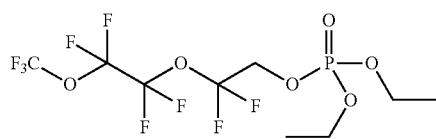

P7

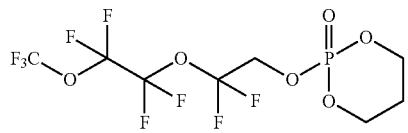

P8

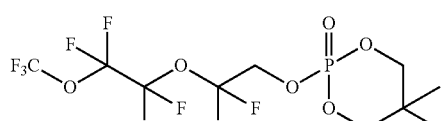

P9

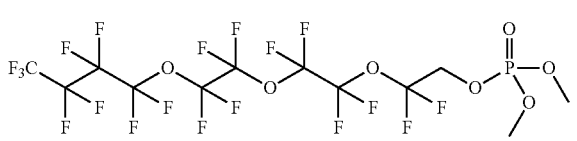

P10

In another example, a functionalized PFPE may comprise one phosphate structure with a branched PFPE backbone as in the example according to structure P11.

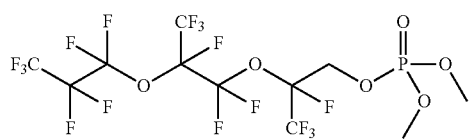

P11

In another embodiment, a functionalized PFPE may comprise two phosphate structures according to structure P12.

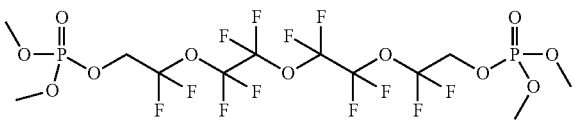

P12

In some embodiments described herein, the phosphate terminated fluoropolymers described herein (e.g., a functionalized perfluoropolyether) may comprise any one or more of the structures selected from the group consisting of structures P13-P14 shown below, wherein X is an alkyl, fluoroalkyl, ether, or fluoroether group as defined in Formulas I-IV and Y' and Y" are any alkyl fluoroalkyl, ether, or fluoroether containing group. In some aspects, Y' and Y" may be part of a ring structure as in structures P8 and P9.

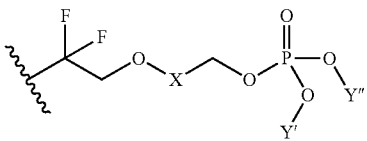

P13

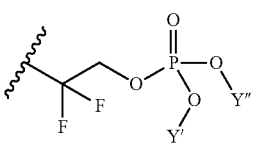

P14

In some embodiments, the phosphate-terminated or phosphonate-terminated perfluoropolyether corresponds to Formula I or Formula II:

$$R_f—X_o—R'  \quad (I)$$

$$R''—X_m—R_f—X_o—R' \quad (II)$$

wherein $R_f$ is a perfluoropolyether backbone;
X is an alkyl, fluoroalkyl, ether, or fluoroether group, wherein 'm' and 'o' are each independently zero or an integer$\geq 1$;
R' is a phosphate or phosphonate containing group; and
R" is an aliphatic, alkyl, aromatic, heterocyclic, phosphate or phosphonate containing group.

$R_f$, X and R" may be as described above with respect to Formulas I-VI.

In some embodiments, the carbonate terminated fluoropolymer and the phosphate or phosphonate terminated fluoropolymer are according to Formula I-VI with $R_f$ being the same for the carbonate terminated fluoropolymer and the phosphate or phosphonate terminated fluoropolymer.

According to various embodiments, an electrolyte composition having a carbonate terminated fluoropolymer and a phosphate or phosphonate terminated fluoropolymer and one or more additional additives, such as conductivity enhancing additives, in Table 4 below, is miscible even in the absence of a salt. While the addition of salt improves miscibility, an electrolyte having miscibility in the absence of a salt is advantageous. Although a PFPE linear carbonate disclosed herein may be able to dissolve lithium salts, conductivities of such electrolytes may be relatively low compared to conventional electrolytes due to the low polarity of the PFPE linear carbonate. As described above, conductivity additives having high flash points such as EC in fairly significant amounts may be added to increase conductivity while maintaining no or low flammability.

Depending on the additive(s) and the carbonate terminated perfluoropolymer, the mixture may not be miscible. The addition of a phosphate terminated or phosphonate perfluoropolymers creates a homogenous mixture, with the phosphate or phosphonate functionality interacting well with polar additives and lithium salts and the perfluoropolymers being fully miscible. Further, the phosphate or phosphonate terminated perfluoropolymer have many or all of the benefits associated with the carbonate terminated perfluoropolymers discussed above, including lack of flammability and relatively high conductivity.

In some aspects, the electrolyte compositions described herein comprise the solvent system shown in Table 4. It should be noted that the solvent systems in Table 5 do not include salts or optional SEI additives, which may be added to the solvent to form an electrolyte.

TABLE 4

Example Fluoropolymer Electrolyte Solvent System

| Component | Example Components | Composition Range (%) |
|---|---|---|
| Carbonate-terminated perfluoropolymer | PFPE carbonate, e.g., PFPE-methyl carbonate | 40-70 |
| Phosphate/phosphonate-terminated perfluoropolymer | PFPE phosphate/phosphonate, e.g., PFPE-methyl phosphate | 5-25 |
| Conductivity enhancing additive(s) | Ethylene carbonate, fluoroethylene carbonate, trispentafluorophenyl borane, lithium bis(oxalato)borate, γ-butyrolactone, etc. | 1-40<br>5-40<br>10-30 |
| Opt. Viscosity reducer(s) | perfluorotetraglyme, γ-butyrolactone, trimethylphosphate, dimethyl methylphosphonate, difluoromethylacetate, fluoroethylene carbonate (FEC), vinylene carbonate (VC), etc. | 0.5-6 |
| Opt. High voltage stabilizer(s) | 3-hexylthiophene, adiponitrile, sulfolane, lithium bis(oxalato)borate, γ-butyrolactone, 1,1,2,2-tetrafluoro-3-(1,1,2,2-tetrafluoroethoxy)-propane, ethyl methyl sulfone, trimethylboroxine, etc. | 0.5-6 |
| Wettability additive | Non-ionic or ionic surfactant, fluorosurfactant, etc. | 0.5-6 |
| Opt. Flame retardant | trimethylphosphate, triethylphosphate, triphenylphosphate, trifluoroethyl dimethylphosphate, tris(trifluoroethyl)phosphate, etc. | 0.5-20 |

In some embodiments, an electrolyte solvent including a PFPE carbonate (or other carbonate terminated perfluoropolymer), a PFPE phosphate/phosphonate (other phosphate/phosphonate terminated perfluoropolymer), and one or more additives has the following characteristics: miscible in the absence of a salt, conductive, no or low flammability, and electrochemically stable. PFPE-carbonates and PFPE-phosphate/phosphonates are conductive and have low or no flammability. PFPE-carbonates are electrochemically stable and have low viscosity, while PFPE-phosphates/phosphonates improve miscibility of PFPE-carbonates in mixtures including one or more conductivity enhancing additives, viscosity reducers, high voltage stabilizers, wettability additives, or flame retardants.

In some embodiments, an electrolyte solvent including a carbonate terminated perfluoropolymer and a phosphate terminated perfluoropolymer include a polar additive such as a C1-C10 or C1-C5 cyclo alkyl carbonate. Although a PFPE linear carbonate disclosed herein may be able to dissolve lithium salts, conductivities of such electrolytes may be relatively low compared to conventional electrolytes due to the low polarity of the PFPE linear carbonate. As described above, conductivity additives having high flash points such as EC in fairly significant amounts may be added to increase conductivity while maintaining no or low flammability. However, depending on the additive(s) and the carbonate terminated perfluoropolymer, the mixture may not be miscible in the absence of a salt. An electrolyte having miscibility in the absence of a salt is advantageous to ensure that during battery operation, if there is a salt concentration gradient or salts come out of solution, that the electrolyte composition remains homogenous.

The addition of a phosphate terminated or phosphonate perfluoropolymers creates a homogenous mixture, with the phosphate or phosphonate functionality interacting well with polar additives and lithium salts and the perfluoropolymers being fully miscible.

In some embodiments, the weight ratio of the carbonate-terminated perfluoropolymer to the phosphate-terminated or phosphonate-terminated perfluoropolymer is at least 1.2:1. In some embodiments, the weight ratio of the carbonate-terminated perfluoropolymer to the phosphate-terminated or phosphonate-terminated perfluoropolymer is at least 1.4:1. In some embodiments, the weight ratio of the carbonate-terminated perfluoropolymer to the phosphate-terminated or phosphonate-terminated perfluoropolymer is at least 1.6:1.

In some embodiments, together the carbonate-terminated perfluoropolymer and phosphate-terminated or phosphonate-terminated perfluoropolymer constitute at least 50% by weight of the electrolyte liquid. In some embodiments, together the carbonate-terminated perfluoropolymer and phosphate-terminated or phosphonate-terminated perfluoropolymer constitute at least 60% by weight of the electrolyte liquid. In some embodiments, together the carbonate-terminated perfluoropolymer and phosphate-terminated or phosphonate-terminated perfluoropolymer constitute at least 60% by weight of the electrolyte liquid.

In some embodiments, the electrolyte liquid is between 40% and 70% carbonate-terminated perfluoropolymer by weight, between 5% and 25% phosphate-terminated fluoropolymer by weight, the balance of the liquid is the one or more additives, and the balance is between 5% and 25% by weight.

In some embodiments, the electrolyte composition is in accordance with the examples shown in Table 5.

TABLE 5

Example Fluoropolymer Electrolyte Solvent System

| Component | Example Components | Composition Range (wt %) |
|---|---|---|
| Lithium salt | LiPF6, LiTSI | 10-35 |
| | | 10-20 |
| SEI additive | Fluoroethylene carbonate, etc. | 0-5 |
| | | 5-30 |
| | | 10-30 |
| Solvent | Mixture of carbonate-terminated perfluoropolymer, phosphate/phosphonate-terminated perfluoropolymer, conductivity enhancer, and other optional additives (see Table 4) | remainder |

Alkali Metal Ion Batteries

An alkali metal ion battery (sometimes also referred to as alkali metal batteries, and including alkali metal-air batteries) of the present invention generally includes (a) an anode; (b) a cathode; (c) a liquid or solid electrolyte composition as described above operatively associated with the anode and cathode, and (d) optionally a separator for physically separating the anode and cathode (See, e.g., M. Armand and J.-M. Tarascon, Building Better Batteries, Nature 451, 652-657 (2008)). In addition, alkali metal batteries may further comprise one or more current collectors at the cathode and anode. Examples of suitable battery components include but are not limited to those described in U.S. Pat. Nos. 5,721,070; 6,413,676; 7,729,949; and 7,732,100, and in U.S. Patent Application Publication Nos. 2009/0023038; 2011/0311881; and 2012/0082930; and S.-W. Kim et al., Adv. Energy Mater. 2, 710-721 (2012), each of which is incorporated by reference herein for their teachings thereof.

Examples of suitable anodes include but are not limited to, anodes formed of lithium metal, lithium alloys, sodium metal, sodium alloys, carbonaceous materials such as graphite, titanium metals, such as, for example lithium titanium oxide (lithium titanate or LTO) and combinations thereof. Examples of suitable cathodes include, but are not limited to cathodes formed of transition metal oxides, doped transition metal oxides, metal phosphates, metal sulfides, lithium iron phosphate, and combinations thereof. See, e.g., U.S. Pat. No. 7,722,994, which is incorporated by reference herein for its teachings thereof. Additional examples include but are not limited to those described in Zhang et al., U.S. Pat. App. Pub No. 2012/0082903, at paragraphs 178 to 179, which is incorporated by reference herein for its teachings thereof. In some embodiments, an electrode such as a cathode can be a liquid electrode, such as described in Y. Lu et al., J Am. Chem. Soc. 133, 5756-5759 (2011), which is incorporated by reference herein for its teachings thereof. Numerous carbon electrode materials, including but not limited to carbon foams, fibers, flakes, nanotubes and other nanomaterials, etc., alone or as composites with each other or other materials, are known and described in, for example, U.S. Pat. Nos. 4,791,037; 5,698,341; 5,723,232; 5,776,610; 5,879,836; 6,066,413; 6,146,791; 6,503,660; 6,605,390; 7,071,406; 7,172,837; 7,465,519; 7,993,780; 8,236,446, and 8,404,384, each of which is incorporated by reference herein for its teachings thereof. In an alkali metal-air battery such as a lithium-air battery, sodium-air battery, or potassium-air battery, the cathode is preferably permeable to oxygen (e.g., where the cathode comprises mesoporous carbon, porous aluminum, etc.), and the cathode may optionally contain a metal catalyst (e.g., manganese, cobalt, ruthenium, platinum, or silver catalysts, or combinations thereof) incorporated therein to enhance the reduction reactions occurring with lithium ion and oxygen at the cathode. See, e.g., U.S. Pat. No. 8,012,633 and U.S. Patent Application Publication Nos. 2013/0029234; 2012/0295169; 2009/0239113; see also P. Hartmann et al., A rechargeable room-temperature sodium superoxide ($NaO_2$) battery, Nature Materials 12, 228-232 (2013), each of which is incorporated by reference herein for its teachings thereof.

Where the electrolyte composition is a liquid composition, a separator formed from any suitable material permeable to ionic flow can also be included to keep the anode and cathode from directly electrically contacting one another. Examples of suitable separators include, but are not limited to, porous membranes or films formed from organic polymers or polyolefin based separators, such as polypropylene, polyethylene, etc., including composites thereof. The useful separators may further have a coating, for example, a ceramic coating (e.g., a polyolefin based separator with a ceramic coating) or a PVDF coating. See generally P. Arora and Z. Zhang, Battery Separators, Chem. Rev. 104, 4419-4462 (2004), which is incorporated by reference herein for its teachings thereof. When the electrolyte composition is a solid composition, particularly in the form of a film, it can serve as its own separator. Such solid film electrolyte compositions of the present invention may be of any suitable thickness depending upon the particular battery design, such as from 0.01, 0.02, 0.1 or 0.2 microns thick, up to 1, 5, 7, 10, 15, 20, 25, 30, 40 or 50 microns thick, or more.

The alkali metal batteries described herein may also include one or more current collectors at the cathode and one or more current collectors at the anode. Suitable current collectors function to transfer a large current output while having low resistance. Current collectors described herein may be, for example, in the form of a foil, mesh, or as an etching. Furthermore, a current collector may be in the form of a microstructured or a nanostructured material generated from one or more suitable polymers. Suitable atomic materials comprise Cu, Fe, Ni, or Ti. In some aspects, the current collectors may be aluminum (Al) at the cathode. Because lithium may react with Al at low potentials, copper (Cu) is typically used at the anode.

Aluminum-based cathodic current collectors are widely used because of their excellent conductivity, high mechanical strength, high ductility, and affordability in commercial settings. Despite these aspects, passivation of the aluminum current collectors is generally necessary to prevent corrosion and diminished cell performance. For example, the lithium salt $LiPF_6$ forms stable interfaces and leads to passivation of the aluminum surface of aluminum-based current collectors (understood to occur by partial decomposition of the lithium salt and oxidation of metallic aluminum at high potentials, forming a dense film of $AlF_3$ on the top of the air-formed surface layer of $Al_2O_3$). While, this protective layer reduces the level of corrosion, aluminum still undergoes a slow corrosion, which in certain cases can be a limiting factor in alkali metal battery performance (e.g., when 5 V class cathode materials are used). Aluminum current collector corrosion may be determined by methods known in the art, see, for example, Kramer et al., Electrochemistry Letters. 1(5) 2012 and Zhang et al., Journal of The Electrochemical Society. 152 (11) 2005, which is incorporated by reference herein for its teachings thereof.

It is well established that sulfonimide-based salts, such as LiTFSI, generally do not properly passivate aluminum-based current collectors with insoluble fluorinated species. Again, although not intending to be limited by theory, it is believed that this is likely due to the stability of the TFSI anion. This lack of passivation eventually leads to severe aluminum current collector corrosion (aluminum dissolution) at potentials higher than 3.5 V leading to decreased contact of the cathode and the aluminum current collector, electrode degradation and rapid cell fading.

Thus, it was surprisingly found that the functionalized PFPE-based solid or liquid electrolyte compositions described herein prevent or reduce the corrosion of aluminum-based current collectors in alkali metal batteries, enabling the use of highly stable lithium salts (e.g., LiTFSI). Similar to how $LiPF_6$ functions to passivate aluminum, and without being bound by any theory, it is believed that the functionalized PFPEs described herein react with aluminum and form a thin passivating film, which protects aluminum from future oxidative corrosion. Although not intended to be limiting, in some aspects, this may occur by formation of an insoluble protective $AlF_3$ layer as a result of PFPE oxidation and aluminum dissolution in the very beginning of the cell charging process. In some other aspects, this may occur by the formation of an $Al(TFSI)_3$ protective layer, which is insoluble in the PFPE based electrolyte compositions described herein.

Therefore, in some embodiments described herein, the PFPE-based solid or liquid electrolyte compositions described herein can prevent or reduce corrosion of aluminum based current collectors. In some aspects, the PFPE-based solid or liquid electrolyte compositions prevent or reduce aluminum current collector corrosion and permit the use of any stable alkali metal salt described herein, including those that do not passivate aluminum. In some aspects, the PFPE-based solid or liquid electrolyte compositions described herein comprising a lithium sulfonimide salt prevent or reduce aluminum current collector corrosion. In one aspect, the PFPE-based solid or liquid electrolyte compositions described herein comprising a LiTFSI prevent or reduce aluminum current collector corrosion.

In some embodiments, the use of a stable lithium salt as described herein (e.g., LiTFSI) in the functionalized PFPE-based solid or liquid electrolyte compositions described herein further decreases the flammability of the electrolyte composition. In some aspects, the combination of a stable lithium salt with PFPE-based electrolyte compositions as described herein further reduces the flammability of the electrolyte composition as compared to a PFPE-based electrolyte composition alone. In some aspects, the use of a stable lithium salt (e.g., LiTFSI) with a PFPE-based electrolyte composition as described herein reduces gas build up and eventual rupture or gaseous explosion risk of a susceptible alkali metal battery.

In some embodiments, the use of a stable lithium salt as described herein (e.g., LiTFSI) in the functionalized PFPE-based solid or liquid electrolyte compositions described herein in an alkali metal battery increases the potential operating temperature of the battery without incurring battery failure. In one aspect, the operating temperature may be from about −30° C. to about 150° C., including each integer within the specified range. In another aspect, the operating temperature may be from about −30° C. to about 50° C., including each integer within the specified range. In another aspect, the operating temperature may be from about −30° C. to about 100° C., including each integer within the specified range. In another aspect, the operating temperature may be from about −30° C. to about 150° C., including each integer within the specified range. In another aspect, the operating temperature may be from about −10° C. to about 150° C., including each integer within the specified range. In another aspect, the operating temperature may be from about 0.0° C. to about 150° C., including each integer within the specified range. In another aspect, the operating temperature may be from about 70° C. to about 200° C., including each integer within the specified range. In another aspect, the operating temperature may be from about 90° C. to about 200° C., including each integer within the specified range. In another aspect, the operating temperature may be from about 110° C. to about 200° C., including each integer within the specified range. In another aspect, the operating temperature may be from about 140° C. to about 200° C., including each integer within the specified range. In another aspect, the operating temperature may be from about 180° C. to about 200° C., including each integer within the specified range. In another aspect, the operating temperature may be from about 180° C. to about 200° C., including each integer within the specified range. In another aspect, the upper limit of the battery operating temperature may be at least about 50° C., at least about 60° C., at least about 70° C., at least about 80° C., at least about 90° C., at least about 100° C., at least about 110° C., at least about 120° C., at least about 130° C., at least about 140° C., or at least about 150° C. In another aspect, the lower limit of the battery operating temperature may be at least about −30° C., at least about −20° C., at least about −10° C., at least about 0° C., at least about 10° C., or at least about 20° C.

All components of the battery can be included in or packaged in a suitable rigid or flexible container with external leads or contacts for establishing an electrical connection to the anode and cathode, in accordance with known techniques.

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of the specified embodiments. All of the various embodiments, aspects, and options disclosed herein can be combined in all variations. The scope of the compositions, formulations, methods, and processes described herein include all actual or potential combinations of embodiments, aspects, options, examples, and preferences herein described. All patents and publications cited herein are incorporated by reference herein for the specific teachings thereof.

EXAMPLES

Example 1

Synthesis of a Cyclic PFPE Carbonate

A 250 mL round bottom flask equipped with a stir bar was charged with 50.0 g (0.091 mole) of 1H,1H-perfluoro-3,6,9-trioxatridecan-1-ol, 4.01 g (0.100 mole) of sodium hydroxide and 84 g (71 mL, 0.91 mole) of epichlorohydrine, sealed and placed in an oil bath thermostated at 60° C. The reaction was stopped after 18 hrs, the unreacted epichlorohydrin was removed using rotary evaporator and the residue was diluted with 300 mL of ethyl acetate. The solution was washed with water (2×150 mL) and brine (150 mL), the aqueous layer was extracted with ethyl acetate (100 mL) and combined organic fractions were dried over magnesium sulfate. The filtrate was concentrated and distilled under reduced pressure obtaining 36.5 g (0.059 mole) of the product with 64.6% yield.

A 250 mL Schenk flask equipped with a stir bar was charged with 35.0 g (0.058 mole) of 2-(1H,1H,3H,3H-perfluoro-2,5,8,11-tetraoxapentadecyl)oxirane, 0.98 g (2.4 mmole) of methyltriphenylphosphonium iodide and 40 mL of 1-methoxy-2-propanol. Next, a balloon was attached to the flask, filled with carbon dioxide and the reaction was run at room temperature for four days. During that time the balloon was refilled several times to maintain the positive pressure of carbon dioxide in the vessel. The solvent was removed using rotary evaporator, the residue was dissolved in ethyl acetate (200 mL), washed with water (2×100 mL) and brine (100 mL), dried over magnesium sulfate and concentrated in vacuo. The residue was vacuum distilled to remove unreacted starting materials. The crude product was recrystallized from ethanol giving 15.65 g (0.024 mole) of 4-(1H,1H,3H,3H-perfluoro-2,5,8,11-tetraoxapentadecyl)-1,3-dioxolan-2-one (S8) as white crystals. Yield of the reaction was 41.7%.

Example 2

Synthesis of a Linear PFPE Carbonate According to Structure S2

100 g 1H, 1H, 11H,11H-Perfluoro-3,6,9-trioxaundecan-1,11-diol, 75 mL Et3N and 500 mL 1,1,1,3,3-pentafluorobutane are mixed in a 1 L round bottom flask containing 20 g activated 3 Å sieves. This solution is allowed to sit for 24 hours over the sieves. The solution is transferred under nitrogen, via cannula, into a 1 L 3-neck round bottom flask. One neck has a gas adaptor connected to a nitrogen source, one neck has a 100 mL pressure-equalized addition funnel and the remaining neck has a septum which is used for the cannula transfer. The reaction vessel is immersed in an ice-bath and the addition funnel is charged with 38 mL methyl chloroformate and 50 mL 1,1,1,3,3-pentafluorobutane. The chloroformate solution is added dropwise over the course of an hour to the reaction vessel. Once addition is complete the ice-bath is removed and the reaction stirred at room temperature for four hours. The solution is filtered, and then washed with 500 mL 5% HCl and 2×500 mL DI water. The solution is then dried with MgSO4, filtered, and the 1,1,1,3,3-pentafluorobutane and any other volatiles removed by rotary evaporation. The resulting colorless oil distilled under vacuum at 200 millitorr. The slightly yellow oil which is left behind is saved to be combined with future batches and re-distilled as it is found to contain mostly desired product. The material is dried for 2 days over 20 g 3 Å activated molecular sieves before use.

Example 2A

Synthesis of a Linear PFPE Carbonate According to Structure S7

A 2 L round bottom flask was charged with 192 mL (1.376 mole) of triethylamine, 350.2 g (1.241 mole) of 1H,1H-nonafluoro-3,6-dioxaheptan-1-ol, 1.25 L of 1,1,1,3,3-pentafluorobutane and 3 Å molecular sieves, then sealed and dried overnight. A 3 L, three-neck, jacketed round bottom flask was equipped with a gas adapter, addition funnel and an overhead mechanical stirrer. The flask was purged with nitrogen and cooled with and ice water. Next, the dried solution was transferred to the reaction flask via cannula needle, and allowed to cool down before proceeding to the next step. 105 mL (1.366 mole) of methyl chloroformate in 100 mL of dry 1,1,1,3,3-pentafluorobutane was transferred to the addition funnel, followed by a dropwise addition to the vigorously stirred reaction mixture over 2 hours. Upon the addition, the reaction mixture was allowed to warm up to room temperature and stirred for additional 2 hours. Afterwards, the precipitate was filtered off, washed with 1,1,1,3,3-pentafluorobutane, and the filtrate was concentrated in vacuo. The residual organic layer was washed with water (2×200 mL) and brine (1×200 mL), dried with anhydrous magnesium sulfate and the solvent was removed. The crude product was vacuum distilled, obtaining 375.0 g (1.103 mole) of 1H,1H-nonafluoro-3,6-dioxaheptanyl methyl carbonate as a clear, colorless liquid with 89.0% yield (25° C./0.1-0.2 Torr).

Example 2B

Synthesis of a Linear PFPE Carbonate According to Structure S8

A 2 L round bottom flask was charged with 192 mL (1.376 mole) of triethylamine, 350.2 g (1.241 mole) of 1H,1H-nonafluoro-3,6-dioxaheptan-1-ol, 1.25 L of 1,1,1,3,3-pentafluorobutane and 3 Å molecular sieves, then sealed and dried overnight. A 3 L, three-neck, jacketed round bottom flask was equipped with a gas adapter, addition funnel and an overhead mechanical stirrer. The flask was purged with nitrogen and cooled with and ice water. Next, the dried solution was transferred to the reaction flask via cannula needle, and allowed to cool down before proceeding to the next step. 105 mL (1.366 mole) of methyl chloroformate in 100 mL of dry 1,1,1,3,3-pentafluorobutane was transferred to the addition funnel, followed by a dropwise addition to the vigorously stirred reaction mixture over 2 hours. Upon the addition, the reaction mixture was allowed to warm up to room temperature and stirred for additional 2 hours. Afterwards, the precipitate was filtered off, washed with 1,1,1,3,3-pentafluorobutane, and the filtrate was concentrated in vacuo. The residual organic layer was washed with water (2×200 mL) and brine (1×200 mL), dried with anhydrous magnesium sulfate and the solvent was removed. The crude product was vacuum distilled, obtaining 375.0 g (1.103 mole) of 1H,1H-nonafluoro-3,6-dioxaheptanyl methyl carbonate as a clear, colorless liquid with 89.0% yield (25° C./0.1-0.2 Torr).

Example 3

Dissolution of Ethylene Carbonate in a Carbonate Terminated PFPE

Carbonate-terminated PFPE materials and ethylene carbonate are immiscible but experience salt-induced miscibility upon introduction of certain lithium salts. It was found that 1.0M $LiPF_6$ dissolved in a linear PFPE carbonate according to structure S2 (also referred to as tetra-dMe) is immiscible with EC at any concentration; however 1.0M LiTFSI is miscible up to at least 30 wt % EC. Without being bound by any theory, this is likely due to the more complete dissociation of LiTFSI versus $LiPF_6$ in the PFPE. The enhanced dissociation increases the ionic strength of the solution, which made it more favorable for the highly polar ethylene carbonate to dissolve.

Example 4

Electrochemical Measurements

The conductivity of electrolyte compositions and cyclic voltammetry measurements of perfluoropolyether based electrolyte compositions were determined experimentally using similar methods as described by Teran et al., Solid State Ionics (2011) 203, p. 18-21; Lascaud et al., Maromolecules (1994) 27 (25); and International Patent Application Publication Nos. WO2014/204547 and WO2014/062898, each of which are incorporated by reference herein for their teachings thereof.

Example 5

Temperature-Dependent Ionic Conductivity of Perfluoropolyether Based Electrolyte Compositions As shown in FIG. 1, the conductivity of electrolyte compositions comprising a linear carbonate terminated perfluoropolyether according to structures S2, S3, S7 and a perfluoropolyether with a structure according to Formula VII having a number average molecular weight of about 2,000 g/mol (also referred to as D10H-dMe) and 1.0M LiTFSI decreases across a range of temperatures.

Example 6

Conductivity of PFPE's

Figure 2:
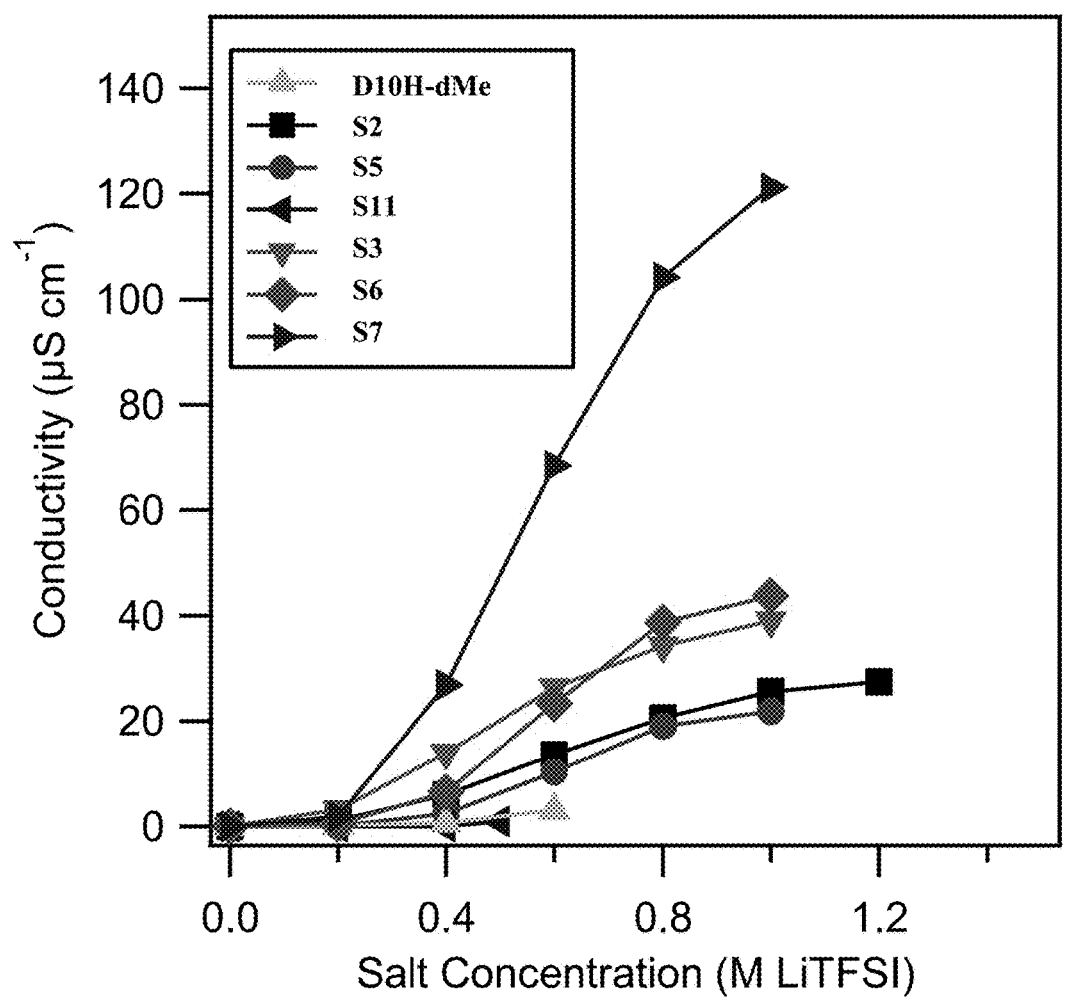
FIG. 2 shows ionic conductivity of PFPE-based electrolyte compositions at different concentrations of LiTFSI.

The conductivity of several perfluoropolyethers according to structures S2, S3, S5, S6, S7, S11 and a perfluoropolyether with a structure according to Formula VII having a number average molecular weight of about 2,000 g/mol (also referred to as D10H-dMe) as a function of LiTFSI salt concentration was measured. As shown in FIG. 2, the conductivity increases with increasing LiTFSI content.

Example 7

Coin Cell Battery Testing of Electrolyte Compositions

Figure 3:
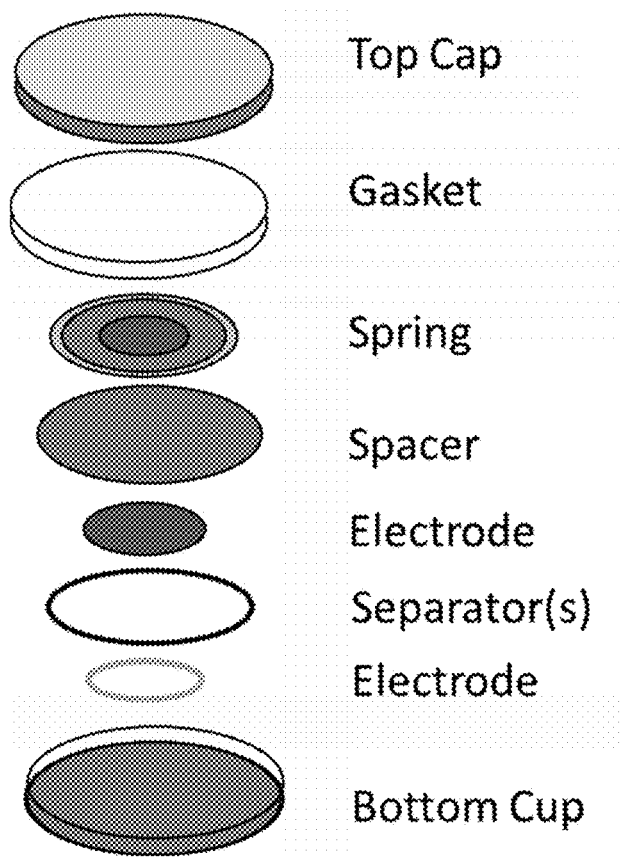
FIG. 3 shows a schematic of an example of a coin cell battery.

Coin cell batteries as depicted by the schematic in FIG. 3 were fabricated for testing of electrolyte compositions.

Example 8

Figure 4:
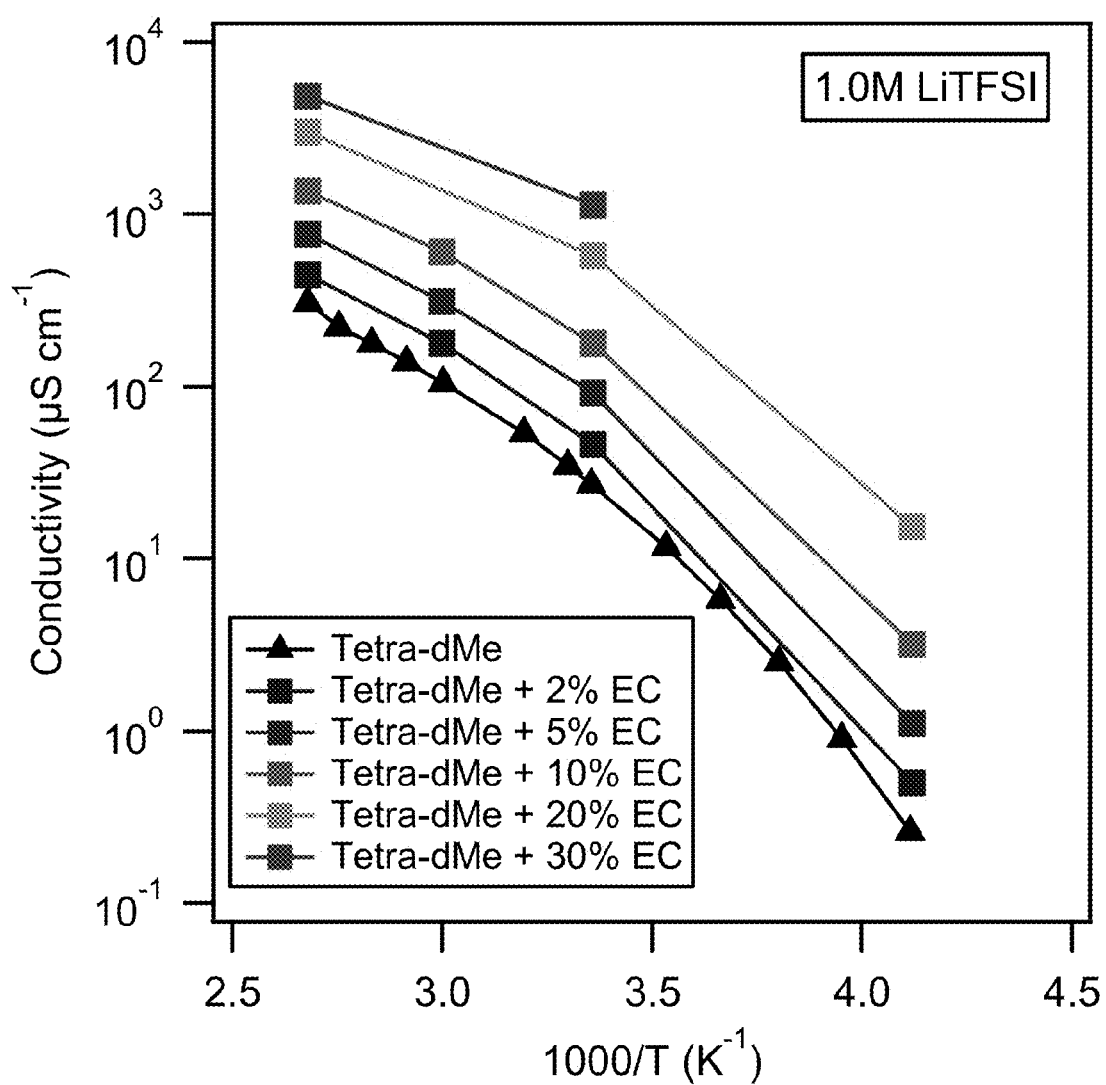
FIG. 4 shows ionic conductivity of electrolyte solutions across a range of temperatures.
Figure 5:
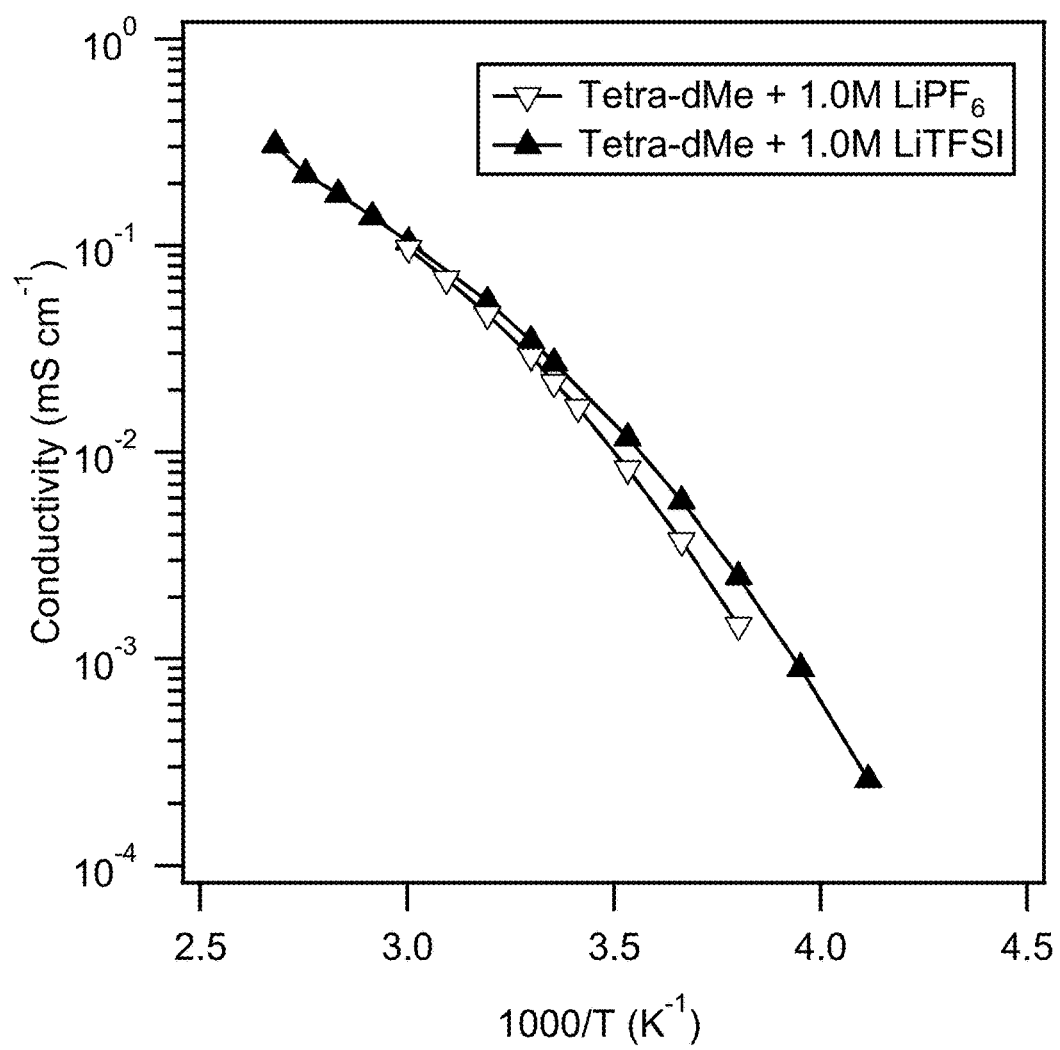
FIG. 5 shows ionic conductivity of electrolyte solutions across a range of temperatures with either $LiPF_6$ or LiTFSI salts.

Temperature-Dependent Ionic Conductivity of a Linear PFPE Carbonate and Ethylene Carbonate Containing Electrolyte Solution As shown in FIG. 4, the conductivity of electrolyte solutions containing a linear carbonate terminated PFPE according to structure S2 (also referred to as tetra-dMe) decreases with across a range of temperatures. It was found that increasing concentration of ethylene carbonate increases the conductivity across a range of temperatures. Similar results were observed with either $LiPF_6$ or LiTFSI salts at a 1.0 M concentration (FIG. 5).

Example 9

Cyclic Voltammetry of a Linear PFPE Carbonate Containing Electrolyte Solution

Figure 6:
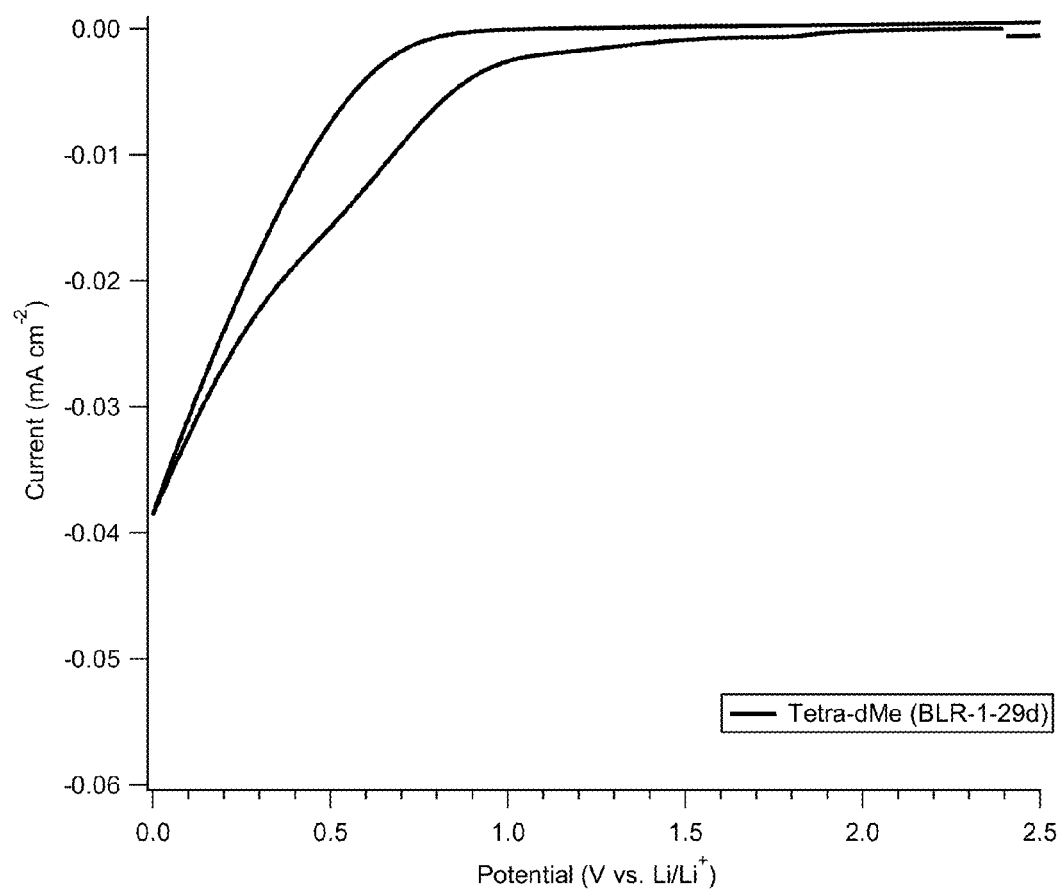
FIG. 6 shows cathodic scan cyclic voltammetry data of a PFPE-based electrolyte solution.
Figure 7:
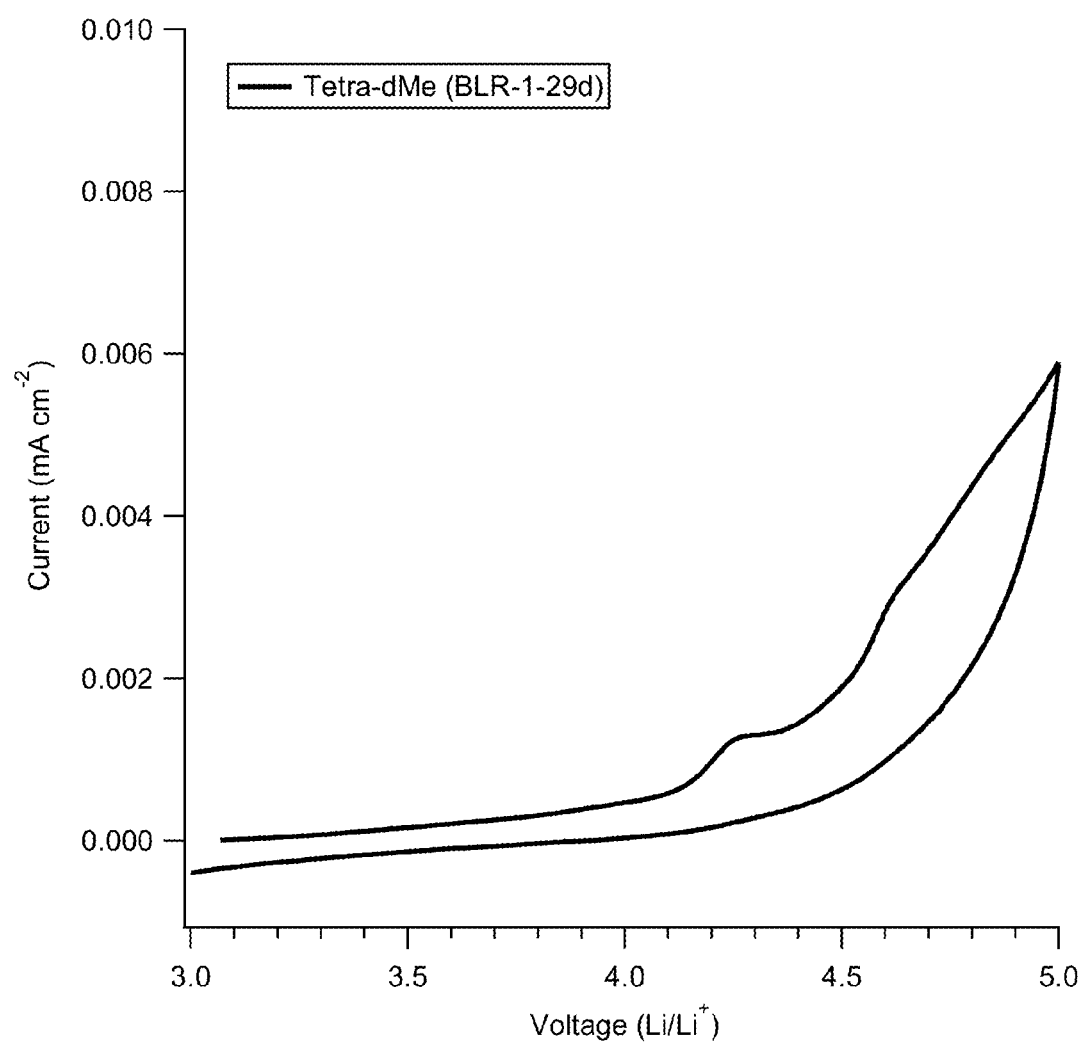
FIG. 7 shows anodic scan cyclic voltammetry data of a PFPE-based electrolyte solution.

The electrochemical stability of a linear carbonate terminated PFPE according to structure S2 (also referred to as tetra-dMe) with 1.0 M LiTFSI was tested and demonstrated electrochemical stability. FIG. 6 shows the cathodic scan on a glassy carbon working electrode at 25° C. and FIG. 7 shows the anodic scan on a Pt working electrode at 25° C.

Example 10

High Voltage Scan of Electrolyte Solutions

Figure 8:
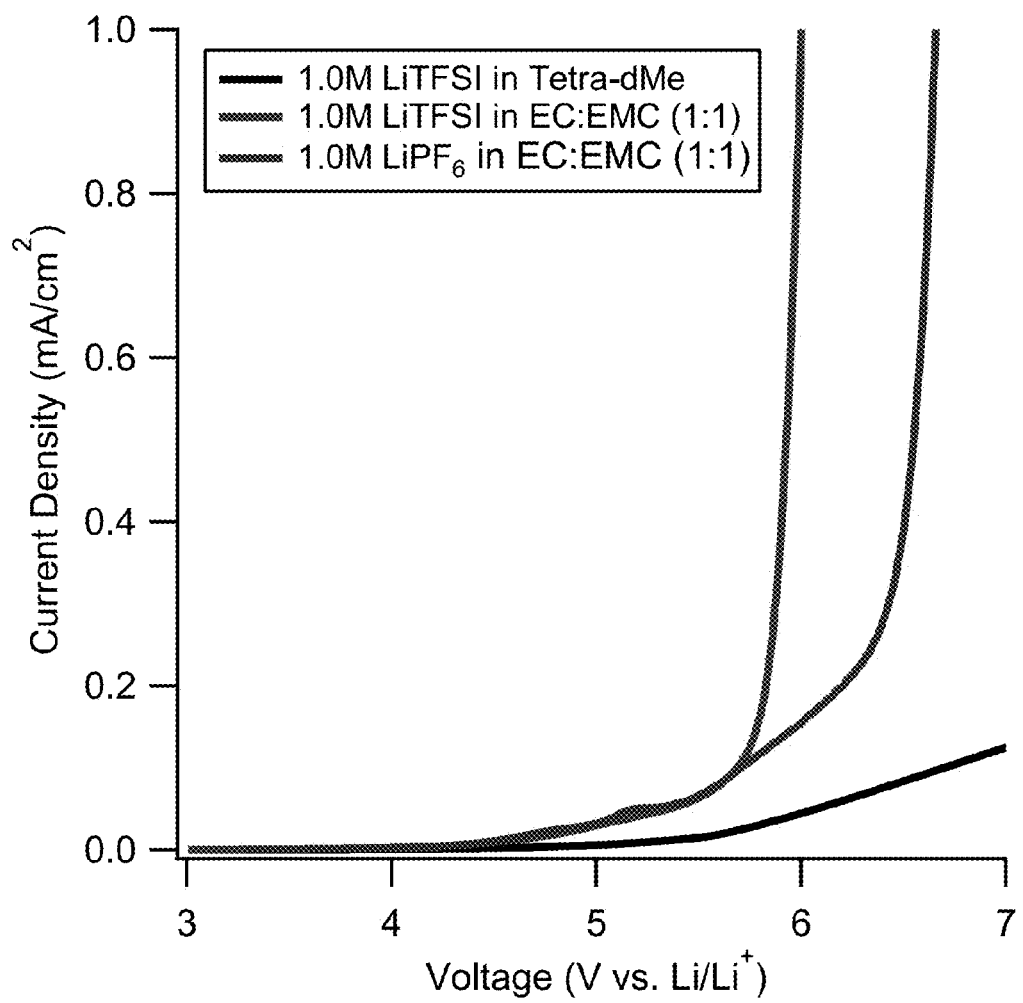
FIG. 8 shows data from high voltage scans of various electrolyte solutions.

A voltage sweep to 7V on a Pt working electrode (a lithium reference electrode and a Pt counter electrode) with a linear carbonate terminated PFPE according to structure S2 (also referred to as tetra-dMe) in 1.0 M LiTFSI compared to other conventional electrolyte systems is shown in FIG. 8. Accordingly, the highly fluorinated backbone of the PFPE imparts oxidative stability for PFPE based electrolytes.

Example 11

Cycling Performance and Stability of Active Materials in Coin Cell Batteries

The performance of a linear carbonate terminated PFPE according to structure S2 (also referred to as tetra-dMe) supplemented with 10% ethylene carbonate with different half-cell materials was tested. The cycling experiments were carried out at room temperature with 1.0M LiTFSI. PFPE neat compositions without ethylene carbonate were cycled at a C/10 discharge rate, whereas compositions containing ethylene carbonate were cycled at a C/5 discharge rate.

Figure 9:
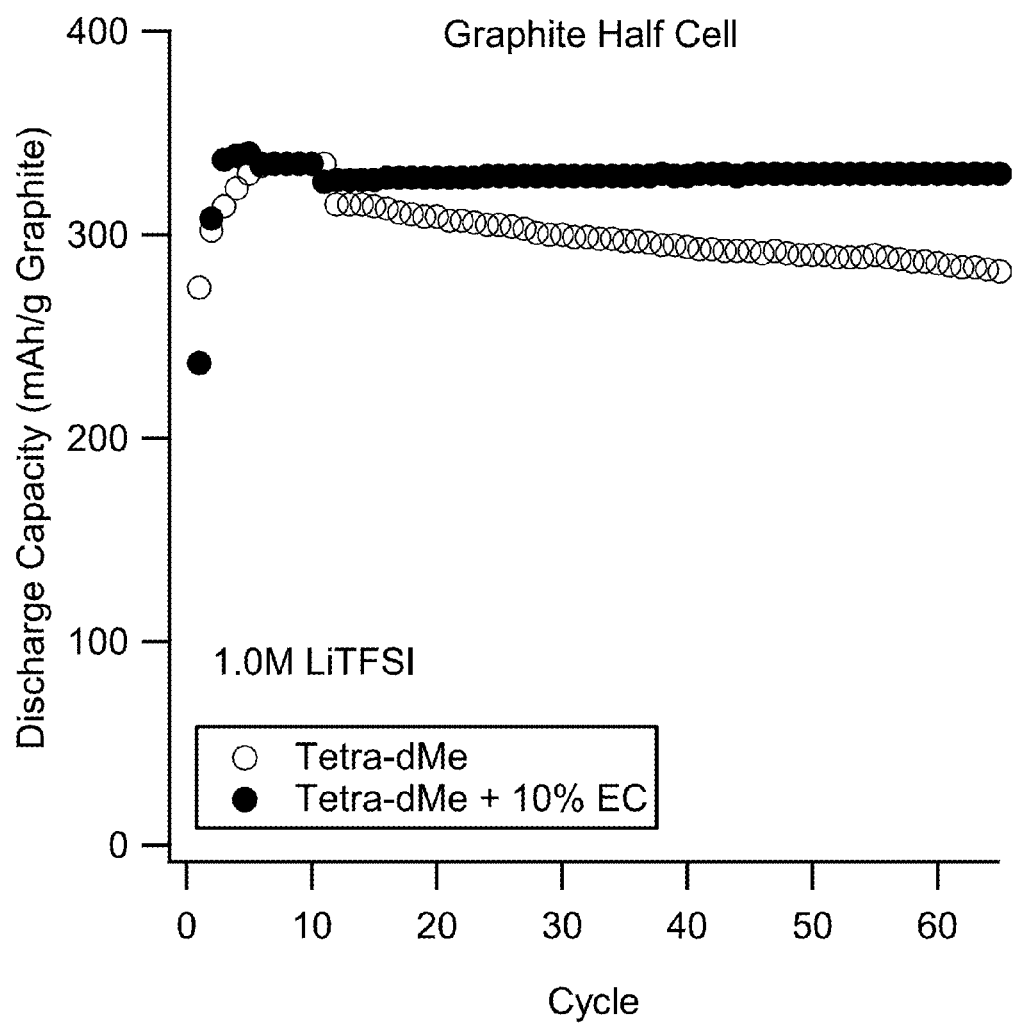
FIG. 9 shows cycling performance and stability of PFPE and ethylene carbonate electrolyte solutions with a graphite-based half-cell in a coin cell battery.
Figure 10:
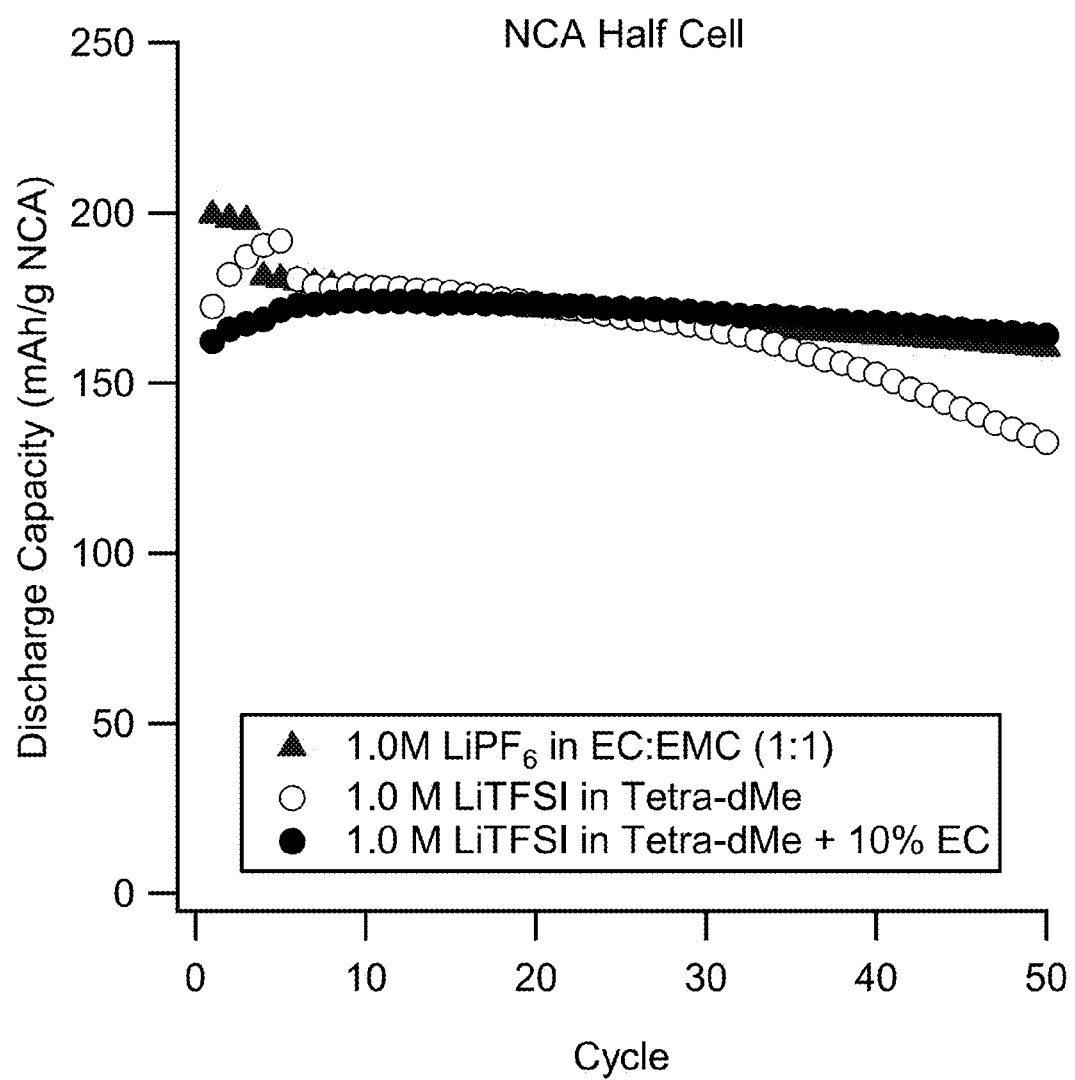
FIG. 10 shows cycling performance and stability of PFPE and ethylene carbonate electrolyte solutions with a lithium nickel cobalt aluminum oxide (NCA)-based half-cell in a coin cell battery.
Figure 11:
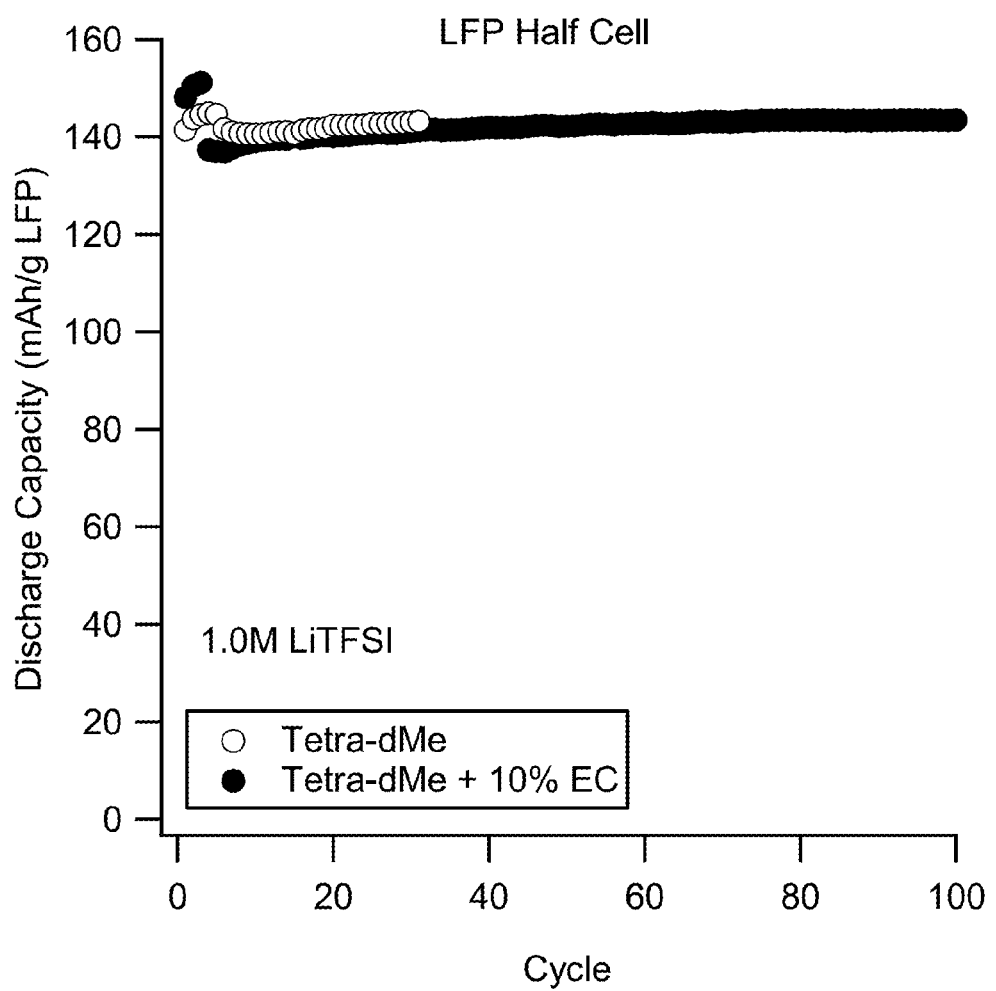
FIG. 11 shows cycling performance and stability of PFPE and ethylene carbonate electrolyte solutions with a lithium iron phosphate (LFP)-based half-cell in a coin cell battery.

As shown in FIG. 9, the presence of 10% ethylene carbonate improved the cycling performance of graphite based coin cells even at the C/5 discharge rate. The cycling performance of lithium nickel cobalt aluminum oxide (NCA) based half cells with a PFPE and 10% ethylene carbonate electrolyte solution with LiTFSI was similar to a commercial electrolyte solution with $LiPF_6$, whereas the PFPE neat composition demonstrated a decrease in discharge capacity after about 30 cycles FIG. 10. As shown in FIG. 11, the discharge capacity of a LFP half-cell is constant for 40 cycles for the PFPE neat composition with 1.0 M LiTFSI; these data represents a still cycling coin cell at 40 cycles. The PFPE composition supplemented with 10% ethylene carbonate maintained a constant discharge capacity for about 100 cycles.

Example 12

Conductivity of Conductivity Enhancing Additives

Figure 12:
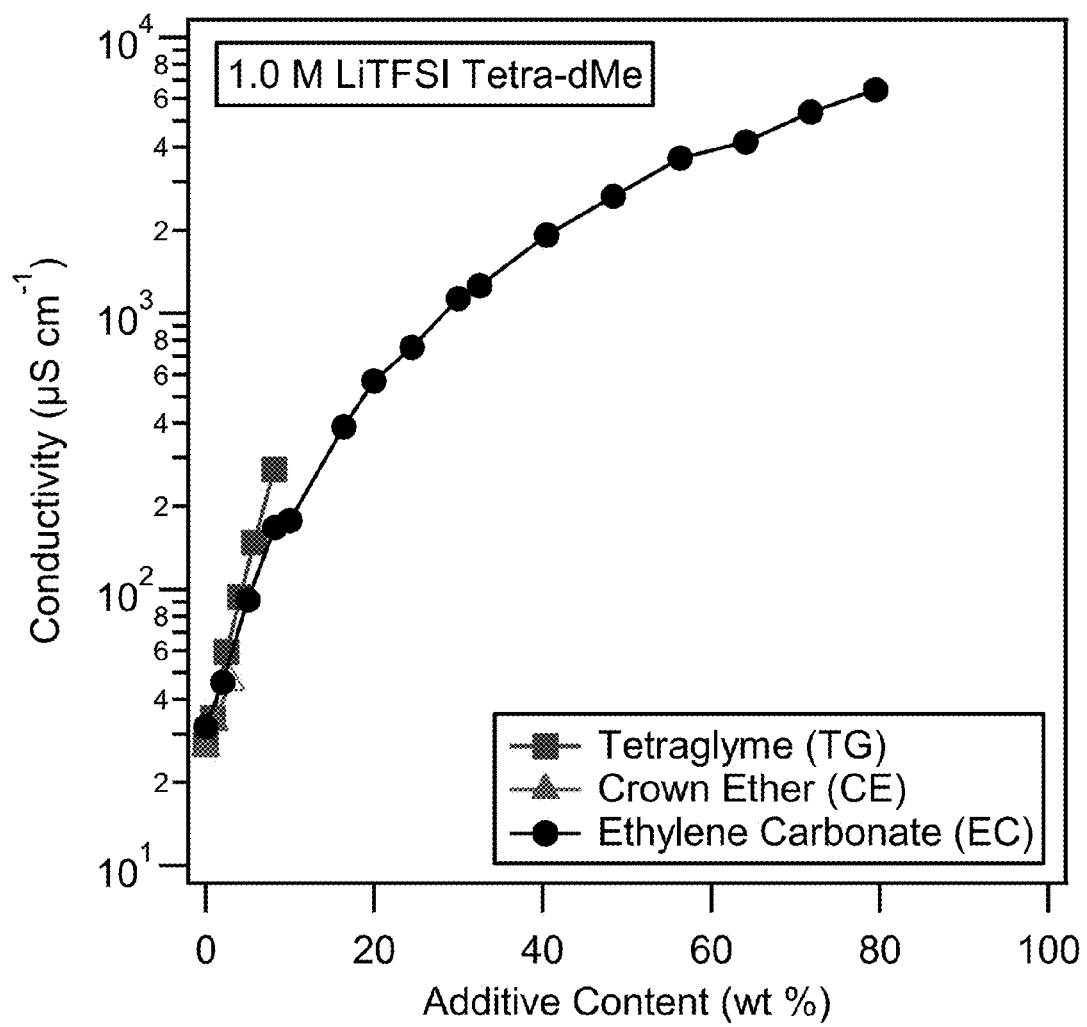
FIG. 12 shows conductivity of increasing concentrations of conductivity enhancing additives in various electrolyte solutions.

The conductivity of a linear carbonate terminated PFPE according to structure S2 (also referred to as tetra-dMe) supplemented with increasing concentrations of tetraglyme, crown ether, or ethylene carbonate with 1.0 M LiTFSI was tested. As shown in FIG. 12, the relative conductance of the electrolyte solutions increased with addition of each additive.

Example 13

Perfluoropolyether Mediated Suppression of Aluminum Corrosion

Figure 13:
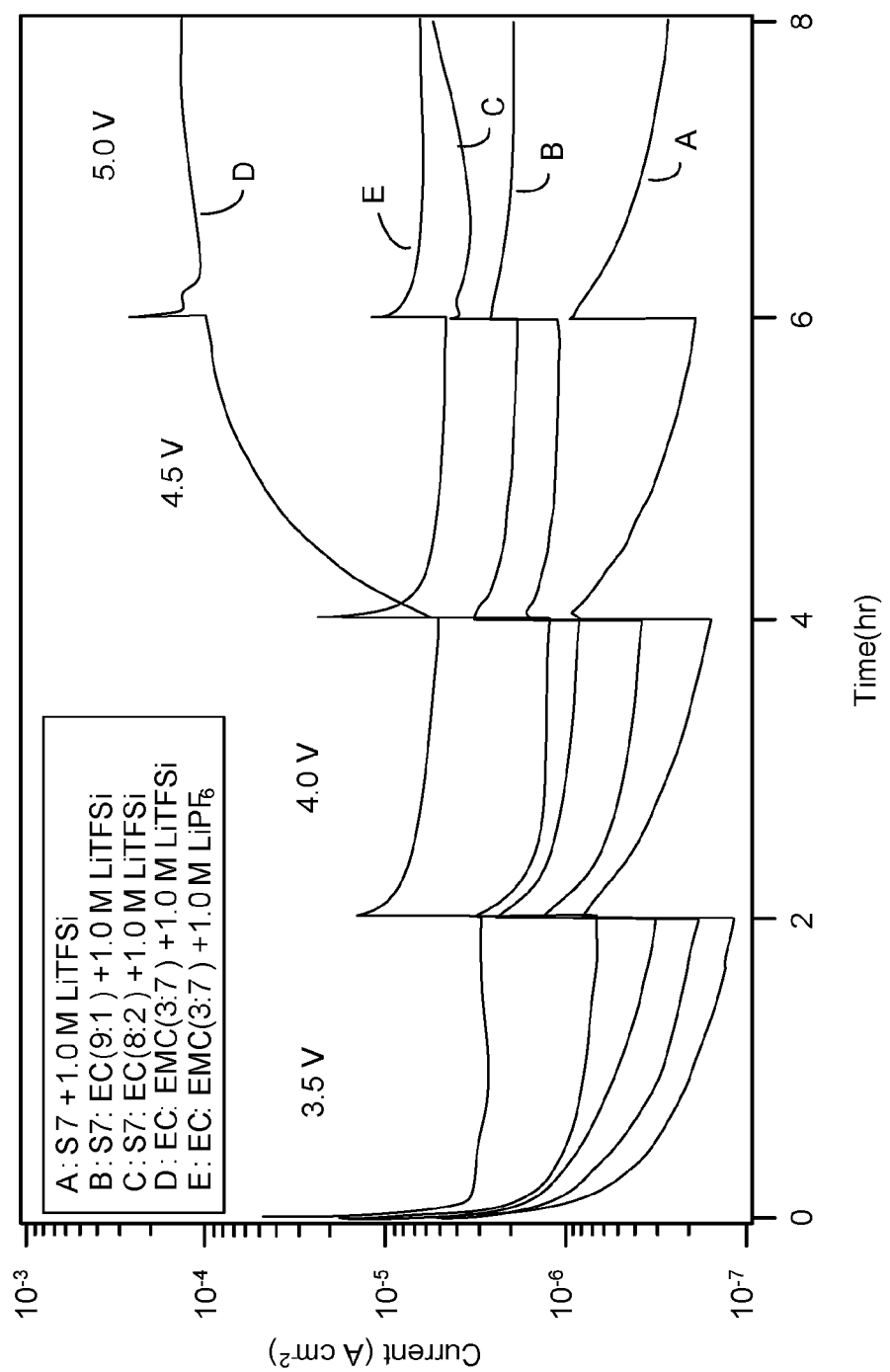
FIG. 13 shows a comparison of aluminum current collector corrosion in a reference electrolyte composition including $LiPF_6$ and PFPE-based electrolyte compositions including LiTFSI.

The suppression of aluminum corrosion in an electrolyte composition having LiTFSI and a linear perfluoropolyether according to structure S7 was tested. These experiments were performed by holding a constant voltage in a coin cell with an aluminum working electrode and a lithium metal counter/reference electrode. Any current observe is assumed to be the corrosion of the aluminum. The lower the current, the less corrosion is occurring. The extent of aluminum corrosion in electrolyte compositions with PFPEs and LiTFSI (curves A-C) was compared to a reference standard electrolyte standard composition of $LiPF_6$ in a mixture of ethylene carbonate/ethyl methyl carbonate (EC/EMC) (E) as shown in FIG. 13. The corrosion current values observed in the PFPE-based electrolyte compositions are lower than those observed in the reference electrolyte composition (E), which is widely used in commercial cells and known to suppress aluminum corrosion. Aluminum undergoes severe corrosion in the reference organic carbonate-based electrolyte composition (D).

Example 14

Conductivities and Flash Points of Linear PFPE-Carbonates

Flash points and conductivities of unbranched, linear PFPE-carbonates of various sizes were measured.

| Molecule | Mono- or di- functional | MW of $R_f$ | Number of carbons in $R_f$ | Flash Point (° C.) | Conductivity 1.0M LiTFSI @ 25° C. (mS/cm) |
|---|---|---|---|---|---|
| D10H-dME | di | about 1800 | >20 | None | did not solvate 1.0M LiTFSI |
| S2 | di | 348 | 6 | 180 | 0.03 |
| S3 | di | 232 | 4 | 154 | 0.04 |
| S5 | mono | 517 | 9 | None | 0.02 |
| S6 | mono | 401 | 7 | None* | 0.04 |
| S7 | mono | 251 | 4 | None* | 0.12 |

S2 and S3 differ only by the presence of a $-(CF_2CF_2O)-$ subunit, as do S5 and S6. Comparing S2 and S3, the conductivity of S3 is 50% greater than that of S2. Comparing S5 and S6, the conductivity of S6 is twice that of S5. Based on these results, it is expected that increasing the size of S2 or S5 would show lower or no conductivity. S6 differs from S7 by the presence of a terminal butyl rather than a terminal methyl chain, with conductivity of S7 three times that of S6. These results indicate that the size of $R_f$, which may be characterized by molar mass (or molecular weight) or number of carbons, is critical for conductivity.

In this and other examples, the presence of an asterisk (*) on flash point measurements indicates that while the sample did not exhibit a traditional 'flash' and failed to trigger the detector, at temperatures above 100° C. a small green flame was sometimes visible directly on the electric heating coil of the flash-point tester as it glowed red hot and dipped into the vapor space. It is believed that this is due to decomposition of the material directly on the coil, which achieves temperatures in excess of 1000° C., rather than ignition of the vapors.

Example 15

Conductivities and Flash Points of Branched PFPE Carbonates

Flash points and conductivities of branched linear PFPE-carbonates of various sizes were measured.

| Molecule | Mono- or di- functional | MW of $R_f$ | Number of carbons in $R_f$ | Flash Point (° C.) | Conductivity 1.0M LiTFSI @ 25° C. (mS/cm) |
|---|---|---|---|---|---|
| S11A | mono | 617 | 11 (8 along main chain) | None | None |
| S11B | mono | 451 | 8 (6 along main chain) | None | None |
| S11C | mono | 285 | 5 (4 along main chain) | None | 0.05 |

These results indicate that the size of $R_f$, which may be characterized by molar mass (or molecular weight) or number of carbons, is critical for conductivity. In addition, unbranched PFPE-carbonates are more conductive than similarly sized branched PFPE-carbonates. This is unexpected, as the unbranched PFPE-carbonates would be expected to be more viscous, and less conductive than branched PFPE-carbonates. Without being bound by a particular theory, it is believed that branched chains that are too close to the carbonate or other functional group sterically hinder Li ion coordination with the functional group.

Example 16

Conductivities and Flash Points of Linear PFPE-Carbonates Having Different R' Groups Flash points and conductivities of branched linear PFPE-carbonates of various sizes were measured.

| Molecule | Flash Point (° C.) | Conductivity 1.0 M LiTFSI @ 25° C. (mS/cm) |
|---|---|---|
| S7 | 120 | 0.12 |
| S7A (S7 with ethyl carbonate end group) | 88 | 0.09 |

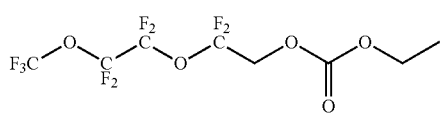

| Molecule | Flash Point (° C.) | Conductivity 1.0 M LiTFSI @ 25° C. (mS/cm) |
|---|---|---|
| S7 with trifluoroethyl carbonate end group | None | None (does not dissolve 0.1 M salt) |

$F_3C\diagup O\diagup CF_2\diagup CF_2\diagup O\diagup CH_2\diagup O\diagup C(=O)\diagup O\diagup CH_2\diagup CF_3$ Notably, the PFPE with a methyl carbonate end group has higher conductivity and is less flammable than the PFPE with an ethyl carbonate end group, though the conductivity of the ethyl carbonate is still high. Adding fluorine to the carbonate end group results in a less flammable compound that does not dissolve 1.0 M LiTFSI.

Example 17

Figure 14:
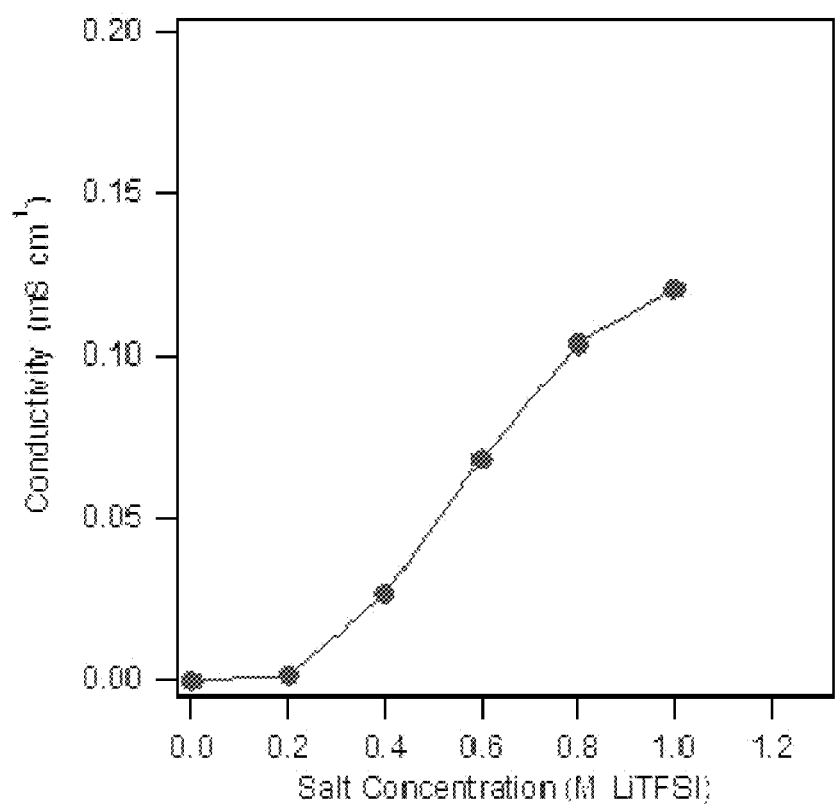
FIG. 14 shows ionic conductivity of a linear carbonate terminated PFPE-based electrolyte composition at different concentrations of LiTFSI.
Figure 15:
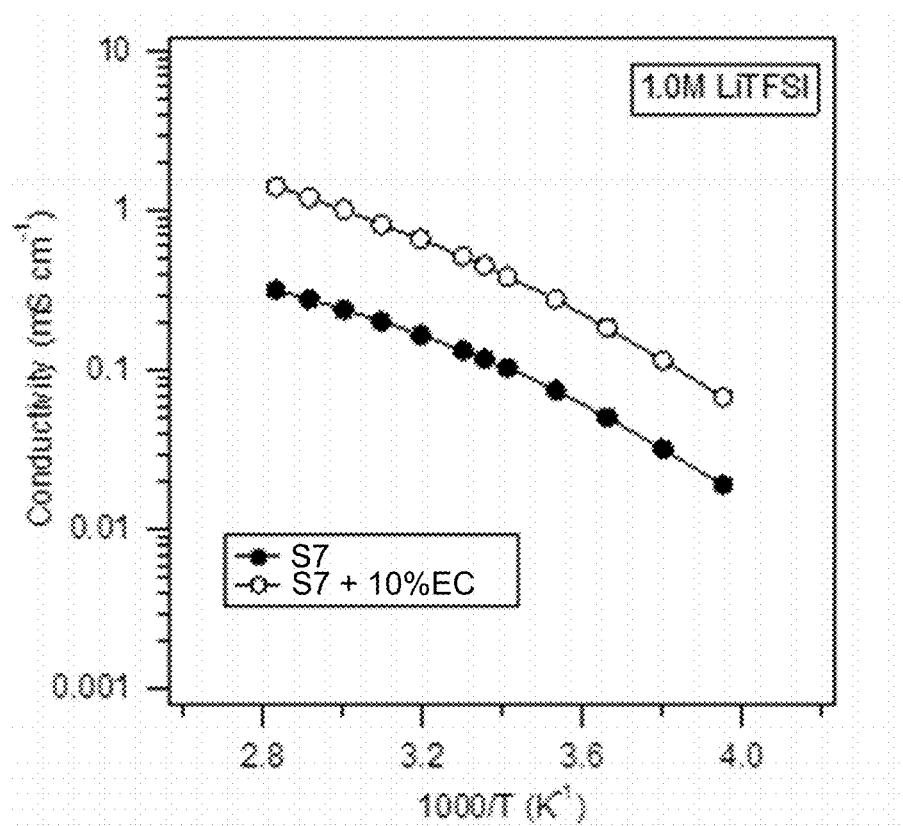
FIG. 15 shows ionic conductivity of electrolyte solutions across a range of temperatures.

Conductivity of a Linear Carbonate PFPE as a Function of Salt Concentration and Temperature Conductivity of solution of S7 with LiTFSI salt was measured as a function of salt concentration and temperature. Results are in FIGS. 14 and 15. FIG. 15 shows that the conductivity is increased with the addition of 10% EC.

Example 18

Figure 16:
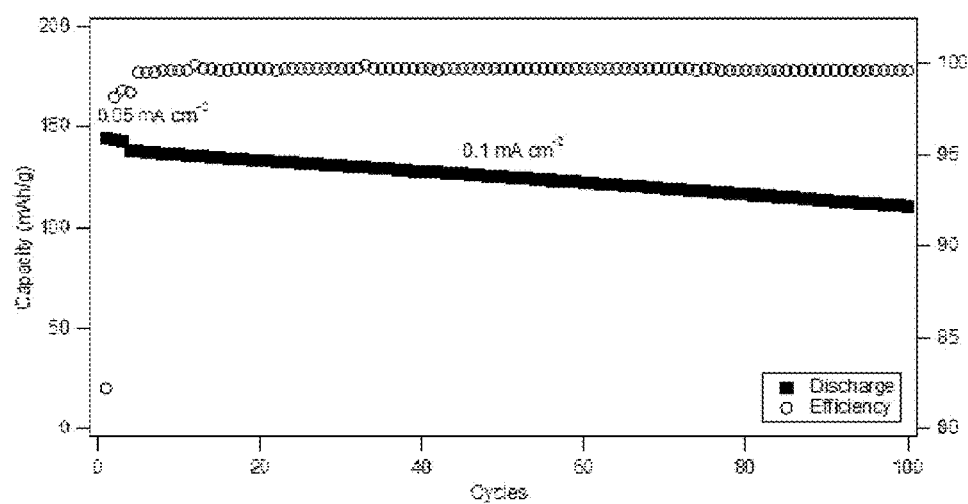
FIG. 16 shows cycling performance and stability of a neat linear carbonate terminated PFPE electrolyte in a graphite/nickel-manganese-cobalt (NMC) cell.

Cycling Performance and Stability of Linear Carbonate PFPE in Coin Cell Batteries The performance of a linear carbonate terminated PFPE according to structure S7 was tested on a graphite/nickel-manganese-cobalt (NMC) cell. The S7 solution was neat (with the addition of 2% FEC as an SEI additive for the graphite cathode). The cycling experiment was carried out at room temperature with 1.0M LiTFSI. Formation rate was C/20 and cycling rate was C/10. FIG. 16 shows that the cycling is stable and that the pure linear carbonate terminated PFPE can be used as a sole solvent (with the addition of a SEI additive if using a graphite anode) in a lithium ion electrode.

Figure 17:
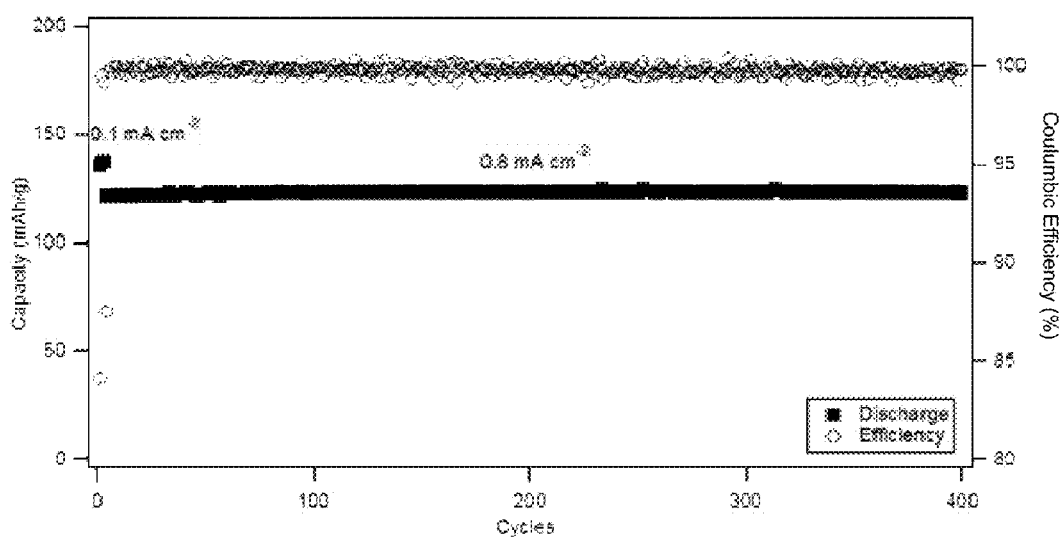
FIG. 17 shows cycling performance and stability of a linear carbonate terminated PFPE-based electrolyte composition in a LTO/NMC cell.

The performance of a linear carbonate terminated PFPE according to structure S7 was tested on a LTO/NMC cell. The electrolyte solvent was 8:2 (by weight) S7:EC. The cycling experiment was carried out at room temperature with 1.2M LiTFSI. Formation rate was C/10 and cycling rate was 1 C. FIG. 17 shows stable cycling over 400 cycles.

Example 19

Conductivity, Viscosity, and Flash Point of Mono-Functional Vs. Di-Functional Linear Carbonate Terminated PFPEs Flash points, viscosities and conductivities of mono- and di-functional PFPE-carbonates of various sizes were measured.

| Molecule | Mono- or di-functional | MW | $R_f$ MW | Viscosity (cP) at 20° C. | Flash Point (° C.) | SET | Conductivity 1.0M LiTFSI @ 25° C. (mS/cm) |
|---|---|---|---|---|---|---|---|
| S2 | di | 526 | 348 | 21 | 180 | None | 0.03 |
| S3 | di | 410 | 232 | 23 | 154 | None | 0.04 |
| S5 | mono | 606 | 517 | 5.6 | None | None | 0.02 |
| S6 | mono | 490 | 401 | 4.0 | None* | None | 0.04 |
| S7 | mono | 340 | 251 | 2.5 | None* | None | 0.12 |

S3 and S7 are directly comparable, with the S7 being the mono-carbonate version of S3. In an unexpected result, the conductivity of S7 is three times that of its di-functional counterpart.

Example 20

Small Molecule Carbonates

Flash points, SETs, and conductivities of heavily fluorinated small molecule carbonates were measured.

| Molecule | Mono- or di-functional | MW | $R_f$MW | Flash Point (° C.) | SET (S) | Conductivity 1.0 M LiTFSI @ 25° C. (mS/cm) |
|---|---|---|---|---|---|---|
| 1,1,1,3,3,3-hexafluoropropan-2-yl methyl carbonate | mono | 226 | 69 | None | None | Dissolves only 0.2 M salt, barely conducts |

$F_3C\diagup CH(CF_3)\diagup O\diagup C(=O)\diagup O\diagup CH_3$

-continued

| Molecule | Mono- or di-functional | MW | $R_f$MW | Flash Point (° C.) | SET (S) | Conductivity 1.0 M LiTFSI @ 25° C. (mS/cm) |
|---|---|---|---|---|---|---|
| bis(2,2,2-trifluoroethyl) carbonate 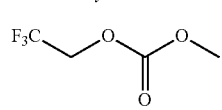 | mono | 226 | 69 | None | None | Does not dissolve salts |
| methyl 2,2,2-trifluoroethyl carbonate | mono | 158 | 69 | 40 | 3 | .83 |

The heavily fluorinated small molecule carbonates are non-conductive or highly flammable.

Example 21

Non-Fluorinated Carbonates

Flash points, SETs and conductivities of non-fluorinated carbonates were measured.

| Molecule | Mono- or di-functional | MW | Flash Point (° C.) | SET (S) | Conductivity 1.0 M LiTFSI @ 25° C. (mS/cm) |
|---|---|---|---|---|---|
| heptyl methyl carbonated | mono | 174 | 128 | 75 | 1.45 |
| 2-(2-methoxyethoxy)ethyl methyl carbonate 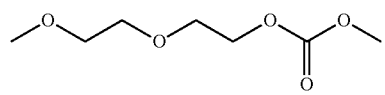 | mono | 178 | 87 | 90 | 0.49 |

These are conductive, but very flammable.

Example 22

Conductivity, Flash Point and SET of Electrolyte Mixtures Including PFPEs

The conductivities, flash points and SETs of the two electrolyte mixtures including PFPE's were determined and compared against a control electrolyte of EC:EMC.

| Formulation | Salt (1.0M) | Flash Point (° C.) | SET (S) | Conductivity 1.0M LiTFSI @ 25° C. (mS/cm) |
|---|---|---|---|---|
| S7:P3:EC:other additives (50:15:15:20) | LiTFSI | 128 | — | 1.77 |
| S7:EC (8:2) | LiTFSI | None* | — | 0.84 |
| EC:EMC (3:7) | LiPF$_6$ | 27 | long | 9.6 |

Example 23

Wick Tests of Electrolyte Mixtures Including PFPEs

3" long, ¼" diameter silica wicks were soaked in the electrolyte formulation and ignited with a Bunsen burner for 5 seconds. If there is no ignition, the flame was reapplied for 10 seconds. The speed at which the flame propagates the wick is measured. The test was performed with the wick in both the vertical and horizontal directions.

| Salt | Composition | Horizontal Wick Test | Vertical Wick Test |
|---|---|---|---|
| 1.0M LiPF$_6$ | EC:EMC (1:1) | 5.3 mm/sec | 38.1 mm/sec |
| 1.0M LiTFSI | S2 | No sustained flame | |
| 1.0M LiTFSI | S2:EC (9:1) | No sustained flame | |
| 0.8M LiTFSI | S2:GBL:EC (7:2:1) | 0.3 mm/sec | 3.62 mm/sec |
| 1.2M LiTFSI | S7:EC (8:2) | No sustained flame | |

Example 24

Figure 18:
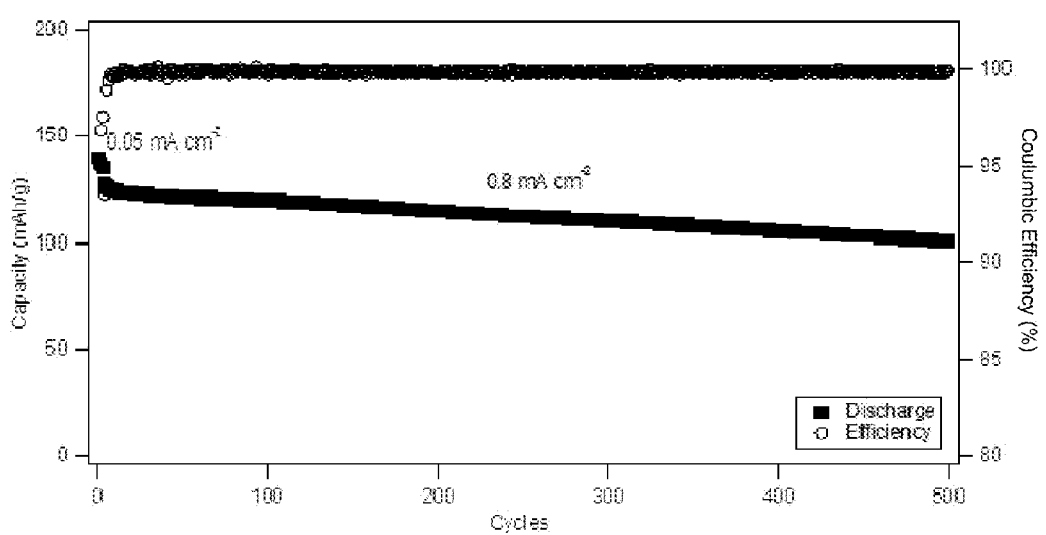
FIG. 18 shows cycling performance and stability of an electrolyte composition including a PFPE-carbonate and a PFPE-phosphate in a graphite/NMC cell.

Cycling Performance and Stability of Electrolyte Including a PFPE-Phosphate and a PFPE-Carbonate in a Coin Cell Battery The performance of an electrolyte including a PFPE-carbonate according to structure S7 and a PFPE-phosphate according to structure P3 was tested on a graphite/NMC cell. The S7 solution was neat (with the addition of 2% FEC as an SEI additive for the graphite cathode). The electrolyte solvent was 50:15:35 S7:P3:other additives including EC. The salt was 0.8M LiTFSI, 2% wt LiDFOB. Formation rate was C/20 and cycling rate was 1 C. FIG. 18 shows that the cycling is stable.

Example 25

Miscibility of Electrolyte Solvents Including Carbonate-Terminated Perfluoropolymers A mixture of S7, EC, other additives (55/15/20, wt) is not homogeneous in the absence of dissolved salt. Introduction of 10 wt % P3 resolves the issue and the mixture of S7/EC/other additives/P3 (55/15/20/10, wt) is homogeneous with and without dissolved lithium salt.

Example 26

Synthesis of Ether-Linked Phosphate Substituted Perfluoropolyethers

Synthesis of 1H,1H-Perfluoro-3,6,9-Trioxatridecanyl Dimethyl Phosphate (P10)

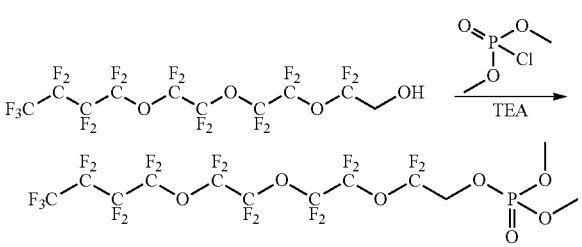

A 500 mL round bottom flask was charged with 50.0 g of 1H,1H-perfluoro-3,6,9-trioxatridecan-1-ol (0.091 mole), 13.4 mL (0.096 mole) of triethylamine, 250 ml of 1,1,1,3,3-pentafluorobutane and molecular sieves. The reaction mixture was dried overnight and subsequently transferred to a 500 mL Schlenk flask via cannula needle. The flask was equipped with a pressure equalized addition funnel, placed under nitrogen and cooled to 0° C. 13.3 mL (0.096 mole) of dimethyl chlorophosphate in 10 mL dry 1,1,1,3,3-pentafluorobutane was added dropwise, the reaction was continued at room temperature for additional 18 hours. Afterwards, the mixture was filtered, washed with 5% HCl$_{aq.}$, water and brine, then dried with anhydrous magnesium sulfate. The solvent was removed using rotary evaporator, and the product was isolated via a distillation under reduced pressure. 13.6 g (0.021 mole, 25% yield) of 1H,1H-perfluoro-3,6,9-trioxatridecanyl dimethyl phosphate was collected as a higher boiling clear, colorless fraction.

Synthesis of 1H,1H-Nonafluoro-3,6-Dioxaheptanyl Dimethyl Phosphate (P3)

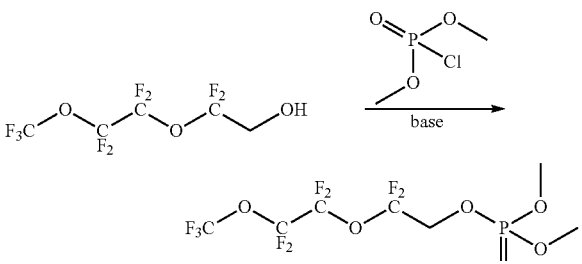

A 250 mL Schlenk flask equipped with a pressure equalized addition funnel was charged with 4.45 g (0.186 mole) of sodium hydride (or potassium tert-butoxide) and 150 mL of anhydrous THF, then placed under inert atmosphere and stirred at 0° C. 51.3 g (0.182 mole) of 1H,1H-nonafluoro-3,6-dioxaheptan-1-ol was added dropwise to the mixture over 1 hour, then stirred at room temperature for additional 20 minutes. A 500 mL three-neck, round bottom flask was charged with 20.0 mL (0.186 mole) of dimethyl chlorophosphate and 300 mL anhydrous THF. The reaction flask was flushed with nitrogen and cooled in an IPA-dry ice bath to −40 to −30° C. A pressure equalized addition funnel was connected to the flask. The solution of sodium 1H,1H-nonafluoro-3,6-dioxaheptan-1-oxide was added dropwise to the reaction mixture while maintaining the temperature of the cooling bath. Upon addition, the reaction was stirred at room temperature for 1 hour. Afterwards, 5 mL of water and 100 mL 1,1,1,3,3-pentafluorobutane were injected, the mixture was filtered, and solvents were removed using rotary evaporator. 1H,1H-nonafluoro-3,6-dioxaheptanyl dimethyl phosphate was isolated via a distillation under reduced pressure, collecting 60.9 g (0.156 mole, 84% yield) clear, colorless liquid (40-45° C./0.09-0.2 Torr fraction).

Example 27

Conductivity, Flammability, and Viscosity of PFPE-Phosphates

The conductivity, flash point, SET, and viscosity of structures P3 and P10 was determined.

| Molecule | MW | Viscosity (cP) at 20° C. | Flash Point (° C.) | SET (S) | Conductivity 1.0M LiTFSI @ 25° C. (mS/cm) |
|---|---|---|---|---|---|
| P10 | 656 | 17 | None | None | 0.07 |
| P3 | 390 | 6.7 | None | None | .37 |

What is claimed is:

1. A non-flammable electrolyte composition comprising:
   an electrolyte liquid comprising a functionally substituted perfluoropolyether according to Formula VIII:

R'—X—$R_f$ (VIII)

wherein
   R' is an unsubstituted lower alkyl linear carbonate group, X is an unsubstituted alkyl, alkoxy, or ether group, and $R_f$ is a branched or unbranched linear perfluoropolyether having a molar mass of between 200 g/mol and 550 g/mol; and
   an alkali metal salt.

2. The non-flammable electrolyte composition of claim 1, wherein the functionally substituted perfluoropolyether comprises about 30% to about 85% of the electrolyte composition.

3. The non-flammable electrolyte composition of claim 1, wherein the functionally substituted perfluoropolyether comprises about 40% to about 85% of the electrolyte composition.

4. The non-flammable electrolyte composition of claim 1, wherein the functionally substituted perfluoropolyether comprises is the largest component by weight of the electrolyte liquid.

5. The non-flammable electrolyte composition of claim 1, wherein $R_f$ is a branched or unbranched linear perfluoropolyether having a molar mass of between 200 g/mol and 450 g/mol.

6. The non-flammable electrolyte composition of claim 1, wherein $R_f$ is a branched or unbranched linear perfluoropolyether having a molar mass of between 200 g/mol and 300 g/mol.

7. The non-flammable electrolyte composition of claim 1, wherein the functionally substituted perfluoropolyether has a molar mass of between 250 g/mol and 650 g/mol.

8. The non-flammable electrolyte composition of claim 1, wherein R' is methyl carbonate.

9. The non-flammable electrolyte composition of claim 1, wherein $R_f$ has no more than two ether units.

10. The non-flammable electrolyte composition of claim 1, wherein $R_f$ has at least two ether subunits independently selected from —(CF$_2$CF(CF$_3$)O)—, —(CF(CF$_3$)CF$_2$O)—, —CF(CF$_3$)O—, —(CF$_2$O)—, or —(CF$_2$CF$_2$O)—.

11. The non-flammable electrolyte composition of claim 1, wherein the functionally substituted perfluoropolyether exhibits a viscosity of less than 10 cP at 20° C. and 1 atm.

12. The non-flammable electrolyte composition of claim 1, wherein X is a lower alkyl group.

13. The non-flammable electrolyte composition of claim 1, wherein the functionally substituted perfluoropolyether is selected from one of:

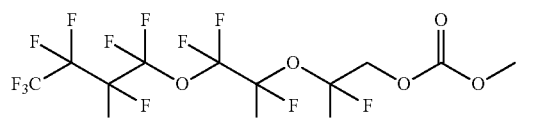

S6

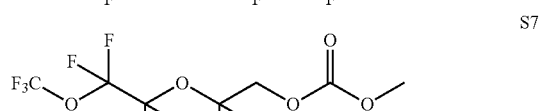

S7

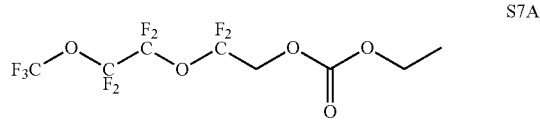

S7A

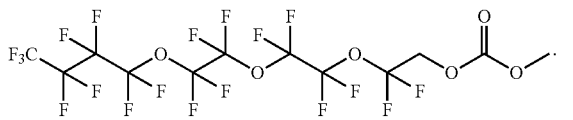

S8

14. The non-flammable electrolyte composition of claim 1, wherein the alkali metal salt comprises a lithium salt or a sodium salt.

15. The non-flammable electrolyte composition of claim 14, wherein the alkali metal salt is a lithium salt comprising LiPF$_6$ or LiTFSI or a mixture thereof.

16. The non-flammable electrolyte composition of claim 1, wherein the electrolyte liquid further comprises further comprising one or more of a conductivity enhancing additive, a viscosity reducer, a high voltage stabilizer, a wettability additive, or a flame retardant, or a mixture or combination thereof.

17. The non-flammable electrolyte composition of claim 1, wherein the electrolyte liquid further comprises a conductivity enhancing additive selected from ethylene carbonate (EC), propylene carbonate (PC), butylene carbonate (BC), fluoroethylene carbonate, γ-butyrolactone, or a mixture or combination thereof.

18. The non-flammable electrolyte composition of claim 17, wherein the conductivity enhancing additive comprises about 1% to about 40% of the non-flammable electrolyte composition.

19. The non-flammable electrolyte composition of claim 17, wherein the conductivity enhancing additive comprises about 5% to about 40% of the non-flammable electrolyte composition.

20. The non-flammable electrolyte composition of claim 17, wherein the electrolyte liquid comprises a high voltage stabilizer selected from 3-hexylthiophene, adiponitrile, sulfolane, lithium bis(oxalato)borate, γ-butyrolactone, 1,1,2,2-Tetrafluoro-3-(1,1,2,2-tetrafluoroethoxy)-propane, ethyl methyl sulfone, or trimethylboroxine or a mixture or combination thereof.

21. The non-flammable electrolyte composition of claim 17, wherein the electrolyte liquid comprises a wettability additive selected from triphenyl phosphite, dodecyl methyl carbonate, methyl 1-methylpropyl carbonate, methyl 2,2-dimethylpropanoate, or phenyl methyl carbonate or a mixture or combination thereof.

22. The non-flammable electrolyte composition of claim 17, wherein the electrolyte liquid comprises a flame retardant additive selected from trimethylphosphate, triethylphosphate, triphenyl phosphate, trifluoroethyl dimethylphosphate, tris(trifluoroethyl)phosphate, or mixture or combination thereof.

23. The non-flammable electrolyte composition of claim 16, wherein the viscosity reducer, high voltage stabilizer, and wettability additive each independently comprise about 0.5-6% of the electrolyte composition and the flame retardant comprises about 0.5-20% of the electrolyte composition.

24. The non-flammable electrolyte composition of claim 1, wherein the electrolyte liquid further comprises a phosphate or phosphonate-terminated perfluoropolymer.

25. The non-flammable electrolyte composition of claim 1, wherein the electrolyte composition has a flash point greater than 100° C.

26. The non-flammable electrolyte composition of claim 1, wherein the electrolyte composition has a flash point greater than 110° C.

27. The non-flammable electrolyte composition of claim 1, wherein the electrolyte composition has a flash point greater than 120° C.

28. The non-flammable electrolyte composition of claim 1, the electrolyte composition has self-extinguishing time of zero.

29. The non-flammable electrolyte composition of claim 1, wherein the composition does not ignite when heated to a temperature of about 150° C. and subjected to an ignition source for at least 15 seconds.

30. The non-flammable electrolyte composition of claim 1, wherein the composition has an ionic conductivity of from 0.01 mS/cm to about 10 mS/cm at 25° C.

31. The non-flammable electrolyte composition of claim 1, wherein the composition has an ionic conductivity of from 0.1 mS/cm to 3 mS/cm at 25° C.

32. A battery comprising:
an anode;
a separator;
a cathode;
at least one cathode current collector; and
a non-flammable electrolyte composition comprising an alkali metal salt and an electrolyte liquid comprising a functionally substituted perfluoropolyether according to Formula VIII:

R'—X—R$_f$     (VIII)

wherein
R' is an unsubstituted lower alkyl linear carbonate group, X is an unsubstituted alkyl, alkoxy, or ether group, and R$_f$ is a branched or unbranched linear perfluoropolyether having a molar mass of between 200 g/mol and 550 g/mol.

33. The battery of claim 32, wherein the at least one cathode current collector comprises aluminum.

34. The battery according to claim 33, wherein the non-flammable electrolyte composition comprises LiTFSI.

35. The battery according to claim 34, wherein non-flammable electrolyte composition prevents or reduces corrosion of the cathode current collector as compared to a reference battery comprising one or more organic carbonate solvents and LiTFSI, wherein the reference battery does not have a functionally substituted perfluoropolymer.

36. The battery of claim 32, wherein the battery has an operating temperature of about −30° C. to about 150° C.

37. The battery of claim 32, wherein the non-flammable electrolyte composition prevents or reduces the flammability of the battery as compared to a reference battery comprising one or more organic carbonate solvents and LiTFSI, wherein the reference battery does not have does not have a functionally substituted perfluoropolymer.

* * * * *